United States Patent
Miyamoto et al.

(10) Patent No.: US 8,303,621 B2
(45) Date of Patent: Nov. 6, 2012

(54) SURGICAL TREATMENT INSTRUMENT

(75) Inventors: Manabu Miyamoto, Hachioji (JP); Takumi Dejima, Mitaka (JP); Kazuo Banju, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 851 days.

(21) Appl. No.: 11/827,982

(22) Filed: Jul. 13, 2007

(65) Prior Publication Data
US 2008/0177134 A1 Jul. 24, 2008

Related U.S. Application Data

(63) Continuation of application No. PCT/JP2006/300270, filed on Jan. 12, 2006.

(30) Foreign Application Priority Data

Jan. 14, 2005 (JP) ................................ 2005-008155
Jun. 24, 2005 (JP) ................................ 2005-185538

(51) Int. Cl.
*A61B 17/00* (2006.01)
*A61B 17/04* (2006.01)

(52) U.S. Cl. ........................................ 606/205; 606/147
(58) Field of Classification Search .................. 606/170, 606/144, 147–148, 205–208; 600/141, 148
See application file for complete search history.

(56) References Cited

U.S. PATENT DOCUMENTS

| 5,330,502 A * | 7/1994 | Hassler et al. ................. 606/205 |
| 5,443,479 A | 8/1995 | Bressi, Jr. |
| 5,483,952 A * | 1/1996 | Aranyi .......................... 600/131 |
| 5,573,530 A * | 11/1996 | Fleury et al. ..................... 606/1 |
| 5,609,601 A * | 3/1997 | Kolesa et al. .................. 606/170 |
| 5,766,196 A | 6/1998 | Griffiths |
| 5,951,575 A | 9/1999 | Bolduc et al. |
| 2002/0177874 A1* | 11/2002 | Nicholas et al. .............. 606/206 |
| 2004/0193212 A1* | 9/2004 | Taniguchi et al. ............. 606/205 |

FOREIGN PATENT DOCUMENTS

| JP | 07-241297 | 9/1995 |
| JP | 08-164141 | 6/1996 |
| JP | 2002-282257 | 10/2002 |
| JP | 2004-008367 | 1/2004 |
| JP | 2005-349180 | 12/2005 |
| WO | WO 2004/066848 | 8/2004 |
| WO | WO 2005110253 A1 * | 11/2005 |

* cited by examiner

*Primary Examiner* — Gary Jackson
*Assistant Examiner* — Jonathan Hollm
(74) *Attorney, Agent, or Firm* — Scully, Scott, Murphy & Presser, P.C.

(57) ABSTRACT

A surgical treatment instrument according to the invention includes an insertion portion, an operation portion provided on one end of the insertion portion, a treatment portion provided so as to extend from the other end of the insertion portion, two gripping members provided on the treatment portion, each having a gripping face, an open/close operating member provided on the operation portion to perform opening/closing by at least one of the two griping members being moved, variable angle operating members respectively provided on the operation portion to change the treatment portion to a predetermined angle, a braked member provided within the operation portion and operating in conjunction with the operation of the variable angle operation portion, and a braking member provided within the operation portion to brake the braked member by operating in conjunction with the operation of the open/close operation member, wherein the treatment portion maintains a predetermined angle by the braked member being braked by the braking member.

21 Claims, 39 Drawing Sheets

SURGICAL TREATMENT INSTRUMENT

CROSS REFERENCE TO RELATED APPLICATION

This application is a continuation application of PCT/JP2006/300270 filed on Jan. 12, 2006 and claims benefit of Japanese Applications No. 2005-008155 filed in Japan on Jan. 14, 2005, and No. 2005-185538 filed in Japan on Jun. 24, 2005, the entire contents of each of which are incorporated herein by their reference.

BACKGROUND OF THE INVENTION

1. Field of the Invention

The present invention relates to a surgical treatment instrument for grasping a needle for the purpose of anastomosis of tissue or the like using an endoscope.

2. Description of the Related Art

In recent years, as a surgery for performing coronary artery revascularization of the heart using endoscopy, for example, bypass surgery is known, wherein a surgical treatment instrument and forceps serving as an endoscope and needle holding tool are inserted into the chest cavity via a trocar puncturing the chest wall, dissecting a portion of the coronary artery with the forceps to provide an anastomosis opening, guiding an internal thoracic artery to the anastomosis opening with the grasping forceps, and the internal thoracic artery is connected by anastomosis to the anastomosis opening by the surgical treatment instrument.

As a surgical treatment instrument for such a surgery, a surgical treatment instrument is known which is disclosed in U.S. Pat. No. 5,951,575, which has a configuration wherein an insertion portion having a bending portion on the distal end portion is provided, the distal end portion of the insertion portion is provided with a pair of jaws capable of opening/closing and rotating around the axis of the insertion portion. A driving cable for transmitting turning force and opening/closing force to the distal end portion of the insertion portion is inserted from an operation portion through the insertion portion to the distal end portion.

Also, a surgical treatment instrument as disclosed in Japanese Unexamined Patent Application Publication No. 08-164141 for example, is used with a configuration wherein an exterior member is provided with a flexible joint member which joints the operation portion and distal end portion of the treatment instrument, the interior portion of the exterior member being configured with an internal member movable in the axial direction.

SUMMARY OF THE INVENTION

A surgical treatment instrument according to the present invention comprises an insertion portion, an operation portion provided on one end of the insertion portion, a treatment portion provided so as to extend from the other end of the insertion portion, two gripping members provided on the treatment portion, each having a gripping face, an open/close operating member provided on the operation portion to perform opening/closing by at least one of the two griping members being moved, variable angle operating members respectively provided on the operation portion to change the treatment portion to a predetermined angle, a braked member provided within the operation portion and operating in conjunction with the operation of the variable angle operation portion, and braking member provided within the operation portion to brake the braked member by operating in conjunction with the open/close operation of the open/close operation member, wherein the treatment portion maintains a predetermined angle by the braked member being braked by the braking member.

DETAILED DESCRIPTION OF THE PREFERRED EMBODIMENT(S)

Embodiments according to the present invention will be described below with reference to the drawings.

First Embodiment

A first embodiment according to the present invention will be described below.

Figure 1:
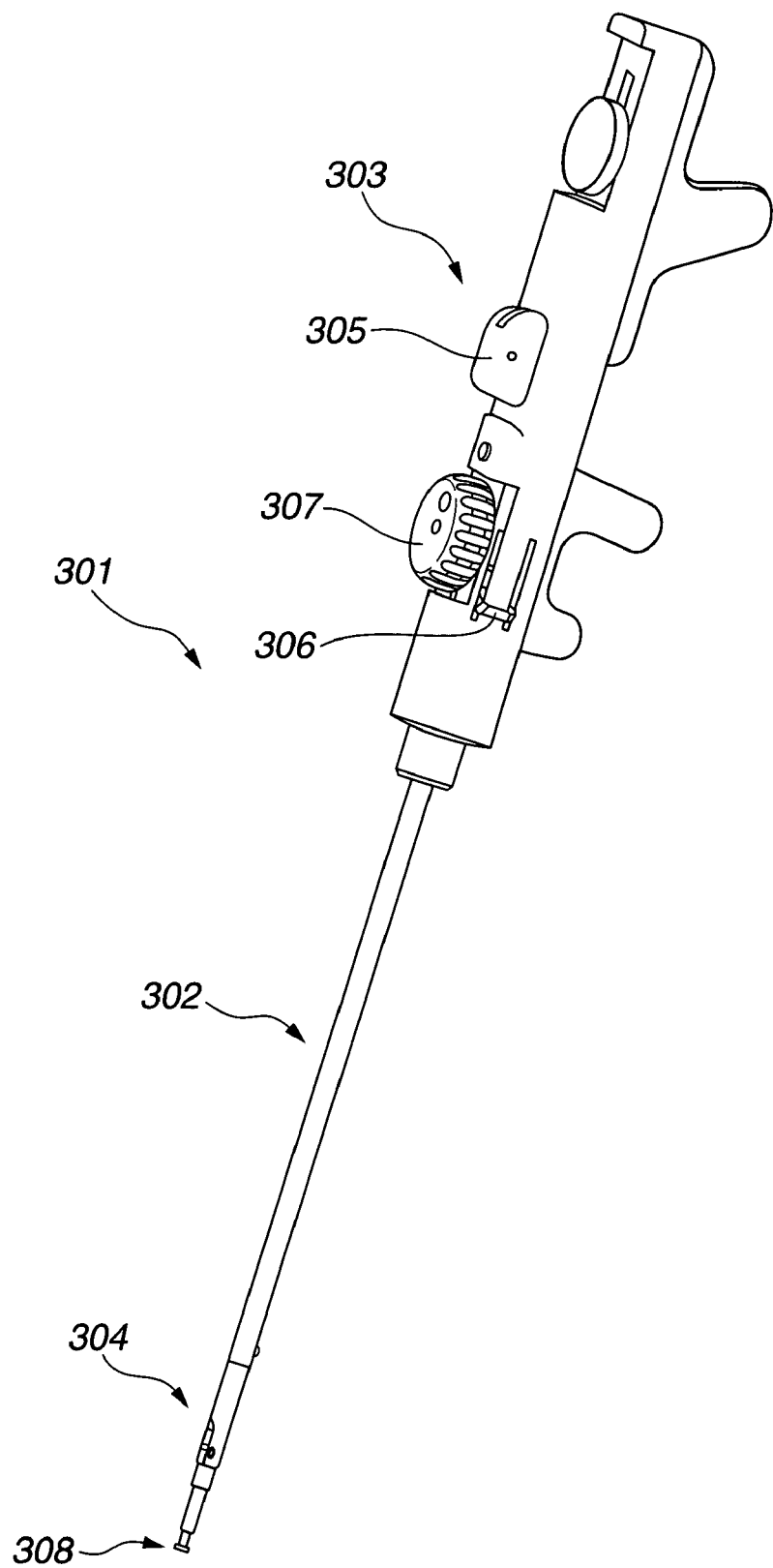
FIG. 1 is an external perspective view of a needle driver relating to a first embodiment of the present invention, as seen from one side of the front diagonal direction.
Figure 2:
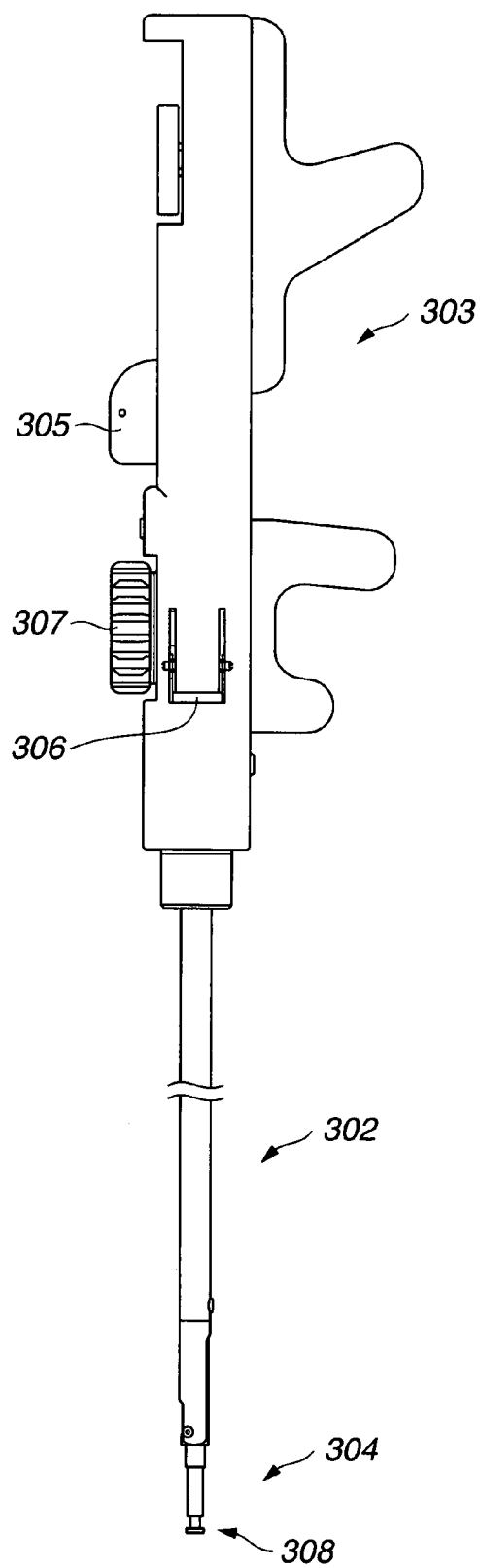
FIG. 2 is a front view of the needle driver shown in FIG. 1.
Figure 3:
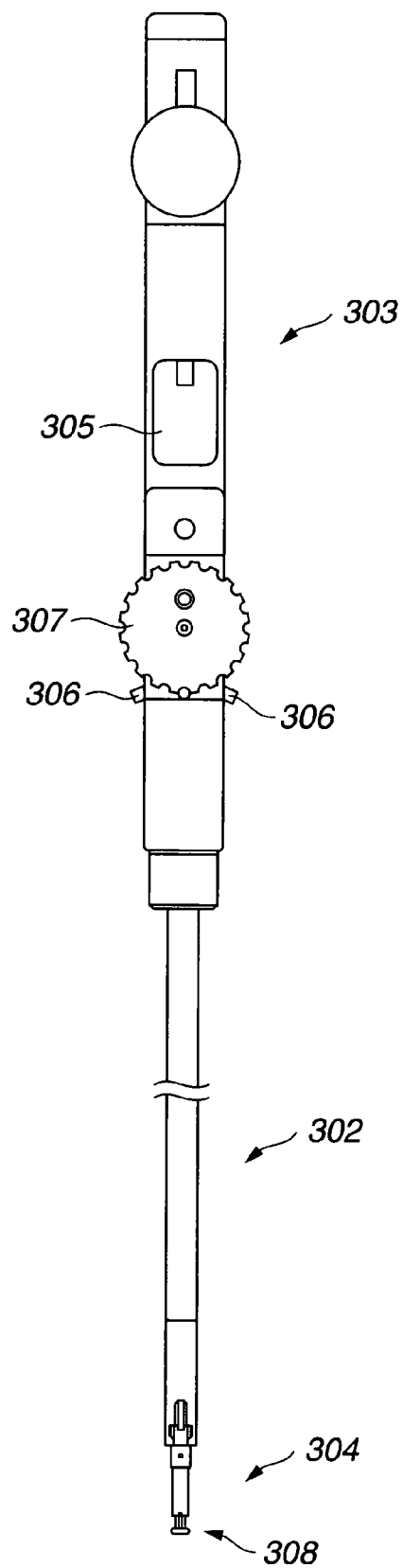
FIG. 3 is a left side view of the needle driver shown in FIG. 1, as seen from one side direction (left side direction).
Figure 4:
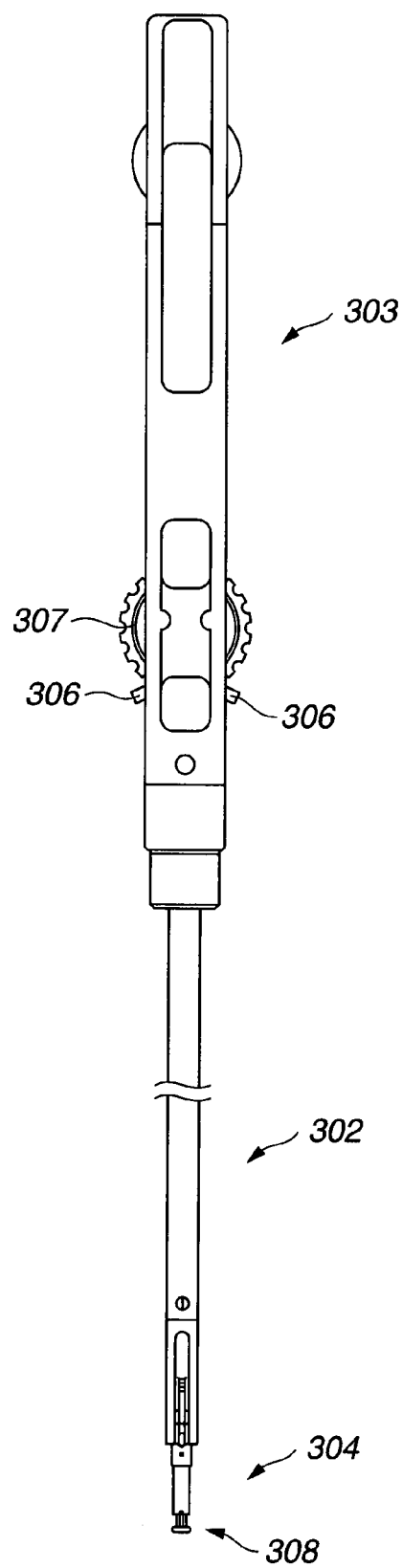
FIG. 4 is a right side view of the needle driver shown in FIG. 1, as seen from another side direction (right side direction).

FIG. 1 is an external perspective view of a needle driver relating to the first embodiment as seen from one side of the front diagonal direction. FIG. 2 is a front view of the needle driver according to the present embodiment, FIG. 3 is a left side view of the needle driver according to the present embodiment, as seen from one side direction (left side direction), and FIG. 4 is a right side view of the needle driver according to the present embodiment, as seen from another side direction (right side direction).

As shown in FIG. 1 through FIG. 4, a needle driver 301 is a surgical treatment instrument configured with the primary parts of an insertion portion 302, an operation portion 303 provided on one end (proximal end side) of the insertion portion 302, and a treatment portion 304 provided so as to extend from the other end of the insertion portion 302.

The insertion portion 302 has a generally cylindrical shape having a predetermined length. Also the operation portion 303 is a member having a generally rectangular shape disposed integrally on the proximal end side of the insertion portion 302 on the same axis as the longitudinal axis of the insertion portion 302, wherein a surgeon is able to grasp the operation portion 303 with one hand and perform operations to be described later.

Also, on the operation portion 303 are provided an open/close button 305 serving as an open/close operating member for performing opening/closing operations of the treatment portion 304, a variable angle lever 306 serving as a variable angle operating member for performing an operation to change the angle of the extending direction of the treatment portion 304, and a turning dial 307 serving as a turning operating member for performing turning operation of the treatment portion 304.

The proximal end portion of the open/close button 305 is pressed in a direction separated from the exterior portion of the operation portion 303 by pressing force of a spring to be described later. Also, one end on the proximal end side of a traction wire to be described later is engaged with a member linked to the open/close button 305. Upon the open/close button 305 being pressed in, the force resisting the pressing force of the spring within the treatment portion to be described later is applied to the traction wire. The configuration of the open/close button 305 will be described later.

The treatment portion 304 provided so as to extend from one end of the insertion portion 302 has a gripping portion 308 on the distal end portion thereof, wherein the axial direction of the gripping portion 308, i.e. the extending direction of the treatment portion 304, can be changed within a predetermined range of angles as to the axial direction of the insertion portion 302, e.g. in the range of 0 to 90 degrees, for example. In other words, the needle driver 301 has provided thereupon a variable angle means for changing the angle in the extending direction of the treatment portion 304 as to the axis of the insertion portion 302.

Figure 5:
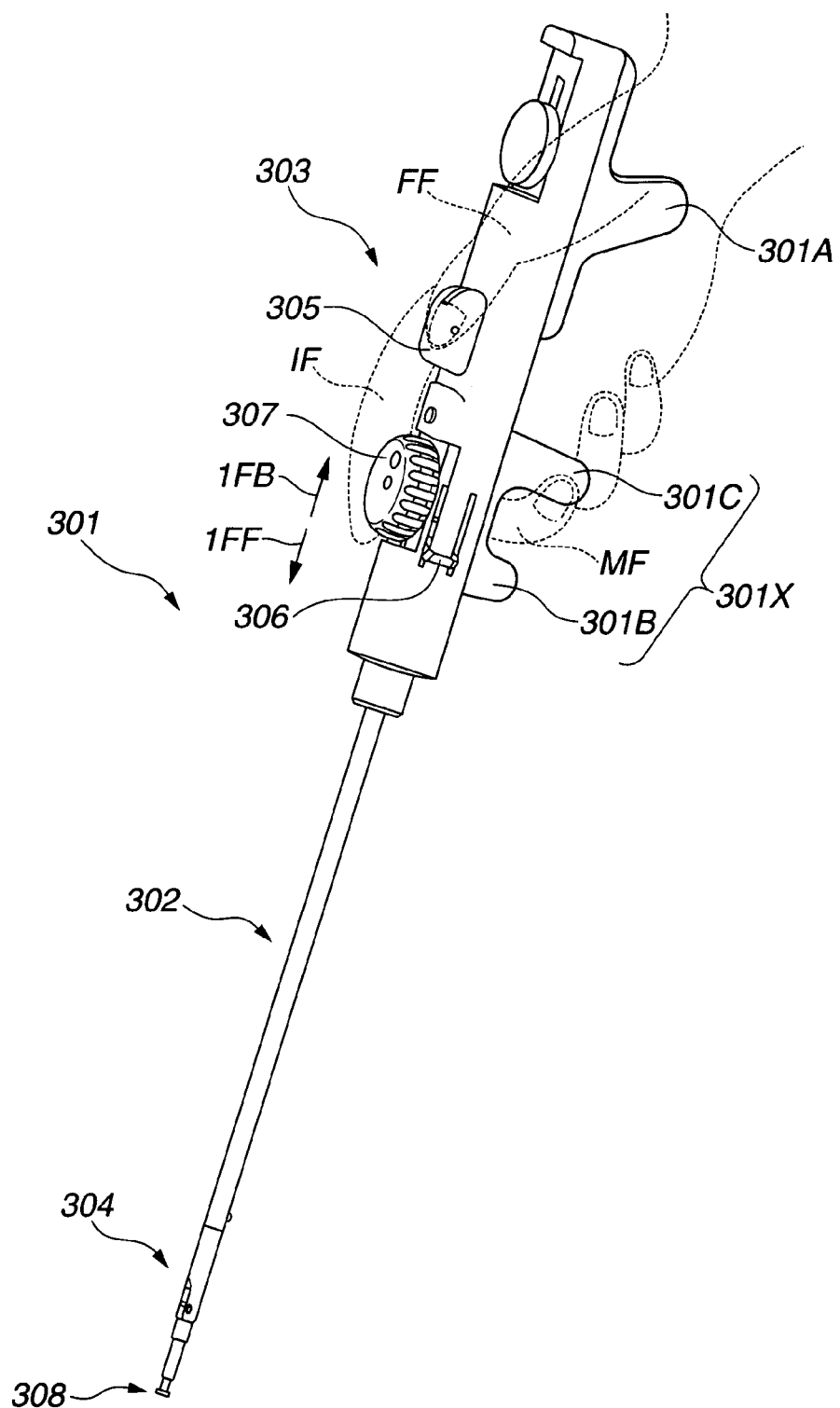
FIG. 5 is a diagram for describing the state of grasping the needle driver shown in FIG. 1.

FIG. 5 is a diagram for describing a state wherein the needle driver 301 in FIG. 1 is being grasped by a surgeon. As shown in FIG. 5, the surgeon places the base of the thumb FF and index finger IF against a palm holding member 301A made of resin, and places the middle finger MF between two protruding portions 301B and 301C of a finger holding member 301X made of resin, whereby the surgeon can grasp the needle drive 301 firmly and in a stable manner. As shown in FIG. 5, while in a state of the surgeon grasping the needle driver 301, the surgeon can operate the turning dial 307 and variable angle lever 306 with the index finger IF. The turning dial 307 and variable angle lever 306 can be operated by the index finger IF in the distal end direction IFF of the insertion portion 302 and the proximal end direction IFB. Further, the open/close button 305 can be operated by the thumb FF.

Further, the palm holding member 301A extends diagonally from the side portion of the operation portion 303 somewhat towards the proximal end side, whereby the surgeon can firmly grasp the needle driver 301 by the palm holding member 301A and the palm in close contact at the time of grasping.

Next the configuration of the distal end portion of the needle driver 301 will be described based on FIG. 6 through FIG. 11.

FIG. 6 through FIG. 11 are diagrams for describing the configuration of the distal end portion of the needle driver 301 including the treatment portion 304.

Figure 6:
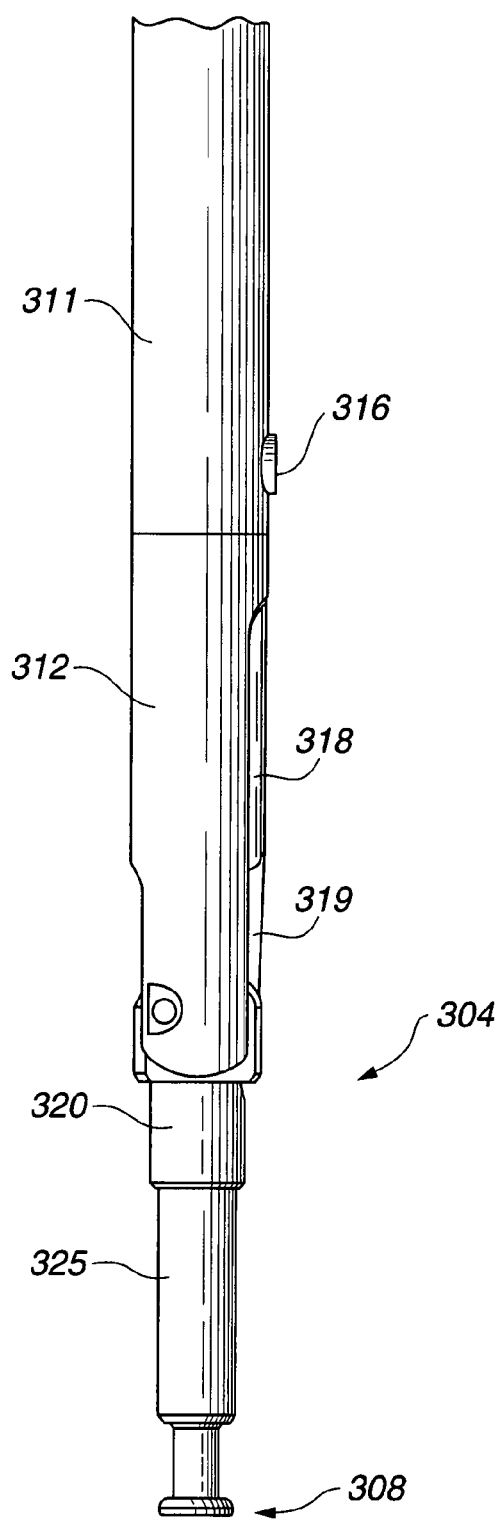
FIG. 6 is a front view of the distal end portion including the treatment portion of the needle driver shown in FIG. 1.
Figure 7:
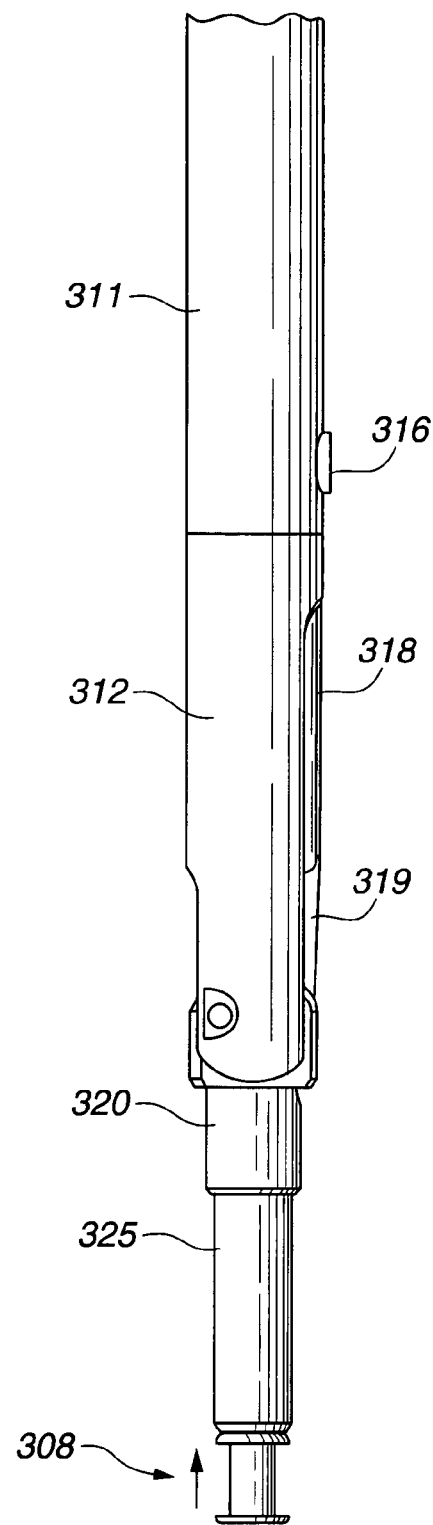
FIG. 7 is a front view of the distal end portion wherein the gripping portion of the treatment portion of the needle driver shown in FIG. 1 is in an open state.
Figure 8:
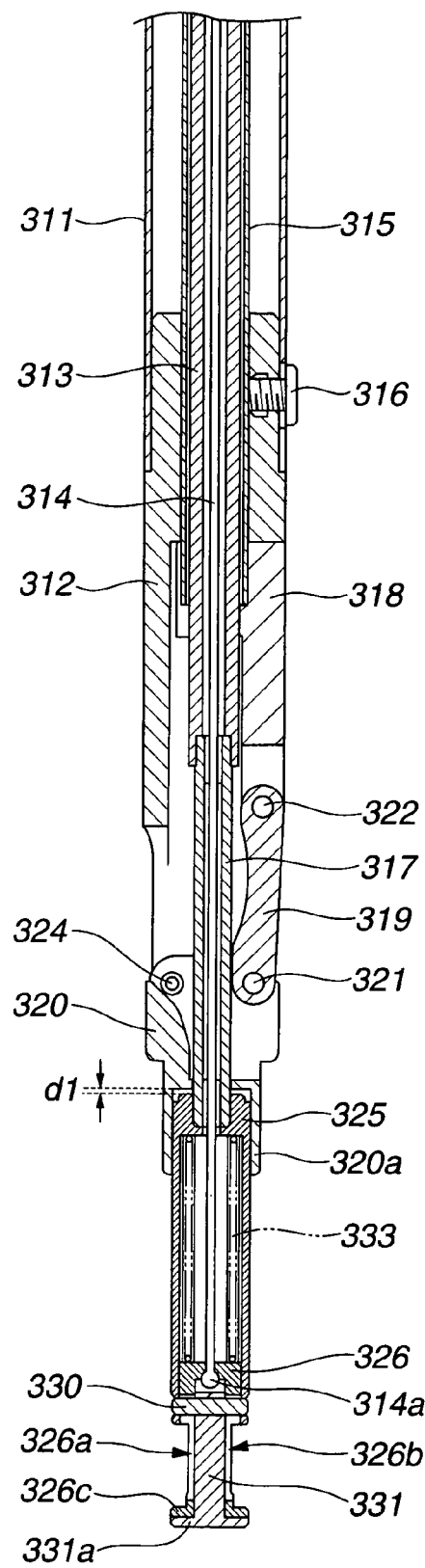
FIG. 8 is a cross-sectional view of the distal end portion including the treatment portion along the axial direction of the needle driver shown in FIG. 1.
Figure 9:
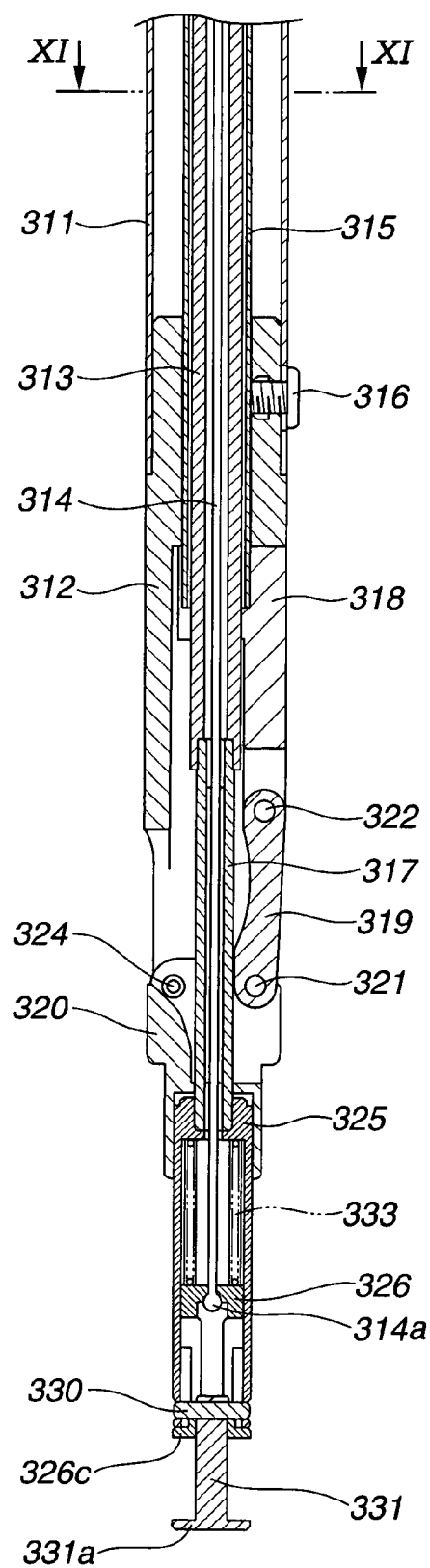
FIG. 9 is a cross-sectional view of the distal end portion along the axial direction of the needle driver shown in FIG. 1, wherein the gripping portion of the treatment portion is in an open state.
Figure 10:
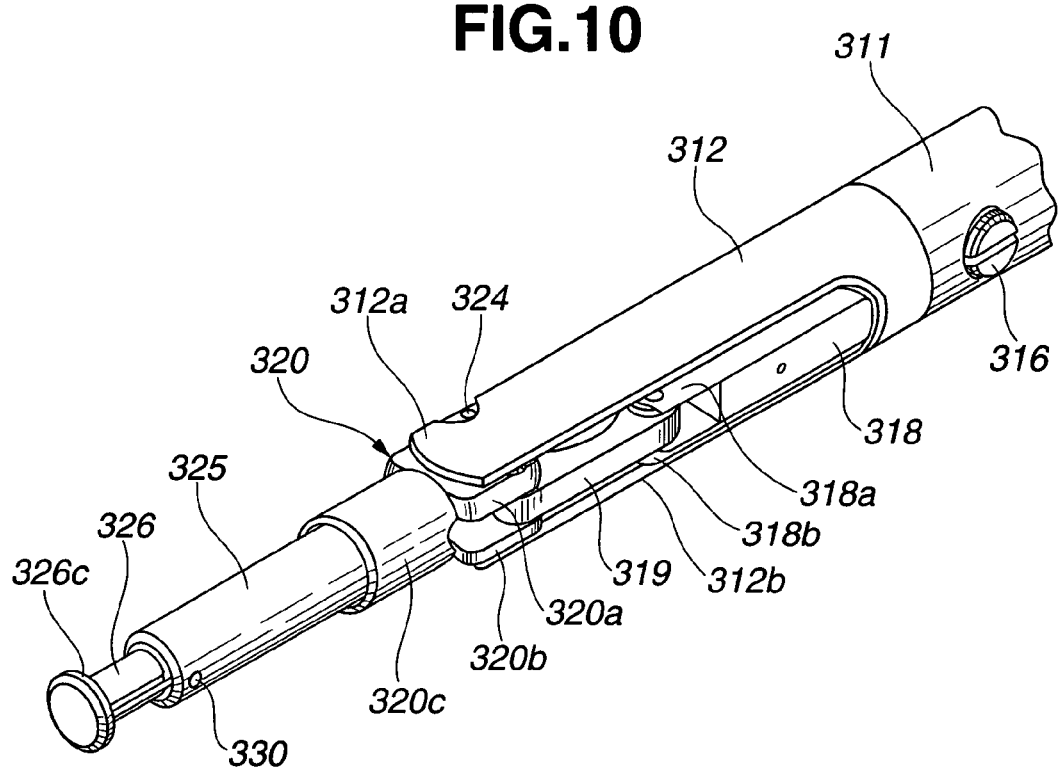
FIG. 10 is a perspective view for describing the internal configuration of the distal end portion of the needle driver shown in FIG. 1.
Figure 11:
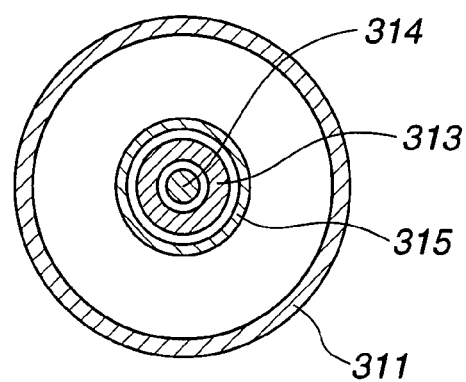
FIG. 11 is a cross-sectional view of the needle driver shown in FIG. 1, taken along the XI-XI line in FIG. 9.

FIG. 6 is a front view of the distal end portion including the treatment portion 304 of the needle driver 301. FIG. 7 is a front view of the distal end portion wherein the gripping portion 308 of the treatment portion 304 is in an open state. FIG. 8 is a cross-sectional view of the distal end portion including the treatment portion 304 along the axial direction of the needle driver 301. FIG. 9 is a cross-sectional view of the distal end portion along the axial direction of the needle driver 301, wherein the gripping portion 308 of the treatment portion 304 is in an open state. FIG. 10 is a perspective view for describing the internal configuration of the distal end portion. FIG. 11 is a cross-sectional view, taken along the XI-XI line in FIG. 9.

The insertion portion 302 has a stainless steel pipe, i.e. a sheath 311 serving as a cylindrical member. The distal end side of the sheath 311, i.e. the treatment portion 304 side, is fixed to a distal end housing member 312 made of stainless steel. The distal end housing member 312 has a cylindrically shaped fitting portion which fits with the inner circumference face of the sheath 311 to the proximal end side of the distal end housing member 312, i.e. the sheath 311 side.

As shown in FIG. 9, the central portion of the distal end housing member 312 has a space therewithin, and also has a channel-shaped portion wherein the cross-sectional shape orthogonal to the axis of the insertion portion 302 is in a channel shape. The distal end housing member 312, as shown in FIG. 10, has two arm portions 312a and 312b on the distal end side (i.e., the gripping portion 308 side) which extend toward the distal end side so as to sandwich the interior space communicated with the interior space within the channel-shaped portion.

As shown in FIG. 8, a bending force transmitting pipe 315 made of stainless steel serving as a shaft member is inserted in the sheath 311. The bending force transmitting pipe 315 is a member for changing the angle of the extending direction of the treatment portion 304 so as to bend the treatment portion 304.

The bending force transmitting pipe 315 is inserted in the sheath 311, and a turning force transmitting pipe 313 made of stainless steel serving as a shaft member is inserted in the bending force transmitting pipe 315.

The turning force transmitting pipe 313 is a pipe for transmitting turning force to the distal end portion. A traction wire 314 made of stainless steel for the opening/closing operations of the gripping portion 308 to be described later is inserted in the turning force transmitting pipe 313. Accordingly, as shown in FIG. 11, the bending force transmitting pipe 315, the turning force transmitting pipe 313, and the traction wire 314 are disposed on the inner side of the sheath 311 along the same axis.

The traction wire 314 is a wire member which is pulled to the operation portion 303 side for performing opening operation of the gripping portion 308, configured flexibly by weaving fine stainless steel wires. Also, a fluorine resin may be coated on the wire surface so as to reduce sliding resistance, and also to facilitate forward/backward movement, within the sheath 311.

The distal end housing member 312 is fixed to the sheath 311 by a stopping screw 316 made of stainless steel. Further the distal end portion of the sheath 311 and the distal end housing member 312 are fixed together by having an adhesive, e.g., an epoxy resin type adhesive, adhered thereto. The turning force transmitting pipe 313 is inserted so as to be turnably slidable with the axis of the turning force transmitting pipe 313 as the center of rotation, and the bending force transmitting pipe 315 is inserted so as to be movable forward/backward in the axial direction of the bending force transmitting pipe 315.

A turning force transmitting coil 317 made of stainless steel is fixed to the distal end of the turning force transmitting pipe 313. The turning force transmitting coil 317 is a flexible coil for transmitting turning force to the distal end portion of the insertion portion 302. The traction wire 314 is inserted into the turning force transmitting coil 317. Since the turning force transmitting pipe 313 is made of metal, the turning force by the turning operation of the turning dial 307 on the operation portion 303 can be transmitted to the turning force transmitting coil 317 in a sure manner.

The turning force transmitting coil 317 connected to the turning force transmitting pipe 313 is configured by layering three coils so as to form a triple-winding adhered configuration. A second coil is provided so as to be layered on top of the bottom-most coil in the opposite winding direction from the winding direction of the bottom-most coil, and a third coil is provided so as to be layered on top of the second-bottom coil in the opposite winding direction from the winding direction of the second-bottom coil (i.e., the same winding direction as the bottom-most coil).

Both end portions of the turning force transmitting coil 317 are brazed, and dissected after being brazed. Consequently, the thickness of both end portions are thinner than the thickness at the central portion. Both end portions are then fixed by brazing to the turning force transmitting pipe 313 and a turning portion base member 325, respectively.

The bending force transmitting pipe 315 is linked to a bending portion base member 320 made of stainless steel, via a joint member 318 serving as a joining member made of stainless steel and a linking member 319 made of stainless steel. The proximal end portion of the joint member 318 is configured so that the turning force transmitting pipe 313 is inserted so as to be slidable in the axial direction and around the axis of the turning force transmitting pipe 313. Further, the bending force transmitting pipe 315 is linked to the joint member 318 by fitting with the joint member 318 and proximal end portion and adhered thereto, whereby the joint member 318 moves backward/forward in the same direction according to the movement backward/forward of the bending force transmitting pipe 315 along the axial direction of the insertion portion 302.

Figure 12:
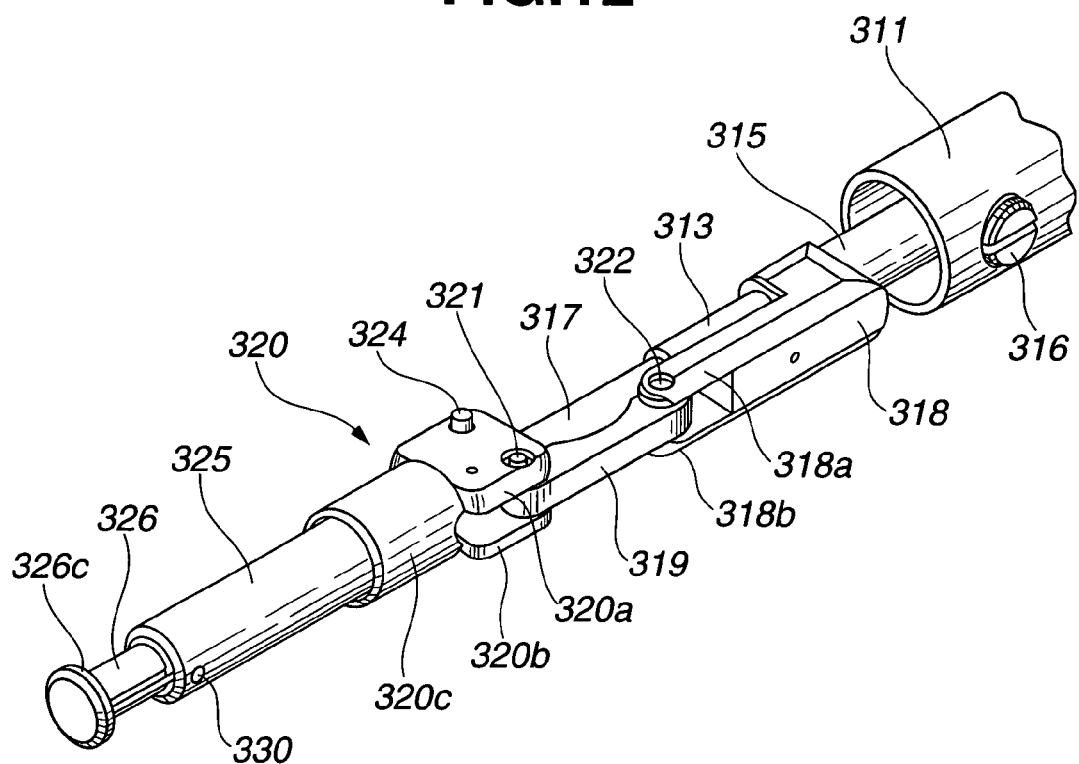
FIG. 12 is a perspective view for describing the internal configuration of the distal end portion of the needle driver shown in FIG. 1, wherein the distal end housing member is omitted.

The connection relations between the bending force transmitting pipe 315, joint member 318, linking member 319, and bending portion base member 320 will be described with reference to FIG. 10 and FIG. 12. FIG. 12 is a perspective view for describing the internal configuration of the distal end portion, wherein the distal end housing member 312 is omitted.

As shown in FIG. 10, the distal end housing member 312 fits with the inner circumferential face of the sheath 311 at the proximal end side of the distal end housing member 312. A portion of the bending force transmitting pipe 315, the turning force transmitting coil 317, joint member 318, linking member 319, and a portion of the bending portion base member 320 are disposed within the central portion and the distal end portion of the distal end housing member 312. A bending portion base member 320 is disposed between the two arm portions 312a and 312b of the distal end housing member 312, whereby the bending portion base member 320 and the distal end housing member 312 are linked with a pin 324. Specifically, the bending portion base member 320 and the distal end housing member 312 are linked by the pin 324 which fits in the two arm portions 312a and 312b being fit into a hole provided on the bending portion base member 320, whereby the bending portion base member 320 is turnable so as to turn on the axis of the pin 324.

Also, as shown in FIG. 12, the joint member 318 has two arm portions 318a and 318b on the distal end side thereof. The linking member 319 is a bar member having hole portions on each of both end portions. The bending portion base member 320 has two arm portions 320a and 320b on the proximal end side thereof. Note that the bending portion base member 320 has a cylindrical portion 320c on the distal end side thereof, whereby the proximal end portion of the turning portion base member 325 is fit into the inner side of the cylindrical portion 320c.

The bending portion base member 320 and the linking member 319 are linked together so as to sandwich the distal end portion of the linking member 319 between the two arm portions 320a and 320b of the bending portion base member 320, by a pin 321 which passes through the two arm portions 320a and 320b, and a hole of the distal end portion of the linking member 319. The pin 321 is fixed by laser welding at the end portion of the bending portion base member 320, but the linking member 319 is turnable so as to turn on the axis of the pin 321.

Also, the joint member 318 and the linking member 319 are linked together so as to sandwich the proximal end portion of the linking member 319 between the two arm portions 318a and 318b, by a pin 322 which passes through the two arm portions 318a and 318b, and a hole of the proximal end portion of the linking member 319. The pin 322 is fixed by laser welding at the end portion of the joint member 318, but the linking member 319 is turnable so as to turn on the axis of the pin 322.

Figure 13:
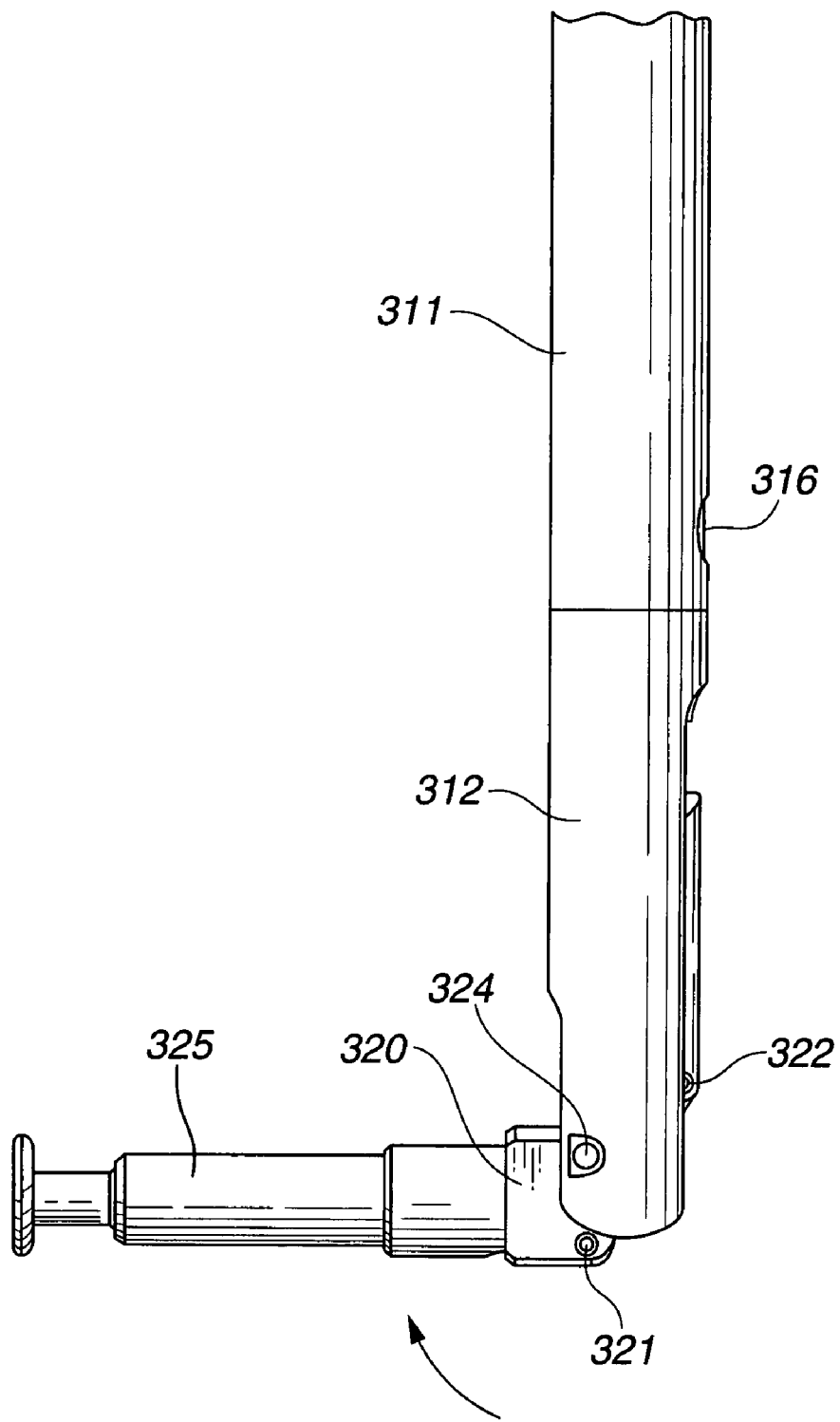
FIG. 13 is a front view of the distal end portion showing a state wherein the treatment portion of the needle driver shown in FIG. 1 is bent 90 degrees as to the axis of the insertion portion.
Figure 14:
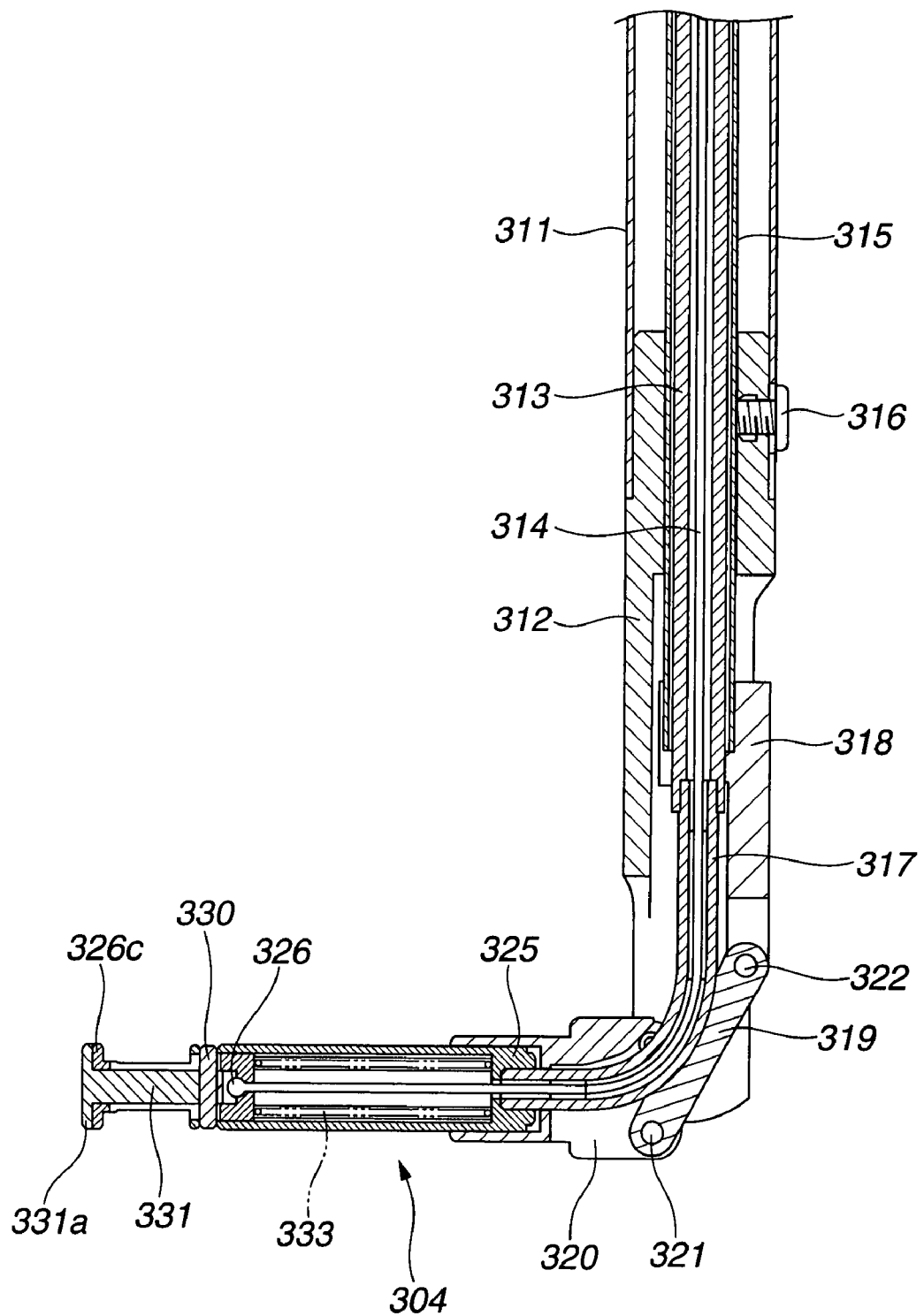
FIG. 14 is a cross-sectional view of the distal end portion showing a state wherein the treatment portion of the needle driver shown in FIG. 1 is bent 90 degrees as to the axis of the insertion portion.

Accordingly, by operating the variable angle lever 306 of the operation portion 303, the bending force transmitting pipe 315 advances to the distal end side in the axial direction of the operation portion 303, whereby the bending portion base member 320 turns on the pin 324. FIG. 13 is a front view of the distal end portion showing a state wherein the treatment portion 304 is bent 90 degrees as to the axis of the insertion portion 302. FIG. 14 is a cross-sectional view of the distal end portion showing a state wherein the treatment portion 304 is bent 90 degrees as to the axis of the insertion portion 302. Also, by operating the variable angle lever 306, the bending force transmitting pipe 315 is returned to the proximal side in the axial direction of the operation portion 303, whereby the extending direction of the treatment portion 304 has a smaller angle than 90 degrees as to the axis of the insertion portion 302. Note that the pins 321, 322, and 324 are each made of stainless steel. A mechanism whereby the surgeon moves the variable angle lever 306 of the operation portion 303 forward/backward in the axial direction of the insertion portion 302 by a finger, thereby the bending force transmitting pipe 315 moving forward/backward in the axial direction of the operation portion 303, will be described later.

Returning to FIG. 8, a cylindrically shaped turning portion base member 325 is fitted into the cylindrical portion 320c of the bending portion base member 320 so as to be turnable so as to turn on the axis of the turning portion base member 325. The turning portion base member 325 has an opening portion on the distal end side and a bottom portion on the proximal end side thereof. A hole is formed on the proximal end side bottom portion of the turning portion base member 325, wherein the distal end portion of the turning force transmitting coil 317 is inserted into the hole, and fixed by brazing as described above.

The turning force transmitting coil 317 is fixed by brazing to the turning force transmitting pipe 313 at the proximal end side thereof as described above, and is also fixed by brazing to the turning portion base member 325 at the distal end side thereof. The distal end portion of the turning force transmitting coil 317 is inserted into the proximal end side bottom portion of the turning portion base member 325 and brazed. The proximal end portion of the turning force transmitting coil 317 is inserted into a step portion formed in the inner portion of the distal end portion of the turning force transmitting pipe 313 and brazed. Accordingly, upon the turning force transmitting pipe 313 being turned so as to turn on the axis of the turning force transmitting pipe 313, the turning force transmitting coil 317 and turning portion base member 325 also turn similarly so as to transmit the turning amount of the turning force transmitting pipe 313 to the treatment portion 304.

Note that as shown in FIG. 8, if the treatment portion 304 is not in the state of being bent, the proximal end side bottom portion of the turning portion base member 325 and the proximal end side bottom portion of the turning portion base member 325 are separated by a predetermined distance d1. As the treatment portion 304 becomes bent, the proximal end side bottom portion of the turning portion base member 325 and the bottom portion of the proximal end side of the turning portion base member 325 become closer together. Accordingly, the proximal end side bottom portion of the turning portion base member 325 and the proximal end side bottom portion of the turning portion base member 325 are separated only by the predetermined distance d1, so that when the treatment portion 304 is maximally bent (for example up to 90 degrees) as described later, the proximal end side bottom portion of the turning portion base member 325 and the proximal end side bottom portion of the turning portion base member 325 do not come into contact thereby generating frictional resistance. Note that by setting the predetermined distance d1 to zero (0), frictional resistance increases, but movement of the turning portion base member 325 in the treatment portion 304 longitudinal axial direction as to the bending portion base member 320 accompanying the bending operation can be suppressed.

A griping portion 308 including two gripping members which grip a needle is provided on the distal end portion of the treatment portion 304, wherein one is a movable gripping piece 326 and the other is a fixed gripping piece 331.

The turning portion base member 325 is made of stainless steel, and a portion of the movable gripping piece 326 which is one of the gripping portion 308 of the treatment portion 304 is inserted into the turning portion base member 325 from the opening portion of the distal end side. The movable gripping piece 326 is made of stainless steel, and is a cylindrical member having an inner-facing flange portion on the proximal end side thereof.

A hole is provided on the bottom portion of the proximal end side of the movable gripping piece 326 such that the traction wire 314 can be inserted through. A terminal enlarged portion 314a is formed on the distal end portion of the traction wire 314, which is formed by melting the distal end portion, such terminal enlarged portion 314a being fixed to the inner side of the bottom portion of the movable gripping piece 326. Accordingly, when the traction wire 314 is pulled toward the operation portion 303 side, the movable gripping piece 326 also moves to the operation portion 303 side.

Figure 15:
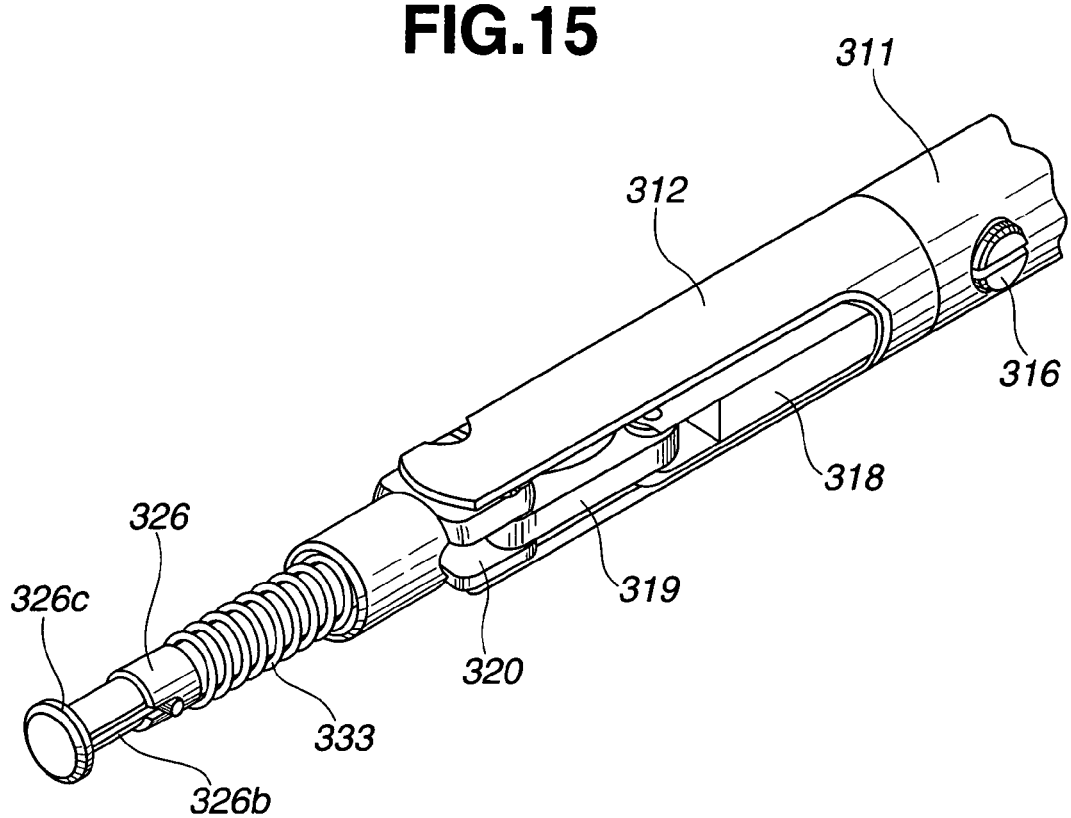
FIG. 15 is a perspective view for describing the internal configuration of the distal end portion of the needle driver shown in FIG. 1, wherein a turning portion base member is omitted.

A spring 333 made of stainless steel is provided on the inner side of the cylindrically-shaped portion of the turning portion base member 325, in the space between the exterior face of the bottom portion of the movable gripping piece 326 and the interior face of the bottom portion of the turning portion base member 325 which faces the exterior face, in a state of being compressed, so as to be assembled on the traction wire 314. FIG. 15 is a perspective view for describing the internal configuration of the distal end portion, wherein the turning portion base member 325 is omitted. As shown in FIG. 15, the spring 333 is provided in a compressed state on the inner portion of the turning portion base member 325.

As described above, a portion of the movable gripping piece 326 made of stainless steel, serving as one of the gripping members, is fitted into the distal end side of the turning portion base member 325, as described above. The movable gripping piece 326 is in a generally cylindrical shape having two slot portions 326a and 326b, and the proximal end portion has a bottom portion as described above. An inner-facing flange portion is formed on the bottom portion thereof. The distal end portion of the movable gripping piece 326 has a flange portion 326c. The distal end side face of the flange portion 326c of the movable tripping piece 326 distal end portion has a flat surface portion for gripping a needle, the flat surface of such flat surface portion being orthogonal as to the axis of the generally cylindrically-shaped movable gripping piece 326.

The distal end portion of the stainless steel fixed gripping piece 331 serving as another griping member is fixed to the distal end portion of the turning portion base member 325 by a stainless steel pin 330. The fixed gripping piece 331 is a cylindrical member having a flange portion 331a on the distal end portion thereof. The fixed gripping piece 331 and the turning portion base member 325 are fixed by the pin 330 which passes through the distal end portion of the turning portion base member 325 and the proximal end portion of the fixed gripping piece 331. The pin 330 is slidably fitted within the two slot portions 326a and 326b of the movable gripping piece 326. The pin 330 is fixed to the turning portion base member 325 at the end portion by laser welding.

The fixed gripping piece 331 serving as a gripping piece on the distal end portion is in a toric shape, and also has a flat surface portion parallel to the flat surface portion of the distal end portion of the movable gripping piece 326.

When the open/close button 305 on the operation portion 303 is not being operated, the spring 333 presses against the bottom portion of the movable gripping piece 326, but the distal end side face of the flange portion 326c of the movable gripping piece 326 is in contact with the proximal end side face of the flange portion 331a of the fixed gripping piece 331 and therefore cannot extend any further, thus remains in the state of compression. Accordingly, when the open/close button 305 of the operation portion 303 is not being operated, the flat surfaces of each of the movable gripping piece 326 and fixed gripping piece 331 are pressed together so as to adhere, thus can firmly grip the needle. Also, when the open/close button 305 is pressed, the movable gripping piece 326 is moved from the fixed griping piece 331 toward the proximal end side, thus the space between the respective flat surfaces can be separated so as to release or grip the needle gripped between the flat surfaces of each of the movable gripping piece 326 and fixed gripping piece 331.

Also, the flange portion 331a of the fixed gripping piece 331 and the flange portion 326c of the movable gripping piece 326 are formed to be thin, facilitating ease of making contact with the needle between each of the flat surface portions. Accordingly, regardless of the situation of the bending angle of the gripping portion 308 or the state of the body cavity wall, the surgeon can readily grip the needle.

Accordingly, as will be described later, the needle is gripped so as to be sandwiched between the flat surface portion of the fixed gripping piece 331 and the flat surface portion of the movable gripping piece 326, according to the opening/closing operation as to the open/close button 305. Accordingly, the spring 333 configures a portion of the pressing means to continually press, of at least one of the two gripping members in the direction to adhere to the other of the gripping members.

Each of the surfaces of the flat surface portion of the fixed gripping piece 331 and flat surface portion of the movable gripping piece 326 serving as gripping faces for gripping the needle have been subjected to slip-resistant processing. Electrical discharge processing, knurling, and spray processing of ultra-fine diamond particles to metallic plating are examples of slip-resistant processing.

Next, the operation of the treatment portion 304 of the needle driver 301 configured as described above will be described.

As described above, the round column portion on the proximal end side of the fixed gripping piece 331 is inserted in the hole portion of the movable gripping piece 326, and the round column portion is fixed to the turning portion base member 325, whereby the fixed gripping piece 331 has a positional relation which is fixed as to the turning portion base member 325. In other words, the fixed gripping piece 331 has a positional relation of being fixed in the longitudinal axial direction as to the bending portion base member 320 also.

On the other hand, upon the opening operation of the open/close button 305, i.e. when the open/close button 305 is pressed, the traction wire 314 is pulled according to the amount of the open/close button 305 being depressed, whereby the movable gripping piece 326 which is movable toward the operation portion 303 side, while resisting the force applied in the direction of the spring 333 expanding, moves toward the operation portion 303 side so that the flange portion 326c separates from the flange portion 331a of the fixed griping piece 331. Accordingly, upon the traction wire 314 being pulled, the movable gripping piece 326 is moved in the direction shown by the arrow in FIG. 7 by the amount of the traction wire 314 being pulled. That is to say, the movable gripping piece 326 resists the pressing force by the spring 333 in the direction of adhering to the fixed gripping piece 331, and moves in the direction of separating from the fixed gripping piece 331 positioned at the distal end portion of the treatment portion 304 by the opening operation of the open/close button 305. At this time, as shown in FIG. 9, the spring 333 is in a further compressed state than in the state wherein the opening operation of the open/close button 305 shown in FIG. 8 is not performed, whereby force to press back on the open/close button 305 is applied. When the opening operation is no longer performed, the traction wire 314 is pulled toward the treatment portion 304 side by the expansion force of the spring 333, by the pressing force in the direction of adhering the movable griping piece 326 to the fixed gripping piece 331. Consequently, with the gripping portion 308, the needle is gripped between the flat surface portion of the fixed gripping piece 331 and the flat surface portion of the movable gripping piece 326.

Next, the turning operation will be described.

In a state wherein a needle is gripped, or in a state wherein a needle is not gripped, upon the turning dial 307 being turned, the turning force transmitting pipe 313 serving as a shaft member turning on the axis, whereby the turning force transmitting coil 317 fixed to the turning force transmitting pipe 313 turns, and the turning portion base member 325 fixed to the turning force transmitting coil 317 also turns. The turning force transmitting pipe 313 turns according to the amount by which the turning dial 307 turns, thus the turning amount according to the amount of the turning dial 307 turning is transmitted to the treatment portion 304. Consequently, the fixed gripping piece 331 and the movable gripping piece 326 configuring the gripping portion 308 are linked to the turning of the turning portion base member 325 and turn along with the turning portion base member 325.

Also, at this time, the traction wire 314 is slidable as to the hole in the bottom portion of the turning portion base member 325, whereby even if the turning portion base member 325 turns, the traction wire 314 does not turn along with the turning portion base member 325.

Next the variable angle operation will be described.

The variable angle lever 306 is moved from the distal end side toward the proximal end side in the insertion axial direction, whereby the distal end portion including the treatment portion 304 bends, as shown in FIG. 14. Upon moving the variable angle lever 306 from the distal end side toward the proximal end side in the insertion axial direction, the bending force transmitting pipe 315 presses the joint member 318 toward the distal end side, and as a result, the joint member 318 presses against the linking member 319. The pressed linking member 319 further presses against the bending portion base member 320, but since the bending portion base member 320 is linked to the distal end housing member 312 by the pin 324, the bending portion base member 320 turns on the pin 324.

The bending force transmitting pipe 315 moves forward/backward according to the turning amount of the variable angle lever 306, whereby the bending amount of the treatment portion 304, i.e. the bending angle changes. Accordingly, as described above, the surgeon can set the treatment portion 304 to a desired angle as to the insertion portion 302 axis according to the situation of the surgery, and thus perform treatment.

Next, the operation portion 303 of the needle driver 301 according to the present embodiment will be described with reference to FIG. 16 through FIG. 25.

Figure 16:
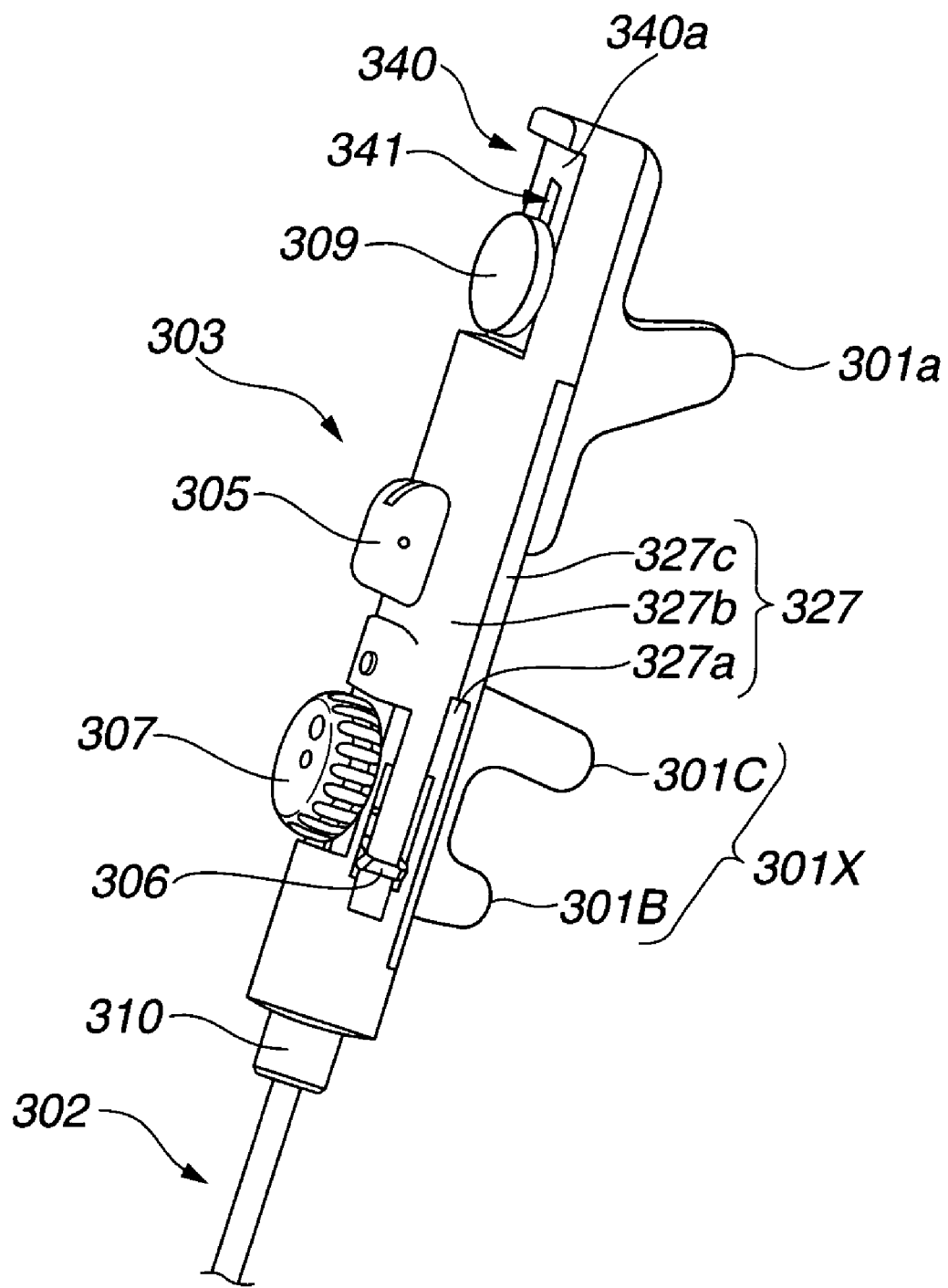
FIG. 16 is an external perspective view of the operation portion of the needle driver shown in FIG. 1, as seen from one side of the front diagonal direction.
Figure 17:
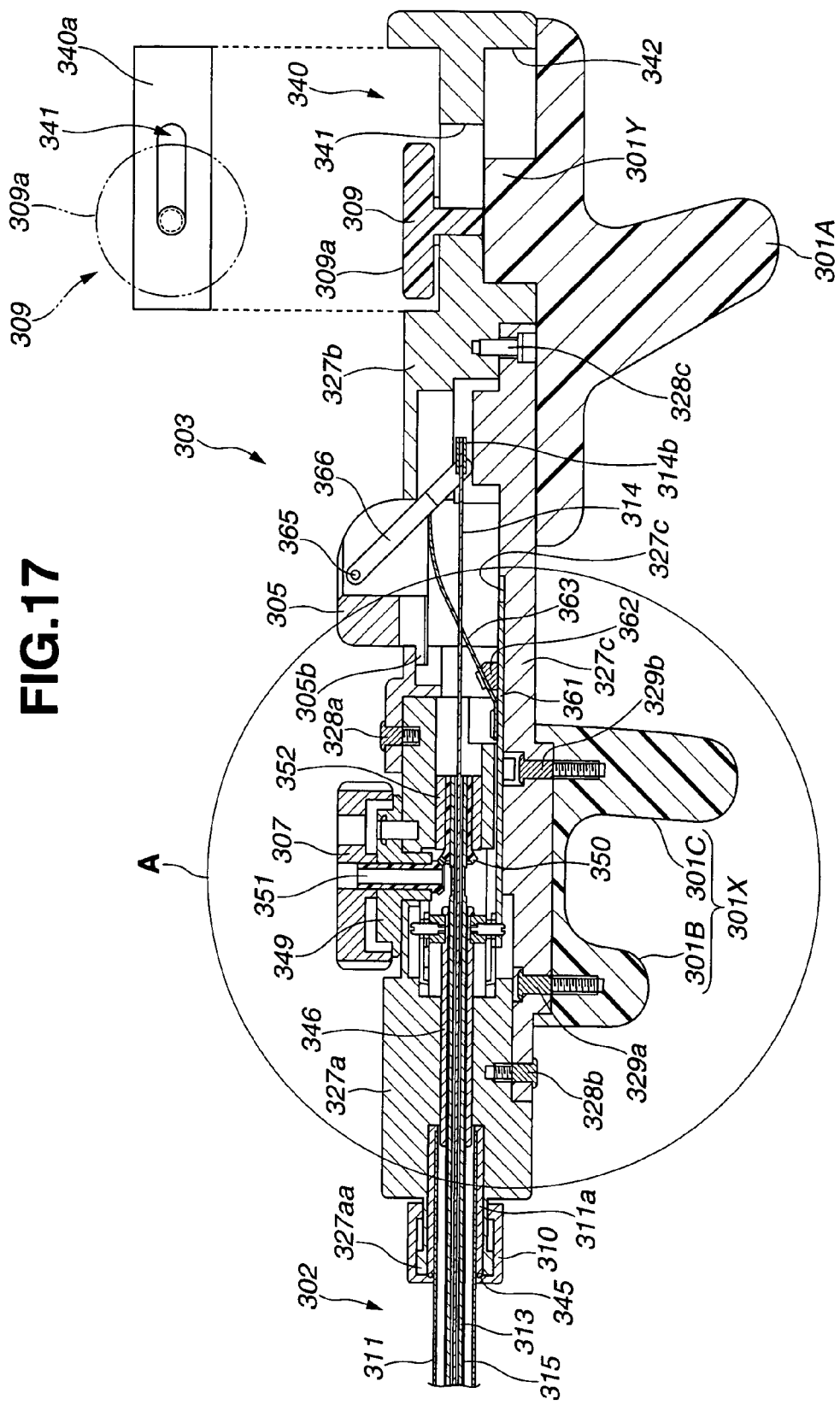
FIG. 17 is a cross-sectional view of the operation portion along the axial direction of the needle driver shown in FIG. 1.
Figure 18:
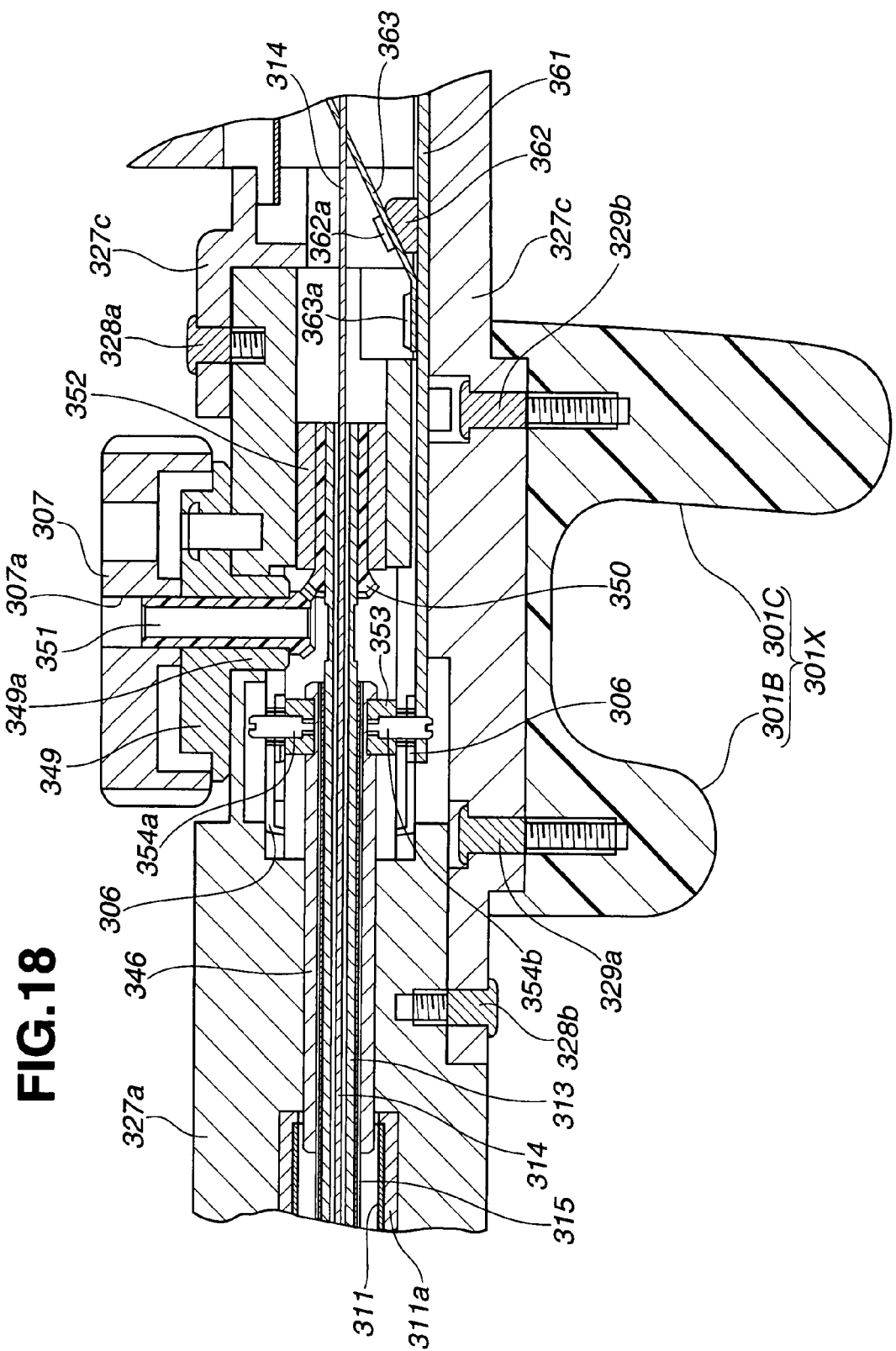
FIG. 18 is a cross-sectional view of the operation portion wherein the portion surrounded by a circle A in FIG. 17 is enlarged.
Figure 19:
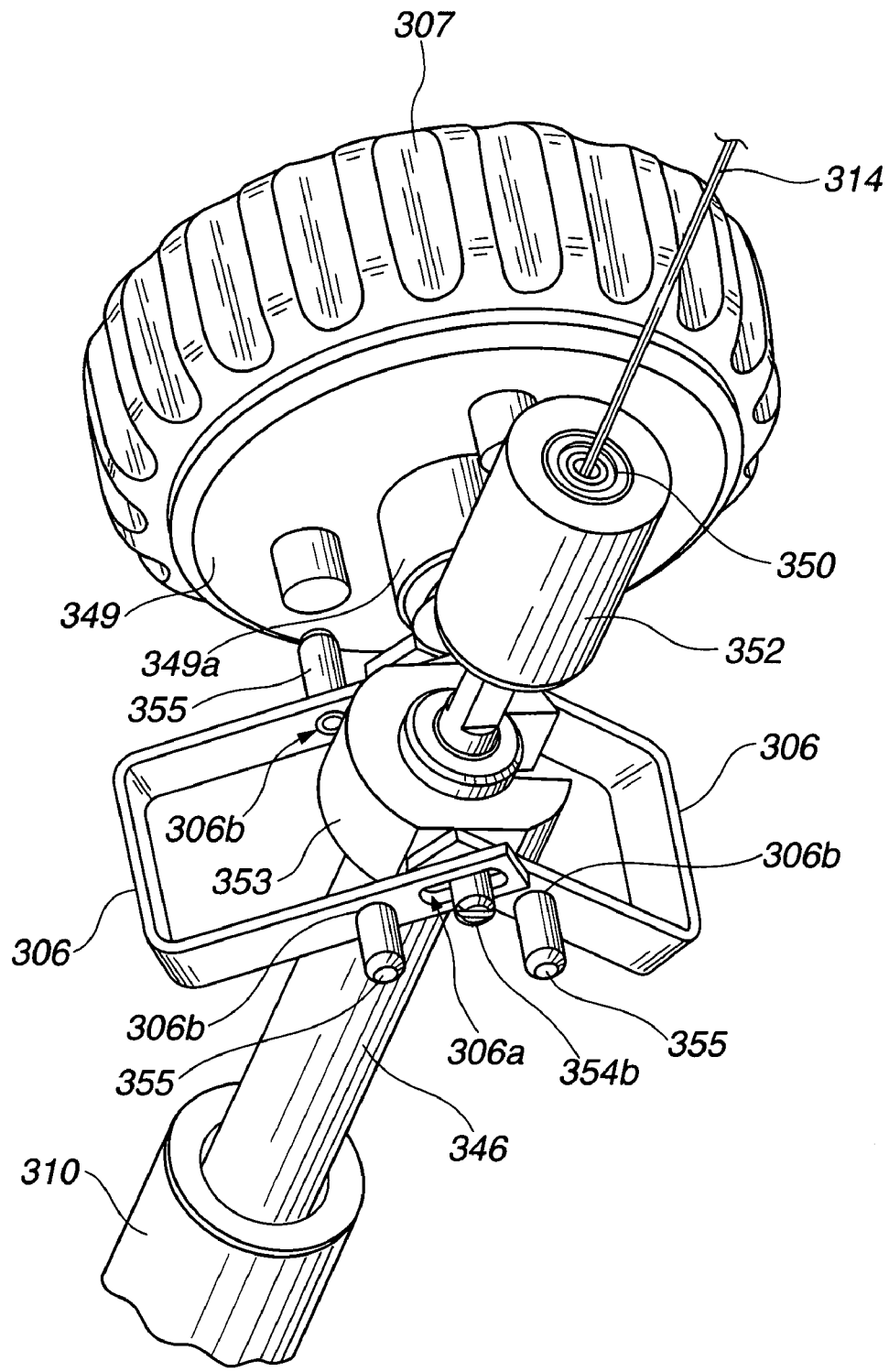
FIG. 19 is a perspective view showing the internal configuration of the operation portion provided in the periphery of a turning dial, wherein the exterior member of the operation portion of the needle driver shown in FIG. 1 is omitted.
Figure 20:
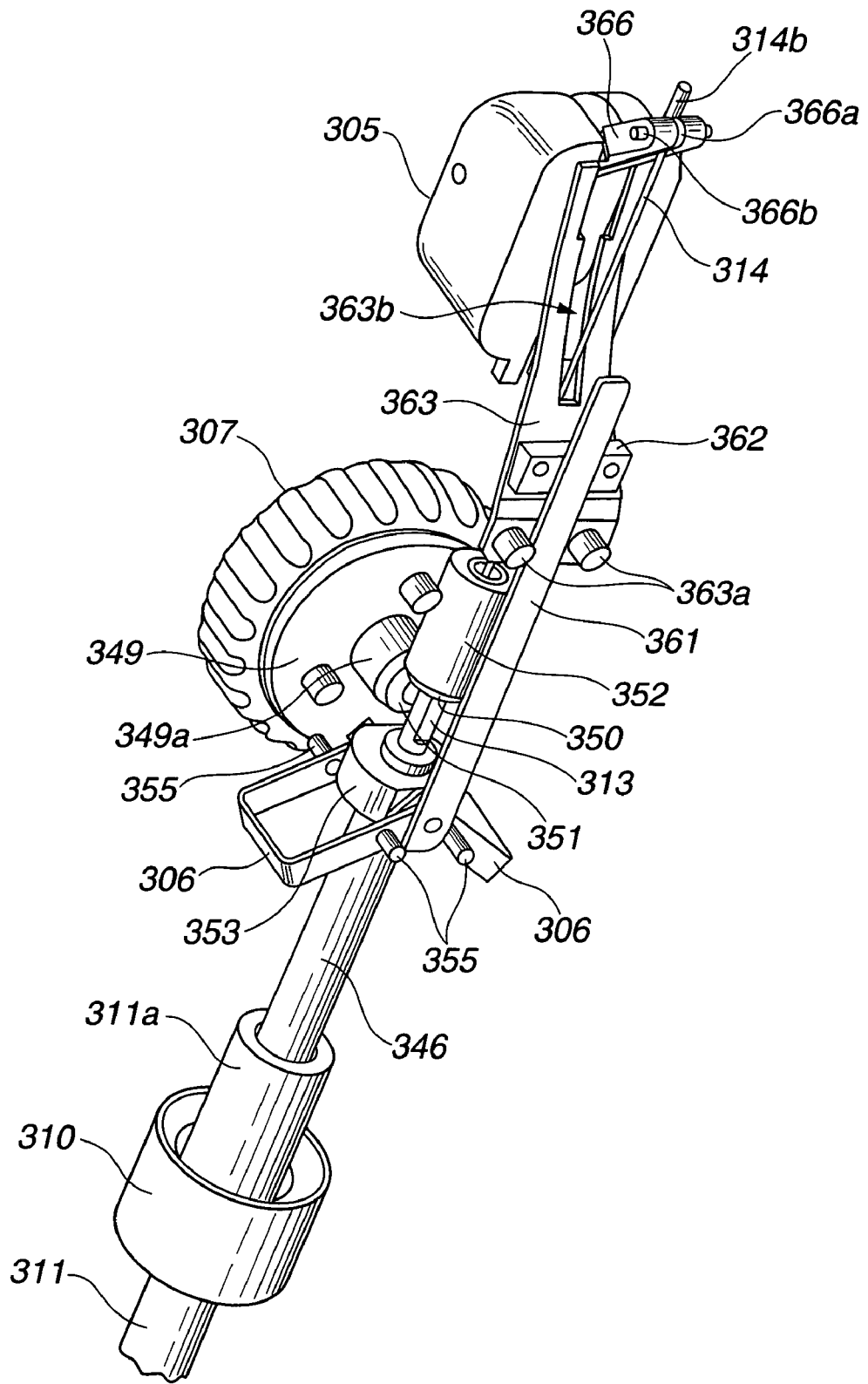
FIG. 20 is a perspective view of the various configuration members within the operation portion of the needle driver shown in FIG. 1, as seen from one lower diagonal side direction.
Figure 21:
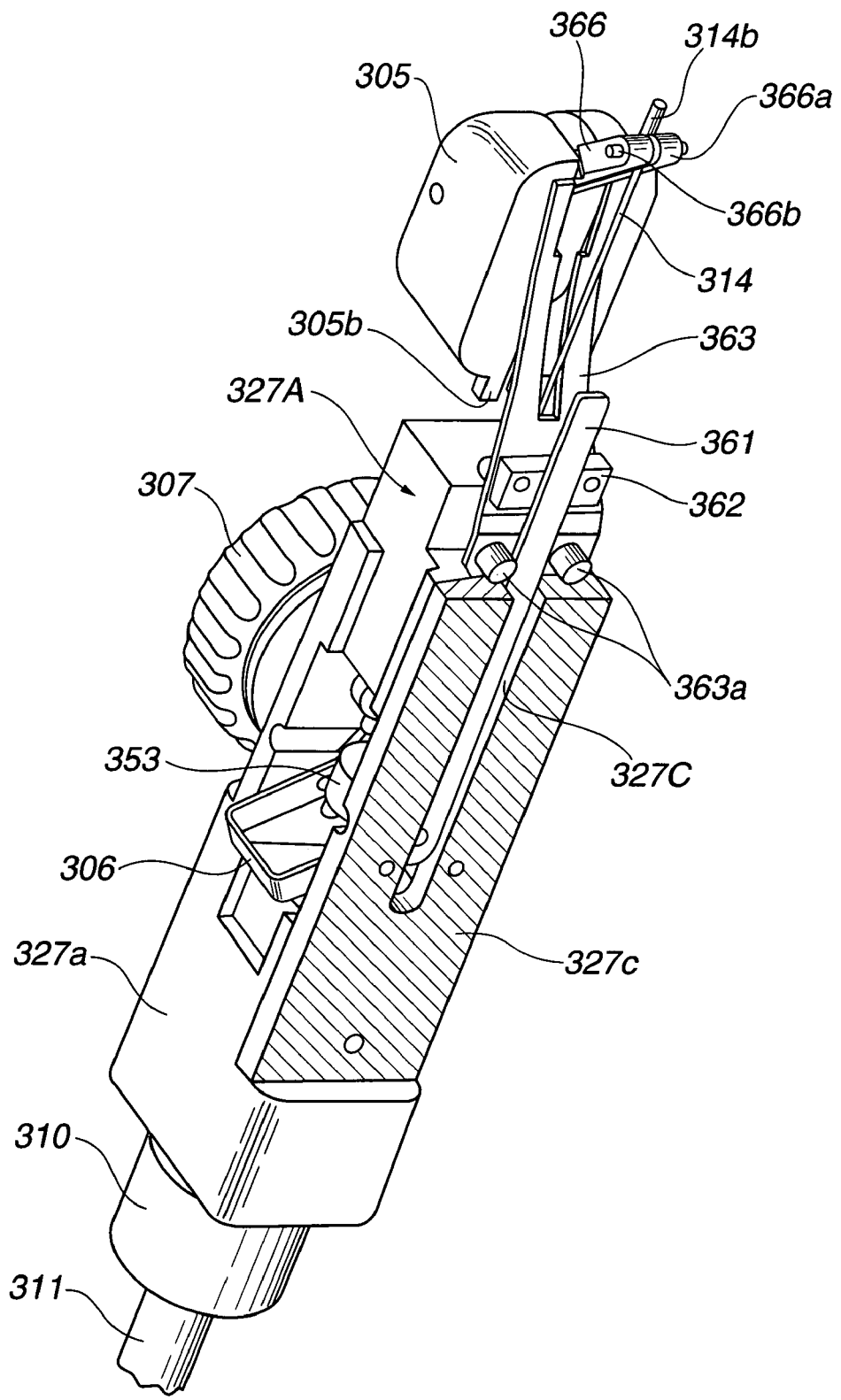
FIG. 21 is a perspective view showing a portion of the exterior member of the operation portion of the needle driver shown in FIG. 1, wherein the various configuration members within the operation portion are seen from one lower diagonal side direction.
Figure 22:
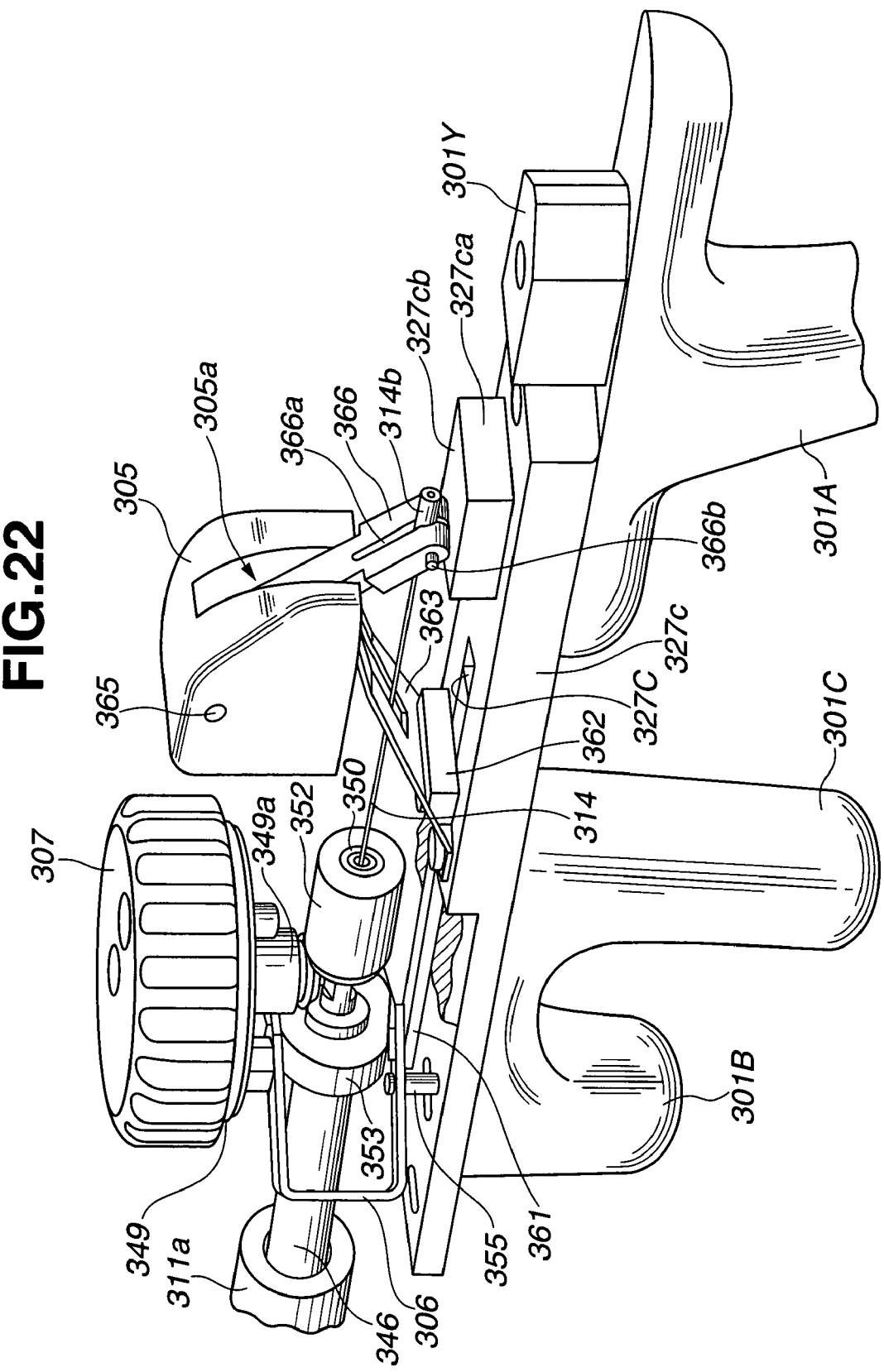
FIG. 22 is a perspective view showing a portion of the exterior member of the operation portion of the needle driver shown in FIG. 1, wherein the various configuration members within the operation portion are seen from one diagonal side direction on the proximal end side.
Figure 23:
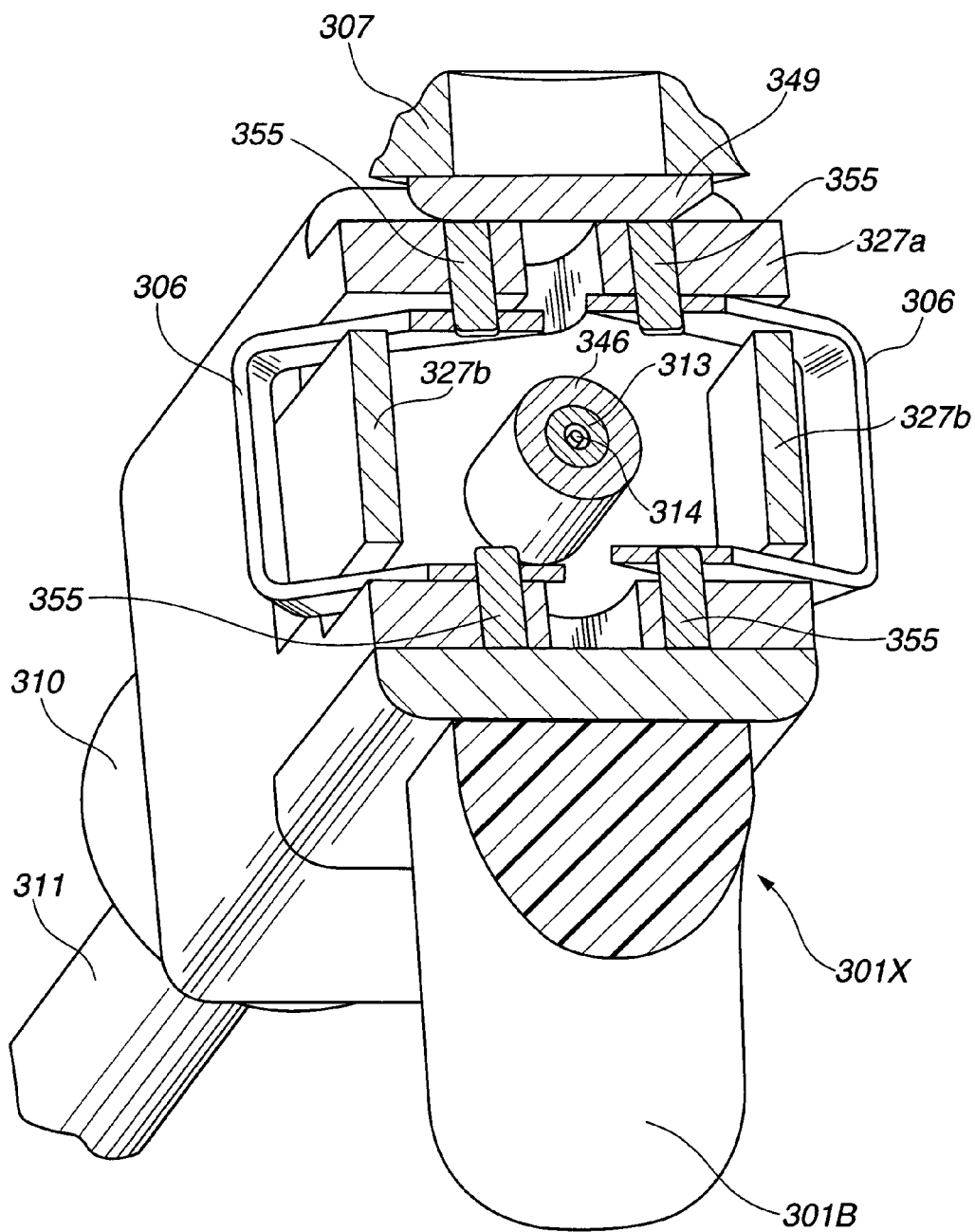
FIG. 23 is a cross-sectional view of the needle driver shown in FIG. 1 wherein a mid-section portion of the operation portion is dissected along the direction orthogonal as to the axis of the needle driver.
Figure 24:
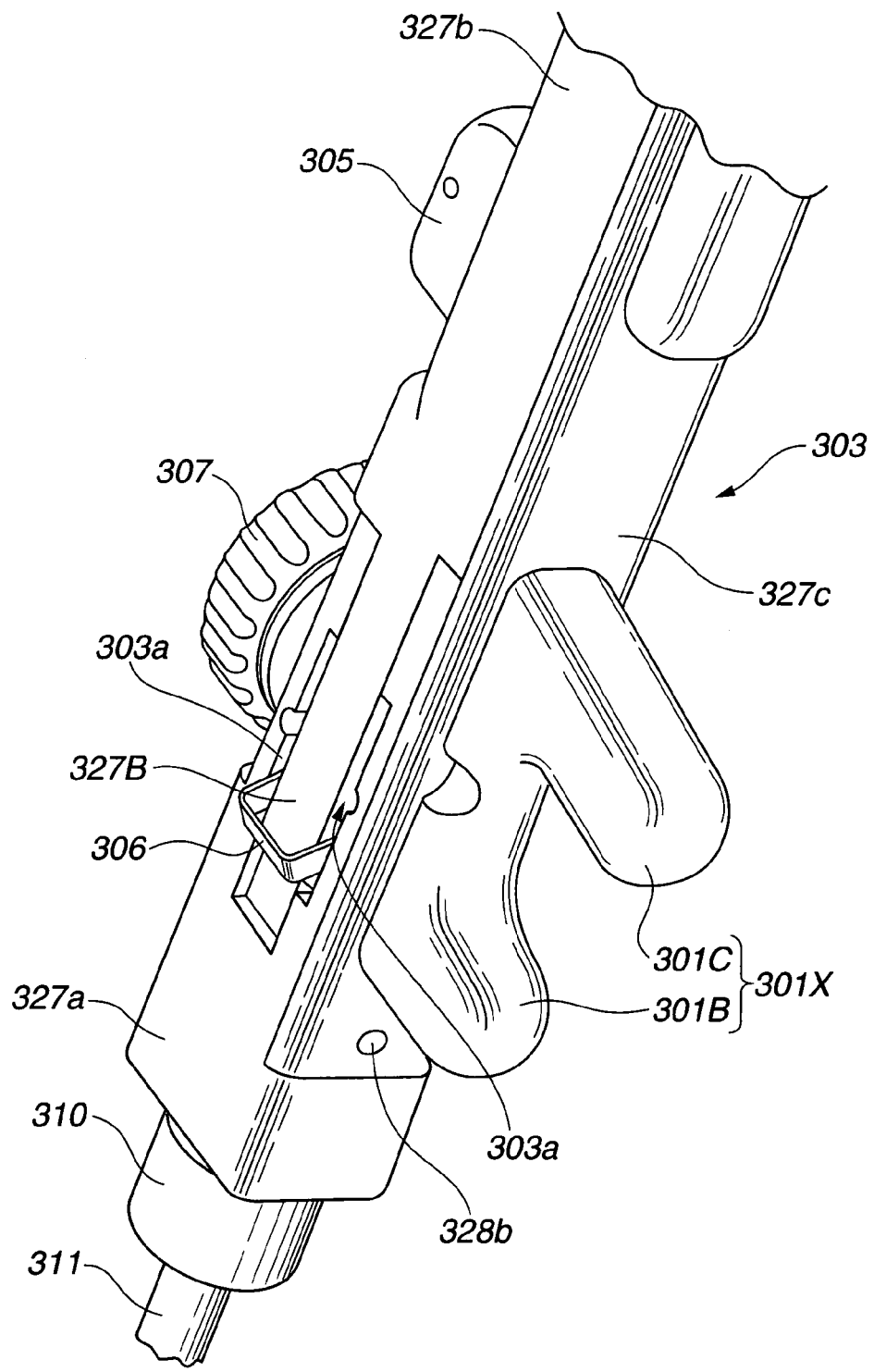
FIG. 24 is a perspective view of the operation portion of the needle driver shown in FIG. 1 as seen from one side diagonal side direction.
Figure 25:
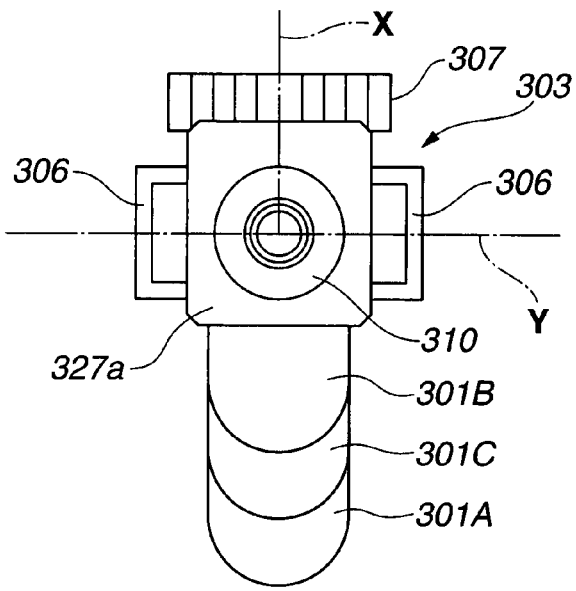
FIG. 25 is a front view of the needle driver shown in FIG. 1 as seen from the distal end side.

FIG. 16 is an external perspective view of the operation portion 303 of the needle driver 301, as seen from one side of the front diagonal direction. FIG. 17 is a cross-sectional view of the operation portion 303 along the axial direction of the needle driver 301, FIG. 18 is a cross-sectional view of the operation portion 303 wherein the portion surrounded by a circle A in FIG. 17 is enlarged, FIG. 19 is a perspective view showing the internal configuration of the operation portion 303 provided in the periphery of the turning dial 307, wherein the exterior member of the operation portion 303 is omitted, FIG. 20 is a perspective view of the various configuration members within the operation portion 303, as seen from one lower diagonal side direction, FIG. 21 is a perspective view showing a portion of the exterior member of the operation portion 303, wherein the various configuration members within the operation portion 303 are seen from one lower diagonal side direction, FIG. 22 is a perspective view showing a portion of the exterior member of the operation portion 303, wherein the various configuration members within the operation portion 303 are seen from one diagonal side direction on the proximal end side, FIG. 23 is a cross-sectional view of the needle driver 301 wherein a mid-section portion of the operation portion 303 is dissected along the direction orthogonal as to the axis of the needle driver 301, FIG. 24 is a perspective view of the operation portion 303 as seen from one side diagonal side direction, and FIG. 25 is a front view of the needle driver 301 as seen from the distal end side.

As shown in FIG. 16, the operation portion 303 is disposed on the same axis of the longitudinal axis of the insertion portion 302 at the proximal end side of the insertion portion 302, and is covered by an exterior member 327 having a generally rectangular shape. The exterior member 327 is integrally configured with three metal members such as aluminum or the like fitted together, and is provided with a distal end side exterior member 327a forming the exterior of the distal end side (the insertion portion 302 side), a main unit exterior member 327b wherein a turning dial 307 and open/close button 305 are disposed on one face thereof, and a cover exterior member 327c which has a finger holding member 301X disposed on one face thereof and is fitted on the side opposite the face wherein the turning dial 307 and open/close button 305 of the main unit exterior member 327b is provided.

The distal end side exterior member 327a and the main unit exterior member 327b are fixed to one another with a fixing screw 328a. Also, the cover exterior member 327c is fixed as to the distal end side exterior member 327a by the fixing screw 328b after the finger holding member 301X is fixed to one face thereof by two fixing screws 329a and 329b, whereby the cover exterior member 327c is fixed to the main unit exterior member 327b by the fixing screw 328c. Note that the exterior member 327 may also be made of resin.

Hole portions for the space wherein the mechanisms in the vicinity of a thruster 353 to be described later and variable angle lever 306 are to be disposed are formed on the distal end side exterior member 327a, and a recess-shaped step portion 327A is formed from the proximal end to partway towards the distal end side on both side faces (see FIG. 21. Note that with FIG. 21, only the step portion 327A on the one side face side of the distal end side exterior member 327a is shown.)

The main unit exterior member 327b has two arm portions 327B (see FIG. 24. Note that with FIG. 24, only the arm portion 327B of one side face side of the main unit exterior member 327b is shown) extending toward the distal end side on both side portions of the distal end side, and the two arm portions 327B are each fitted to the two step portions 327A of the distal end side exterior member 327a.

Also, in a state wherein the main unit exterior member 327b is attached to the distal end side exterior member 327a, a variable angle lever 306 protrudes from the respective side faces of the portion forming both side faces of the operation portion 303, and also a long groove 303a for performing tilting operations is formed (see FIG. 24). Two long grooves 303a are formed on one side face of the operation portion 303.

As shown in FIG. 17, the step portion 340 is formed on the proximal end portion of the main unit exterior member 327b. The step portion 340 has a seat portion 340a wherein a dial head portion 309a of an adjusting dial 309 formed of resin makes contact. An slot 341 is formed on the seat portion 340a along the longitudinal axial direction of the operation portion 303 in the generally center of the step portion 340. On the surface of the main unit exterior member 327b on the opposite side of the step portion 340, a groove portion 342 into which a protruding portion 301Y of the palm holding member 301A is inserted is formed along the longitudinal axial direction of the operation portion 303. The slot 341 is a hole for communicating the step portion 340 and the groove portion 342.

The adjusting dial 309 is inserted from the step portion 340 side, a screw portion of the adjusting dial 9 is screwed into a female screw hole on the protruding portion 301Y where a female screw is formed, whereby the screw portion of the adjusting dial 309 fixes the palm holding member 301A to the adjusting dial 309, and also the palm holding member 301A is fixed to the main unit exterior member 327b. In the event of such fixing, the position of the palm holding member 301A in the longitudinal axial direction of the main unit exterior member 327b can be adjusted according to the size of the hand of the surgeon, by adjusting the position of the adjusting dial 309 within the slot 341 in the longitudinal axial direction of the main unit exterior member 327b.

Note that the dial head portion 309a of the adjusting dial 309 has an external diameter longer than the length of the width direction of the operation portion 303, so as to protrude from both side faces of the operation portion 303, in order to facilitate grasping of the external periphery portion.

Also, the distal end side exterior member 327a has a tube-shaped linking portion 327aa which is formed so as to protrude in the distal end side. A hole portion communicating with the opening portion on the distal end side of the tube-shaped linking portion 327aa is formed on the distal end side exterior member 327a. The hole portion has a step portion partway toward the proximal end side from the distal end side. A screw groove is cut on the outer circumferential surface of the linking portion 327aa.

A restraining ring 310 in a generally ring shape having a screw groove cut on the inner circumferential surface is provided so as to be covered by the linking portion 327aa. The restraining ring 310 made of aluminum has an opening portion on the distal end side thereof. The proximal end portion of the sheath 311 on the insertion portion 302 is inserted in the distal end side exterior member 327a so as to pass through the opening portion of the restraining ring 310 and the opening portion of the linking portion 327aa, and also the restraining ring 310 is fixed to the linking portion 327aa by the screw groove on the inner circumferential surface and the screw groove on the outer circumferential surface of the linking member 327aa being screwed together.

To describe in detail, the sheath 311 is adhered to a generally tube-shaped sheath end member 311a on the outer circumference of the proximal end portion, and the sheath 311 is inserted in the hole portion of the distal end side exterior member 327a along with the sheath end member 311a, so as to be slidable around the axis of the sheath end member 311a and to be turnable. The sheath end member 311a is made of aluminum. Also, the surface to serve as the distal end side of the restraining ring 310 has a hole portion (opening portion) having substantially the same hole diameter as the outer diameter of the sheath 311 formed thereupon. This is to say, the surface on the distal end side of the restraining ring 310 forms the inner-facing flange, and by the sheath end member 311a of the sheath 311 making contact with the inner-facing flange, the sheath 311 which forms the exterior of the insertion portion 302 is prevented from being pulled out from the distal end side exterior member 327a.

The restraining ring 310 moves toward the proximal end side as the screw amount with the linking portion 327aa increases. Note that between the restraining ring 310 and the sheath end member 311a, an O-ring 345 made of silicone is provided. Thus, the inner-facing flange face of the restraining ring 310 presses the sheath end member 311a of the sheath 311 toward the proximal end side, via the O-ring 345.

The proximal end face of the sheath end member 311a which is adhered to the proximal end portion of the sheath 311 makes contact with the distal end face of the step portion formed at the hole portion of the distal end side exterior member 327a by elastic force of the O-ring 345. Consequently, the insertion portion 302 is firmly fixed to the operation portion 303 without instability.

Further, the O-ring 345 presses the sheath end member 311a with a predetermined pressing force to an extent that the insertion portion 302 is firmly fixed to the operation portion 303, and the insertion portion 302 is turnable around the axis of the insertion portion 302 as to the operation portion 303. This is realized by setting the distance between the sheath end member 311a when the distal end inner surface of the restraining ring 310 makes contact with the distal end portion of the linking portion 327aa and the distal end inner surface of the restraining ring 310 as a distance so as to generate predetermined pressure force by the O-ring 345 being compressed.

On the turning force transmitting pipe 313 through which the traction wire 314 is inserted, a slave side bevel gear member 350 formed of a synthetic resin such as polyacetal is adhered to the proximal end portion and fixed thereto. Note that the turning force transmitting pipe 313 is pressed into the hole portion formed in the longitudinal direction of the slave side bevel gear member 350 so that the cross-section center in the direction orthogonal to the longitudinal direction axis of the turning force transmitting pipe 313 and the turning axis of the slave side bevel gear member 350 overlap with one another, and is fixed thereto.

The end portion having a gear of the slave side bevel gear member 350 faces the distal end side, and an axis portion is turnably supported around the axis of the generally tube-shaped bearing 352. Note that the bearing 352 made of aluminum or resin is fitted into the distal end side exterior member 327a and fixed thereto.

Also, a turning dial 307 is disposed on the step portion formed on one face of the distal end side exterior member 327a. A generally round plate shaped bearing plate 349 is provided on the surface on the operation portion 303 side of the turning dial 307 made of aluminum or resin. The bearing plate 349 is fixed to the distal end side exterior member 327a. A wheel shaft 349a protrudes from the central portion of the surface on the opposite side of the surface of the turning dial 307 side of the bearing plate 349 made of aluminum or resin. The bearing plate 349 has a hole portion formed therein through the axis center of the wheel shaft 349a from the center of the face of the turning dial 307 side.

An active side bevel gear member 351 formed of a synthetic resin such as a polyacetal is inserted through the bearing plate 349 hole portion so as to be turnable around the axis of the active side bevel gear member 351. Also, the end portion on the opposite side of the side having the gear of the active side bevel gear member 351 is fitted into a portion of the hole portion 307a formed at the turning axis center of the turning dial 307 and is fixed thereto. In other words, the turning dial 307 and the active side bevel gear member 351 are integrated.

Also, the bearing plate 349 is provided so that the gear of the active side bevel gear member 351 engages with the gear of the slave side bevel gear member 350.

Accordingly, when the surgeon turns the turning dial 307 to a predetermined direction, the turning thereof is transmitted to the active side bevel gear member 351, and by the engaging action thereof the turning force thereof is transmitted to the slave side bevel gear member 350. That is to say, upon the turning dial 307 being operated to turn around the axis which is orthogonal to the longitudinal direction of the operation portion 303, the turning force is transmitted around the axis of the longitudinal direction of the turning force transmitting pipe 313 by the slave side bevel gear member 350 via the active side bevel gear member 351. Consequently, the turning force transmitting pipe 313 transmits the turning force to the turning force transmitting coil 317 (see FIG. 9) wherein the turning force transmitting pipe 313 is fixed to the distal end thereof, and the gripping portion 308 (see FIG. 1) is turned.

The bearing plate 349 described above also serves as a function of a protective plate for preventing wearing deterioration between the turning dial 307 and the distal end side exterior member 327a due to friction occurring along with the turning. Also, the external periphery portion of the turning dial 307, protrudes farther than both side faces of the operation portion 303, as described above. Therefore, there may be instances wherein, due to the handling of the turning dial 307 by the surgeon or nurse, a force to pull out the turning dial 307 from the end portion on the opposite side of the side having the gear of the active side bevel gear member 351 may be applied. As a measure against this, the bearing plate 349 is provided to the side face of the turning dial 307, preventing great force from pulling out the turning dial 307 from the active side bevel gear member 351.

That is to say, the outer diameter of the bearing plate 349 is slightly smaller than the turning dial 307. Thus operability of the index finger of the surgeon operating to turn the turning dial 307 is not lost, thus preventing great force in the direction of pulling out the turning dial 307, i.e., the direction away from the distal end side exterior member 327a, from being applied.

As shown in FIG. 18, a generally tube-shaped stopping pipe 346 which is configured to be slidable in the longitudinal axial direction is adhered to the bending force transmitting pipe 315 wherein the turning force transmitting pipe 313 is inserted so as to be turnable around the longitudinal axis, as to the distal end side exterior member 327a to the proximal end portion. The stopping pipe 346 made of aluminum is moved forward/backward in the longitudinal axial direction along with the bending force transmitting pipe 315 by the operation of the variable angle lever 306.

Also, as shown in FIG. 18 and FIG. 19, a thruster 353 made of metal such as stainless steel is fitted into the proximal end portion of the stopping pipe 346 and fixed thereto. Two screw holes are cut on the same axis from the external periphery side on the thruster 353, wherein screw pins 354a and 354b made of metal such as stainless steel are screwed into the two screw holes.

Specifically, the thruster 353 is cut so as to have a surface parallel to both end portions on the outer periphery side of the generally round column shaped member, and two screw holes are formed in the direction toward the inner side from each cut face, so as to be orthogonal as to the respective cut faces. Screw pins 354a and 354b are each screwed into the two screw holes and are provided such that an end portion of each of the screw pins 354a and 354b protrude.

Note that the two hole portions wherein the respective screw pins 354a and 354b are screwed in are formed on the thruster 353 so that each hole axis is on the same axis. This is to say, the two screw pins 354a and 354b have each longitudinal axis along the same axis, and protrude in the outer periphery direction of the thruster 353 in a position symmetrical at both end portions of the outer periphery side of the thruster 353. Note that the two screw pins 354a and 354b have a groove formed on each screw head to enable fastening with a flat-head screwdriver.

Also, a notched portion is formed on the thruster 353, facing the center from the outer periphery portion on one directional side which is orthogonal to the axis of the two screw pins 354a and 354b, and is also orthogonal to the longitudinal axis of the stopping pipe 346. The notched portion of the thruster 353 has two flat surface portions which are parallel and face one another.

The stopping pipe 346 has a peripheral groove formed on the outer periphery of the proximal end portion, wherein the peripheral groove is formed by a shaping processing so as to have flat surface corresponding to each of two parallel flat surfaces of the portion notched on the thruster 353. Thus, the thruster 353 is fit into the peripheral groove of the stopping pipe 346 from the outer periphery direction of the notched portion so that the two faces of the notched portions and the periphery groove of the stopping pipe 346 each come into contact with one another.

Thus, the thruster 353 is fit into the stopping pipe 346 so that the axis of the two screw pins 354a and 354b are orthogonal to the longitudinal axis of the stopping pipe 346.

The variable angle lever 306 is a member wherein a plate member made from metal, whereupon an slot 306a is bored on each end portion, is formed in a horseshoe shape. A hole portion 306b (see FIG. 19) is bored on two arm portions of the horseshoe shaped variable angle lever 306, wherein a pivot pin 355 to be described later in the vicinity of the slots 306a is inserted into the hole portion 306b. In other words, two slots 306a and two hole portions 306b are provided on the variable angle lever 306.

Also, with the variable angle lever 306, the two slots 306a and the two hole portions 306b are each positioned and bored on the portion having a surface facing the horseshoe shaped arm portion so that the center of the two slots 306a each pass through the same axis, and also the center of the two hole portions 306b each pass through the same axis.

Further, each slot 306a and each hole portion 306b are positioned so as to have an axis orthogonal as to the surface facing the axis wherein each center passes through. Note that with the needle driver 301 according to the present invention, as shown in FIG. 25, the two variable angle levers 306 as described above are provided so as to protrude from both side faces of the operation portion 303.

The two screw pins 354a and 354b of the thruster 353 are inserted into each slot 306a of the two variable angle levers 306, so as to be slidably turnable around the axis of the screw pins 354a and 354b, as shown in FIG. 19. Also, the two variable angle levers 306 are disposed in a position symmetrical to each other on the longitudinal axis of the stopping pipe 346 and the longitudinal axis of the two screw pins 354a and 354b, sandwiching the thruster 353 therebetween.

The arm portions of the two variable angle levers 306 overlap each other so as to be staggered in the vicinity of the screw pins 354a and 354b, in a state of being provided on the thruster 353. That is to say, in the event that the portion having an slot 306a wherein the screw pin 354a is inserted on one of the variable levers 306 is on the thruster 353 side, the other variable angle lever 306 has the portion having the slot 306a wherein the screw pin 354b is on the thruster 353 side.

Also, a pivot pin 355 is inserted into each of the hole portions 306b of the two variable angle levers 306 from the outer side direction. That is to say, with the present embodiment, respective pivot pins 355 is inserted into the two hole portions 306b of each variable angle lever 306 so as to be slidably turnable around the axis of each pivot pin 355, thereby on the operation portion 303 provided with the two variable angle levers 306, a total of four pivot pins 355 are provided.

These four pivot pins 355 are each pressed into the distal end side exterior member 327a and fixed thereto (see FIG. 23). Also, the two pivot pins 355 inserted into the two hole portions 306b of the one variable angle lever 306 are pressed into and face the distal end side exterior member 327a, so that the longitudinal axis will be on the same axis, and are fixed thereto. Accordingly, the two variable angle levers 306 are each turnable around the axis of each pivot pin 355 corresponding to each hole portion 306b.

With the configuration described above, the two variable angle levers 306 are operated to turn around the axis of the pivot pins 355, thereby enabling the stopping pipe 346 to move forward/backward in the longitudinal axial direction via the thruster 353. Thus, the bending force transmitting pipe 315 is linked to the forward/backward movement of the stopping pipe 346 and thus moves forward/backward in the longitudinal axial direction.

The joint member 318 provided on the distal end portion of the bending force transmitting pipe 315 pushes the linking member 319 to advance toward the distal end side or pulls toward the proximal end side, along with the forward/backward movement in the longitudinal axial direction of the bending force transmitting pipe 315. Also, by the linking member 319 pressing the bending portion base member 320 toward the distal end side or pulling toward the proximal end side, the bending portion base member 320 turns on the pin 324 as the center of turning. Thus, the treatment portion 304 is subjected to bending operations within the range of 90 degrees as to the axis of the insertion portion 302.

Also, as shown in FIG. 25, when the needle driver 301 according to the present embodiment is seen from the distal end side, the two variable angle levers 306 are provided so as to protrude from both side faces of the operation portion 303.

To describe in further detail, the central portions of each of the two horseshoe shaped variable angle levers 306 link the turning dial 307 of the operation portion 303 provided on the upper side when viewing the diagram of FIG. 25, and a palm holding member 301A and finger holding members 301B and 301C of the operation portion 303 provided on the lower portion when viewing the diagram of FIG. 25, and also are generally orthogonal as to the vertical axis X passing through the center of the operation portion 303, and also protrude in the direction to be distanced from the operation portion 303, from both side faces of the operation portion 303 on which the horizontal axis Y passing through the center of the operation portion 303 intersects toward the horizontal axis Y direction.

Thus, by operating either one of the variable angle levers 306, the surgeon can perform bending operations of the treatment portion 304 in the range of 90 degrees as to the axis of the insertion portion 302. That is to say, by providing one variable angle lever 306 on both side faces of the operation portion 303, the needle driver 301 according to the present embodiment facilitates bending the treatment portion 304 as to the axis of the insertion portion 302 irrespective of whether the surgeon is right-handed or left-handed. The actions of the forward/backward movement of the bending force transmitting pipe 315, the stopping pipe 346 and so forth resulting from the operation of the variable angle lever 306 will be described in detail later.

Note that the mechanism in the vicinity of the thruster 353 fitted into the stopping pipe 346 and two variable angle levers 306 provided thereto is disposed in the interior space formed by the distal end side exterior member 327a, the main unit exterior member 327b and the cover exterior member 327c.

Also, as shown in FIG. 20, a brake bar 361 serving as a braked member made from a metal plate such as stainless steel is provided on one of the screw pins 354b of the thruster 353, whereby one end portion overlaps with the portion having the slot 306a of the two variable angle levers 306 and the other end extends toward the proximal end side. A hole portion is formed on the one end portion of the brake bar, wherein the screw pin 354b is inserted.

The brake bar 361 is provided within the groove portion 327C formed on one face of the cover exterior member 327c on the interior side of the operation portion 303, whereby the brake bar 361 is guided in a straight manner, and the midpoint portion thereof is sandwiched by the distal end side exterior member 327a and cover exterior member 327c so as to be subjected to predetermined frictional force. With this frictional force, a certain amount of turning force is needed in the event of turning the variable angle lever 306. Therefore, the surgeon can maintain a state of the treatment portion 304 being bent at a predetermined angle as to the axis of the insertion portion 302, by operating the variable angle lever 306.

Note that the groove portion 327C is formed on the distal end side exterior member 327a so as to have generally the same length in the longitudinal axial direction as the forward/backward movement amount of the stopping pipe 346 and bending force transmitting pipe 315, which move in the longitudinal axial direction, by the turning of the two variable angle levers 306.

Also, at a midway portion on the one face of the cover exterior member 327c, one end portion of a plate spring 363 pressing the open/close button 305 in one direction is fixed by two pins 363a. Note that the brake bar 361 is inserted between the plate spring 363 and the cover exterior member 327c, passes between the two pins 363a which fix the plate spring 363 and is held so as to be entirely buried in the groove portion 327C of the cover exterior member 327c, as shown in FIG. 20.

The stainless steel plate spring 363 has a notched portion 363b formed in a generally rectangular shape from the proximal end to a midway portion, and the proximal end portion serving as the other end portion is in contact with the back face of the proximal end side of the open/close button 305. The traction wire 314 is inserted through the notched portion 363b of the plate spring 363. Note that a wire pullout preventing member 314b made of stainless steel is provided at the proximal end portion of the traction wire 314.

At a midway portion of the plate spring 363, a brake shoe 362 serving as braking means formed of a metal such as stainless steel is provided on the surface side facing the cover exterior member 327c and the brake bar 361. Upon the open/close button 305 being pressed toward the inner side of the operation portion 303, the brake shoe 362 is pressed toward the brake bar 361 side in accordance with the force moving toward the cover exterior member 327c side received by the plate spring 363. Thus, the pressure applied to the brake bar 361 greatly increases on both side faces each in contact with the brake shoe 362 and the groove portion of the cover exterior member 327c, thus subjected to great frictional force. Accordingly, the brake bar 361 is regulated so as to prevent movement in the longitudinal axial direction.

As a result, by the movement of the brake bar 361 being regulated, turning of the variable angle lever 306, and the forward/backward movement in the longitudinal axial direction of the thruster 353, stopping pipe 346, and bending force transmitting pipe 315 also cannot be performed, whereby when the open/close button 305 is pressed in toward the inner side of the operation portion 303, a state wherein the treatment portion 304 is bent in a predetermined angle as to the axis of the insertion portion 302 can be securely maintained.

Also, the open/close button 305 is a block unit in a generally quadrangular column shape made of a metal such as aluminum or a resin having a guide groove 305a formed as a notch, along the surface in contact with one end portion of the plate spring 363 from the proximal end portion, as shown in FIG. 22. One end portion of a metallic pull link 366 is inserted into the guide groove 305a of the open/close button 305. Also, a pin 365 turnably holding the pull link 366 is provided on the open/close button 305 in the direction orthogonal to the axial direction of the guide groove 305a. Also, as shown in FIG. 17, the open/close button 305 has two protruding portions 305b protruding toward the distal end side on the distal end portion of the surface side wherein one end portion of the plate spring 363 is in contact.

The open/close button 305 is fitted into the hole portion provided on the main unit exterior member 327b from the face side of the main unit exterior member 327b serving as the inner side of the operation portion 303. At this time, by the two protruding portions 305b making contact with one face of the main unit exterior member 327b, the open/close button 305 is prevented from pulling out from the operation portion 303.

Also, the open/close button 305 is movable forward/backward in the direction orthogonal to the longitudinal axis of the operation portion 303 within the inner space of the operation portion 303 formed with the main unit exterior member 327b and cover exterior member 327c, and normally is pressed by the plate spring 363 in the outer surface direction of the main unit exterior member 327b, i.e. so that the two protruding portions 305b make contact with one face of the main unit exterior member 327b.

The pull link 366 wherein one end portion thereof is turnably supported by the pin 365 on the open/close button 305 has a groove portion 366a formed on the other end portion, and the groove portion 366a grips the wire pullout preventing member 314b of the traction wire 314. Also, a pin 366b for preventing the traction wire 314 from pulling out of the groove portion 366a is provided on the other end portion of the pull link 366.

As shown in FIG. 22, the cover exterior member 327c has a guide protruding portion 327ca protruding from the face of the proximal end portion on the side forming the inner space of the operation portion 303. The guide protruding portion 327ca has a flat surface portion 327cb on the protruding side, whereby the other end portion of the pull link 366 makes contact with the flat surface portion 327cb.

The pull link 366 which turns by the surgeon pressing the open/close button 305 is guided straight along the surface of the flat surface portion 327cb on the guide protruding portion 327ca, and the other end portion slides toward the proximal end side on the surface of the flat surface portion 327cb. At this time, the traction wire 314 is pulled along the longitudinal axis thereof toward the proximal end side without much shifting.

That is to say, the protruding amount of the guide protruding portion 327ca on the cover exterior member 327c, the length of the pull link 366, and the disposal position of the wire pullout preventing member 314b of the traction wire 314 gripped by the other end portion of the pull link 366 are set so as to each respond so that the traction wire 314 is pulled or loosened toward the proximal end side or the distal end side, without shifting, by the button operation of the open/close button 305.

Thus, upon the surgeon pushing the open/close button 305 towards the inner side of the operation portion 303, and thus the traction wire 314 being pulled toward the proximal end side along the longitudinal axial direction by the linked pull link 366, the movable gripping piece 326 (see FIG. 14) wherein the terminal enlarged portion 314a of the traction wire 214 fixed to the inner side of the bottom portion thereof is moved toward the proximal end side. Thus, the distal end side face of the flange portion 326c of the movable gripping piece 326 is distanced from the proximal end side face of the flange portion 331a of the fixed gripping piece 331.

Also, upon the surgeon releasing the pressing of the open/close button 305 toward the inner side of the operation portion 303, the open/close button 305 receives pressing force from the plate spring 363 and moves to the outer side of the operation portion 303. At this time, the spring 333 within the turning portion base member 325 presses the bottom portion of the movable gripping piece 326, and the distal end side face of the flange portion 326c of the movable gripping piece 326 extends to make contact with the proximal side face of the flange portion 331a of the fixed gripping piece 331. Accordingly, when the open/close button 305 of the operation portion 303 is not in operation, the respective flat surfaces of the movable gripping piece 326 and the fixed gripping piece 331 are pressed together so as to be adhered.

As a result of the above, the movable gripping piece 326 is moved from the fixed gripping piece 331 toward the proximal end side by the open/close button 305 being pushed to operate, or not being operated, thus a needle gripped between the flat surfaces of the movable gripping piece 326 and fixed gripping piece 331 can be released or the needle gripped by separating the flat surfaces and so forth.

Also, upon the open/close button 305 being pressed and the traction wire 314 pulled toward the proximal end side, based on such pulling force, a force is generated wherein the traction wire 314 attempts to become in a straight line. Therefore, in a state of the treatment portion 304 being in a predetermined bent angle as to the axis of the insertion portion 302, upon the open/close button 305 being pressed, the treatment portion 304 through which the traction wire 314 is inserted receives the force of the traction wire 314 attempting to become in a straight line, and becomes unable to maintain the predetermined bent angle as to the axis of the insertion portion 302. That is to say, the surgeon is unable to maintain the treatment portion 304 in the desired bent state as to the insertion portion 302, resulting in difficulty in suture operations.

Thus, the needle driver 301 according to the present embodiment is configured such that, upon the open/close button 305 being pressed, the brake shoe 362 presses against the brake bar 361 to stop the movement of the brake bar 361, and the treatment portion 304 can be maintained in a state of a predetermined bent angle as to the axis of the insertion portion 302, in a sure manner. As a result, the surgeon can maintain the desired bent state of the treatment portion 304 as to the insertion portion 302, and suture operations can be performed readily. The operation by the brake shoe 362 to stop the movement of the brake bar 361 will be further described in detail later.

Note that as described above, the end portion having the gear on the slave side bevel gear member 350 faces the distal end side. The insertion portion 302 is turnable around the axis of the insertion portion 302 as to the operation portion 303. Accordingly, when the surgeon views the operation portion 303 from the turning dial 307 side, when the extending direction of the treatment portion 304 as to the insertion axis of the insertion portion 302 is the same direction as the eyes of the viewing surgeon, the turning direction of the turning dial 307 (i.e. turning right or turning left from the viewpoint of the surgeon) becomes the same direction as the turning direction of the treatment portion 304. When the insertion portion 302 being turned around the axis of the insertion portion 302 as to the operation portion 303 and the surgeon views the operation portion 303 from the turning dial 307 side, if the extending direction of the treatment portion 304 as to the insertion axis of the insertion portion 302 is in the same line-of-sight direction of the surgeon, the turning direction of the turning dial 307 becomes the inverse direction as the turning direction of the treatment portion 304.

At the time of suturing, situations employing the needle driver 301 and forceps are frequent. In such cases, when the surgeon views the operation portion 303 from the turning dial 307 side, the extending direction of the treatment portion 304 as to the insertion axis of the insertion portion 302 is the same direction of the eyes of the viewing surgeon, so the operability of the turning operation of the treatment portion 304 of the needle driver 301 is good.

Figure 26:
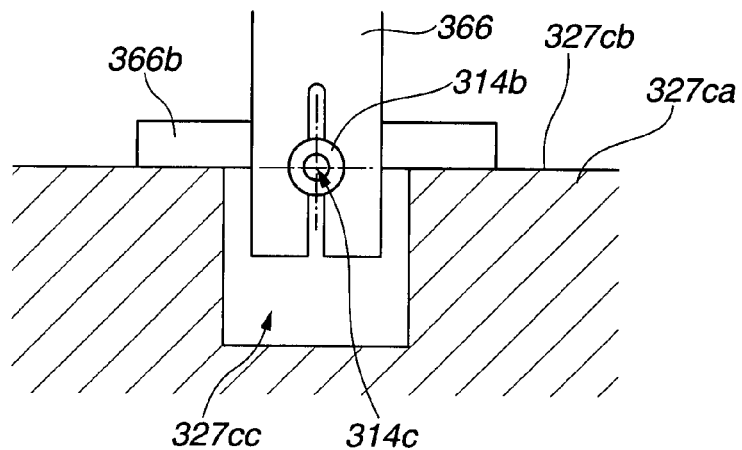
FIG. 26 is a diagram showing a modified example, wherein a state of a pull ring and a guide protruding portion being in contact is seen from the proximal end side of a traction wire.

Note that an arrangement is made wherein the pull link 366 is in contact with the flat surface portion 327cb of the guide protruding portion 327ca so that the traction wire 314 is pulled straight toward the proximal end side, but a configuration as shown in FIG. 26 may be employed as well. FIG. 26 is a diagram describing another configuration for pulling the traction wire 314 straight toward the proximal end side, and is a diagram wherein the state of the pull link 366 and guide protruding portion 327ca are in contact, as viewed from the proximal end side of the traction wire 314. As shown in FIG. 26, the pin 366b provided on the pull link 366 makes contact with the flat surface portion 327cb of the guide protruding portion 327ca. A groove portion 327cc is formed on the guide protruding portion 327ca, along the axial direction of the operation portion 303, and one end of the pull link 366 is inside the groove portion 327cc. In a state wherein the pin 366b is in contact with the flat surface portion 327cb, the shaft center 314c of the traction wire 314 is positioned within the flat surface of the flat surface portion 327cb. Accordingly, upon the open/close button 305 being pressed, one end of the pull link 366 is moved along the groove portion 327cc to pull the traction wire 314 toward the proximal end side. At this time, the traction wire 314 is pulled toward the proximal end side, while the shaft center 314c of the traction wire 314 is continually positioned within the flat surface of the flat surface portion 327cb. Accordingly, the traction wire 314 is pulled straight toward the proximal end side.

The operation of the brake shoe 362 resulting from the pushing operations of the two variable angle levers 306 and the open/close button 305 of the needle driver 301 relating to the present embodiment will be described in detail with reference to FIG. 27 through FIG. 31.

Figure 27:
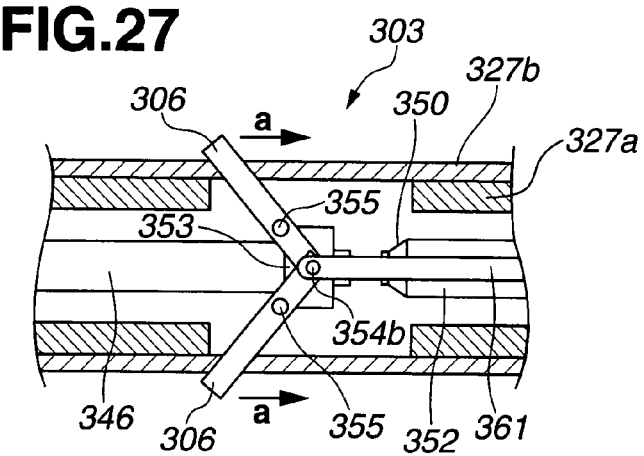
FIG. 27 is a partial cross-sectional view of an operation portion 303 for describing the operation of the variable angle lever of the needle driver relating to the present embodiment.
Figure 28:
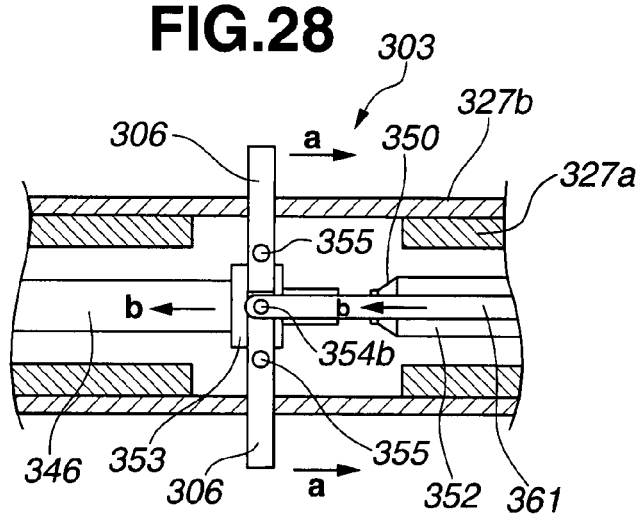
FIG. 28 is a partial cross-sectional view of the operation portion for describing the operation of the variable angle lever of the needle driver shown in FIG. 1.
Figure 29:
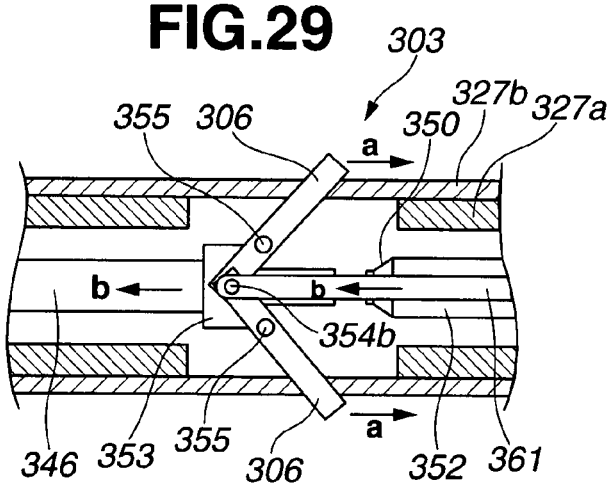
FIG. 29 is a partial cross-sectional view of the operation portion for describing the operation of the variable angle lever of the needle driver shown in FIG. 1.
Figure 30:
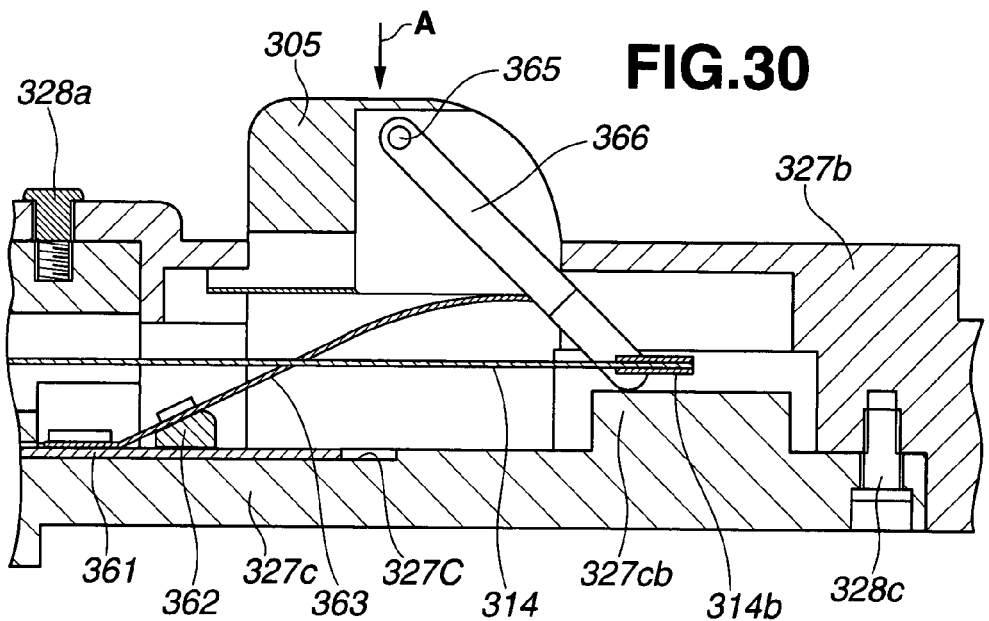
FIG. 30 is a partial cross-sectional view of the operation portion for describing the operation of a brake shoe of the needle driver according to the present embodiment.
Figure 31:
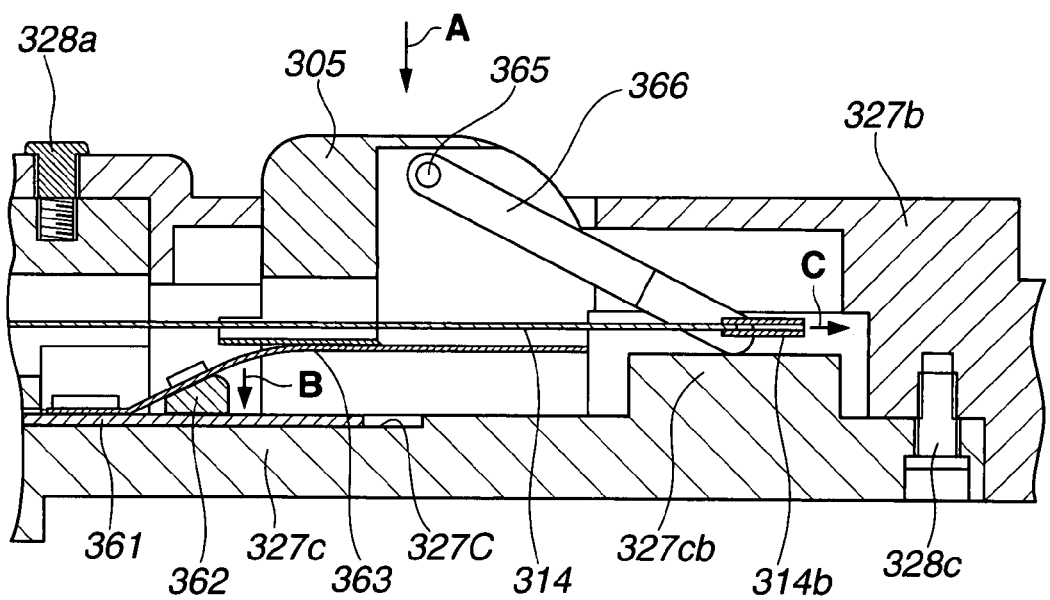
FIG. 31 is a partial cross-sectional view of the operation portion for describing the operation of a brake shoe of the needle driver shown in FIG. 1.

Note that FIG. 27 through FIG. 29 are partial cross-sectional views of the operation portion 303 for describing the operation of the variable angle lever 306, FIG. 30 and FIG. 31 are partial cross-sectional views of the operation portion 303 for describing the operation of the brake shoe 362.

First, the operation of the variable angle lever 306 will be described below with reference to FIG. 27 through FIG. 29. In a state of the variable angle lever 306 shown in FIG. 27, i.e. in the state wherein the two variable angle levers 306 tilt toward the left side in the diagram (the distal end side of the operation portion 303), the treatment portion 304 is in a state wherein the longitudinal axis thereof is on generally the same axis as the axis of the insertion portion 302, i.e. is in the state of being generally in a straight line as to the insertion portion 302.

Upon the surgeon operating one end portion of one of the variable angle levers 306 in the arrow a direction in FIG. 27, the two variable angle levers 306 each turn with the corresponding pivot pins 355 as the supporting axis thereof. As shown in FIG. 28 and FIG. 29, the other end portion on the side opposite the end operated by the surgeon is moved toward the distal end side of the operation portion 303 which is the arrow b direction.

Thus, the screw pins 354a and 354b (the diagram only shows the screw pin 354b) inserted in the slots 306a of the two variable angle levers 306 are pressed toward the distal end side within the operation portion 303. The thruster 353 wherein the screw pin 354 is screwed in is also moved integrally toward the distal end side which is the arrow b direction, thus the stopping pipe 346 is also pressed to advance. Accordingly, the brake bar 361 wherein the screw pin 354b is inserted on one end is also moved toward the distal end side which is the arrow b direction with the movement of the screw pin 354b.

Accordingly, as described above, the stopping pipe 346 presses the bending force transmitting pipe 315 to advance toward the distal end side, whereby the joint member 318 provided on the distal end portion of the bending force transmitting pipe 315 presses the link member 319 toward the distal end side. Also, by the link member 319 pressing the bending portion base member 320 toward the distal end side, the bending portion base member 320 turns on the pin 324 as the turning center thereof. Thus, the treatment portion 304 is subjected to bending operation within a 90 degree range as to the axis of the insertion portion 302 (see FIG. 13 and FIG. 14).

Also, upon the two variable angle levers 306 being operated in the inverse direction from that described above, each member is pulled toward the proximal end side, whereby the angle of the treatment portion 304 as to the axis of the insertion portion 302 becomes small, and the treatment portion 304 and the insertion portion 302 become in a generally linear state (see FIG. 6 and FIG. 8) with the position of the two variable angle levers 306 in FIG. 27.

Note that even if the surgeon releases his/her hand from the two variable angle levers 306, as described above, the brake bar 361 generates predetermined frictional force by the distal end side exterior member 327a and the groove portion 327C of the cover exterior member 327c, whereby due to the frictional force, the movement of each member is stopped, and the treatment portion 304 maintains the state of the angle desired by the surgeon as to the axis of the insertion portion 302.

As a result, by the surgeon moving one of the end portions of the two variable angle levers 306 toward the distal end side or the proximal end side along the side face of the operation portion 303, the desired bending operation of the treatment portion 304 with a 90 degree range can be performed as to the axis of the insertion portion 302.

Next, the operation of the brake shoe 362 by pressing operation of the open/close button 305 will be described with reference to FIG. 30 and FIG. 31.

As shown in FIG. 30, upon the open/close button 305 being pressed in the arrow A direction by the surgeon, the plate spring 363 presses the brake show 362 in the arrow B direction, as shown in FIG. 31.

The brake shoe 362 pressed toward the arrow B direction presses the brake bar 361 which is in contact with one face thereof, toward the arrow B direction.

Thus a portion of the brake bar 361 is pressed so as to be sandwiched between the brake shoe 362 and the groove portion 327C within the groove portion 327C of the cover exterior member 327c, the frictional force thereof preventing movement in the longitudinal axial direction of the operation portion 303.

Also, upon the open/close button 305 being pushed in the direction of the arrow A, the pull link 366 turns around the axis of the pin 365, and the one end portion through which the pin 365 is inserted is moved toward the inner direction of the operation portion 303 so as to sink in the arrow A direction. Accordingly, the other end of the pull link 366 moves toward the proximal end side of the operation portion 303 which is the arrow C direction, while sliding along the surface of the guide protruding portion 327ca of the cover exterior member 327c.

Thus, the traction wire 314 holding the wire pullout preventing member 314b on the other end of the pull link 366 is pulled in the arrow C direction, whereby the distal end side face of the flange portion 326c of the movable gripping piece 326 is distanced from the proximal end side face of the flange portion 331a of the fixed gripping piece 331.

Consequently, even if a force is generated so that the traction wire 314 tries to be straight, from the tensile force of the traction wire being pulled toward the proximal end side due to the open/close button 305 being pushed, the brake shoe 362 presses the bake bar 361 to stop the movement of the brake bar 361, whereby the treatment portion 304 can be securely maintained in a state of a predetermined angle as to the insertion portion 302.

Thus, the needle driver 301 relating to the present embodiment is configured such that, in a state wherein the treatment portion 304 is at a predetermined angle as to the axis of the insertion portion 302, upon the surgeon performing an operation to push the open/close button 305 for gripping a suture needle, the brake shoe 362 presses against the brake bar 361 and maintains the bending angle of the treatment portion 304. Therefore, even if force generated wherein the traction wire 314 tries to be straight from the tensile force pulling toward the proximal end side, the treatment portion 304 can securely maintain the state of a predetermined angle as to the insertion portion 302.

Also, with the needle driver 301, even if the open/close button 305 is not pressed, the brake bar 361 receives predetermined frictional force from the brake shoe 362 and cover exterior member 327c. Thus, even if the surgeon releases his/her hand from the variable angle lever 306, the treatment portion 304 can maintain the state of being changed to a predetermined angle as to the axis of the insertion portion 302.

Accordingly, according to the needle driver relating to the present embodiment as described above, a surgical treatment instrument with good operability for tissue anastomosis or the like using an endoscope can be realized. Since the operability is good, tissue anastomosis can be readily performed using an endoscope, improving the quality of surgery, shortening the surgery time, and further, since a smaller diameter can be realized, the procedure is less invasive, facilitating an earlier discharge from the hospital and return to society of the patient.

Figure 32:
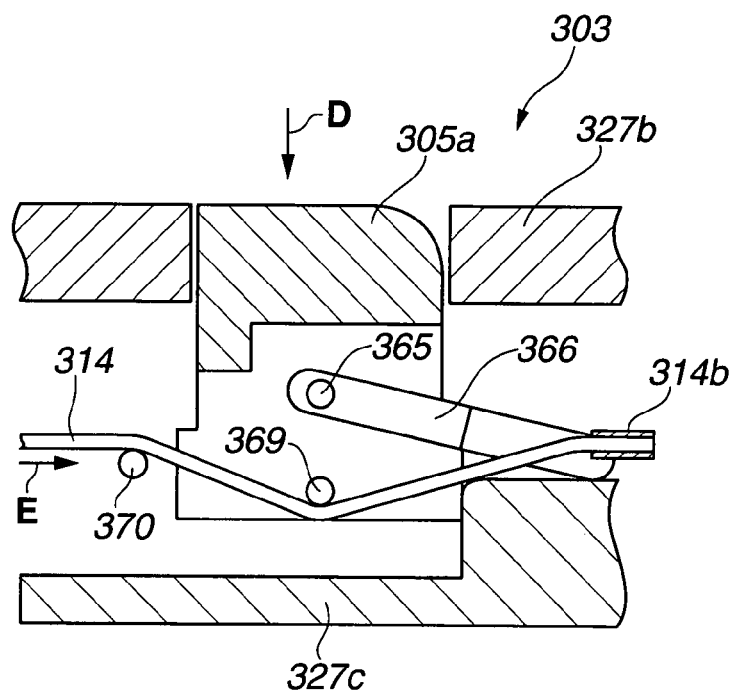
FIG. 32 is a partial cross-sectional view of the operation portion of the needle driver serving as a first modified example.

Note that as shown in FIG. 32, an open/close button 305A serving as a first modification may have a pin 369 provided orthogonally to the longitudinal axial direction of the operation portion 303 in the vicinity of the end face on the inner side of the operation portion 303. Also, the main unit exterior member 327b may have a pin 370 disposed generally orthogonal to the axis of the traction wire 314, at a position farther on the cover exterior member 327c than the traction wire 314.

Upon the open/close button 305A being pushed by the surgeon in the arrow D direction, as described above, the traction wire 314 is pulled toward the proximal end side by the pull link 366, while the pin 369 pushes the traction wire 314 in the direction of the cover exterior member 327c. At this time, the traction wire 314 makes contact with the pin 370, and is pushed by the pin 369 toward the cover exterior member 327c, whereby the pulling distance toward the proximal end side which is the arrow E direction greatly increases.

Accordingly, with this configuration, the distal end side face of the flange portion 326c of the movable gripping piece 326 is distanced from the proximal end side face of the flange portion 331a of the fixed gripping piece 331 in a sure manner. Note that FIG. 32 is a partial cross-sectional view of the operation portion 303 of the needle driver 301 serving as a first modified example.

Figure 33:
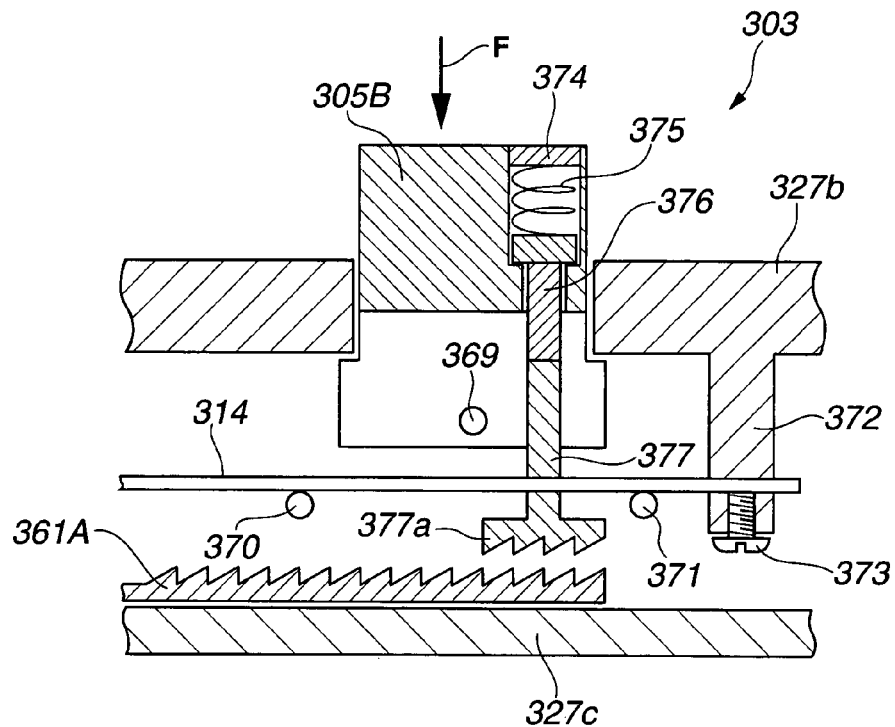
FIG. 33 is a partial cross-sectional view of the operation portion for describing the configuration and action of the needle driver serving as a second modified example.
Figure 34:
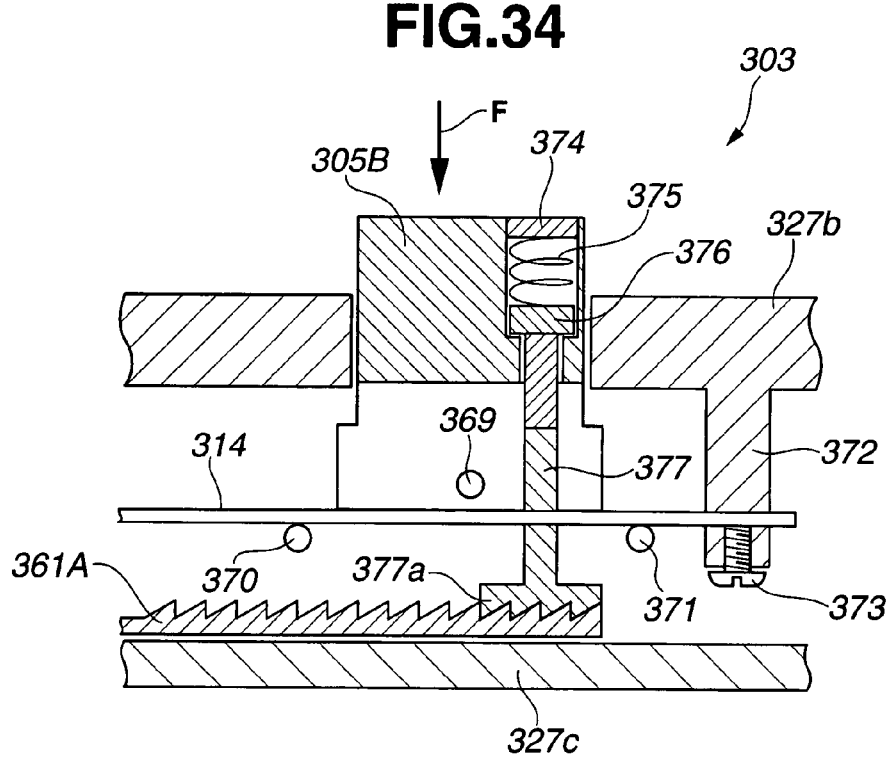
FIG. 34 is a partial cross-sectional view of the operation portion for describing the configuration and action of the needle driver shown in FIG. 33.
Figure 35:
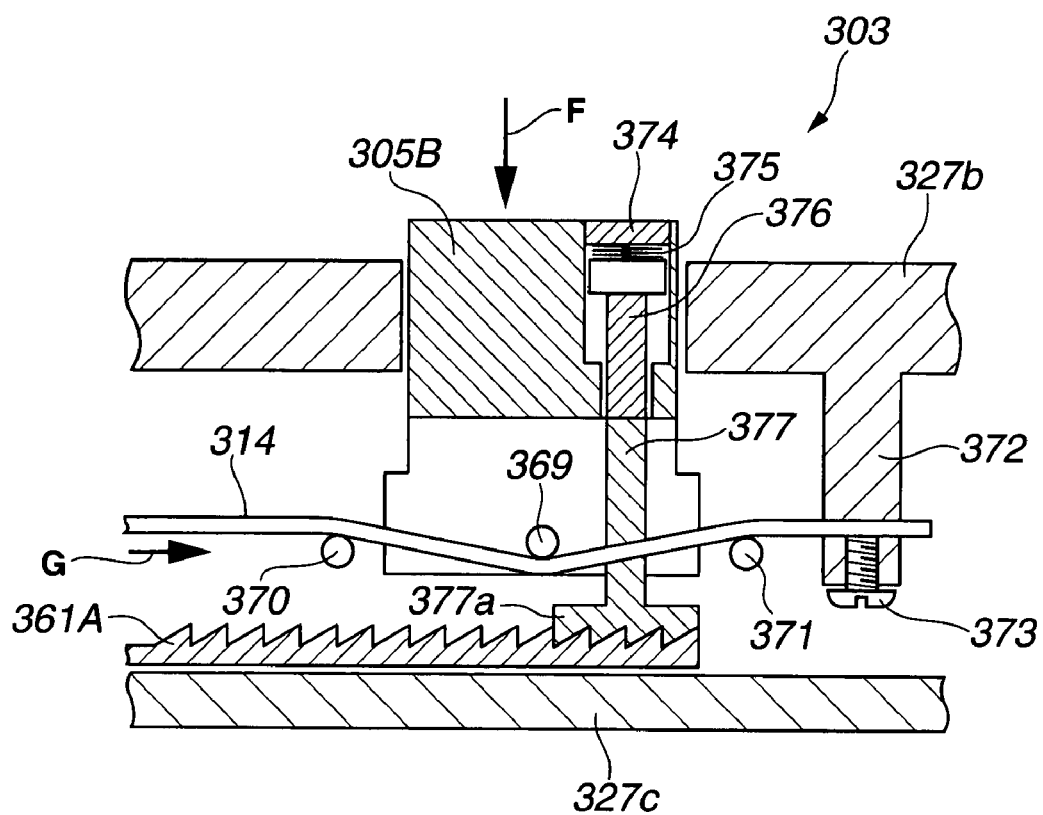
FIG. 35 is a partial cross-sectional view of the operation portion for describing the configuration and action of the needle driver shown in FIG. 33.

Also, the needle driver 301 may be configured to brake the movement of the braked member with braking means serving as a second modified example, so that a state wherein the treatment portion 304 can maintain a predetermined angle as to the axis of the insertion portion 302 as shown in FIG. 33 through FIG. 35.

Note that FIG. 33 through FIG. 35 are partial cross-sectional views of the operation portion 303 for describing the configuration and action of the needle driver 301 serving as a second modified example.

As shown in FIG. 33 through FIG. 35, the open/close button 305B of the needle driver 301 serving as the second modified example has no pull link provided thereto, thus is configured such that the traction wire 314 is moved toward the proximal end side only with the pin 369 as described above, by the surgeon pushing the open/close button 305B in the arrow F direction.

Also, a hole portion is formed on the open/close button 305B in the direction orthogonal to the longitudinal axial direction of the operation portion 303, and a shaft member 376 having a flange formed on one end is inserted into the hole portion. A spring 375 which presses the shaft portion 376 in the interior direction of the operation portion 303 is provided on the hole portion, one end of the spring 375 making contact with the flange portion of the shaft member 376. The open/ close button 305B is configured by a lid member 374 for closing off the hole portion being attached to the other end side of the spring 375.

A brake member 377 serving as braking means made of a metal such as stainless steel is adhered to the end portion on the opposite side from the flange portion on the shaft member 376, so as to have a longitudinal axis on the axis of the shaft member 376. The brake member 377 has a brake unit 377a whereupon an irregular surface is formed on the end portion of the opposite side as to the shaft member 376 side. Corresponding to this, an irregular surface which engages with the irregular surface on the brake unit 377a is also formed on the surface of the open/close button 305B side on the brake bar 361A serving as the braked member.

Also, the traction wire 314 is fixed by a screw 373 to a protruding portion 372 provided on the main unit exterior member 327b of the proximal end portion so that predetermined tensile force is applied to the traction wire 314 causing the traction wire 314 to be in a generally straight line in the longitudinal axial direction. Further, two pins 370 and 371 are disposed on the main unit exterior member 327b to be generally orthogonal to the axis of the traction wire 314. Note that the two pins 370 and 371 are provided on the main unit exterior member 327b, separated by a predetermined distance from each other, so as not to come in contact with the open/close button 305B pressed in to the inner portion of the operation portion 303.

Upon the open/close button 305B of the needle driver 301 configured as above shown in FIG. 33 and FIG. 34 being pushed in toward the arrow F direction, first, the brake member 377 is moved while receiving pressing force from the spring 375 toward the brake bar 361A side, along with the shaft member 376. The brake unit 377a of the brake member 377 stops in a state wherein the irregular surface thereof engages with the irregular surface of the brake bar 361A.

Note that in this state, the pin 369 of the open/close button 305B is in a state of not being in contact with the traction wire 314. Upon the surgeon pressing the open/close button 305B in the arrow F direction, the pin 369 makes contact with the traction wire 314, and presses into the brake bar 361A side.

The traction wire 314 is held by two pins 370 and 371 of the main unit exterior member 327b, and is pressed into the brake bar 361A side by the pin 369 of the open close button 305B, thereby moving so as to be pulled toward the proximal end side which is the arrow G direction. Thus, the distal end side face of the flange portion 326c of the movable gripping piece 326 is distanced from the proximal end side face of the flange portion 331a of the fixed gripping piece 331.

In this state also, since the brake member 377 has the irregular surface of the brake unit 377a engaging with the irregular surface of the brake bar 361A, the movement in the axial direction of the brake bar 361A is braked. Also, the spring 375 of the open/close button 305B compresses, and the brake member 377 applies pressing force to the brake bar 361A side via the shaft member 376. Therefore, during the time that the open/close button 305B is pushed in, the brake bar 361A continually receives braking force by the brake unit 377a of the brake member 377.

Consequently, even if a force is generated so that the traction wire 314 tries to be straight by the tensile force of the traction wire 314 being pulled toward the proximal end side due to the open/close button 305 being pushed, the movement of the brake bar 361A is stopped, enabling the treatment portion 304 to be maintained in a state of a predetermined angle as to the insertion portion 302.

Also, according to the needle driver 301 of the present invention as configured above, as shown in FIG. 33 and FIG. 34, when the open/close button 305B is pressed, the brake bar 361A is braked by the brake member 377 before the traction wire 314 can be pulled toward the proximal end side, thus having a configuration which enables the treatment portion 304 to be maintained in a state of a predetermined angle as to the insertion portion 302 in a sure manner.

Second Embodiment

A second embodiment according to the present invention will be described below.

A needle driver according to the present embodiment will be described with reference to FIG. 36 through FIG. 47, in which components which are the same as those of the first embodiment will be denoted with the same reference numerals and description thereof will be omitted, and only different configurations, operations, and advantages will be described.

Figure 36:
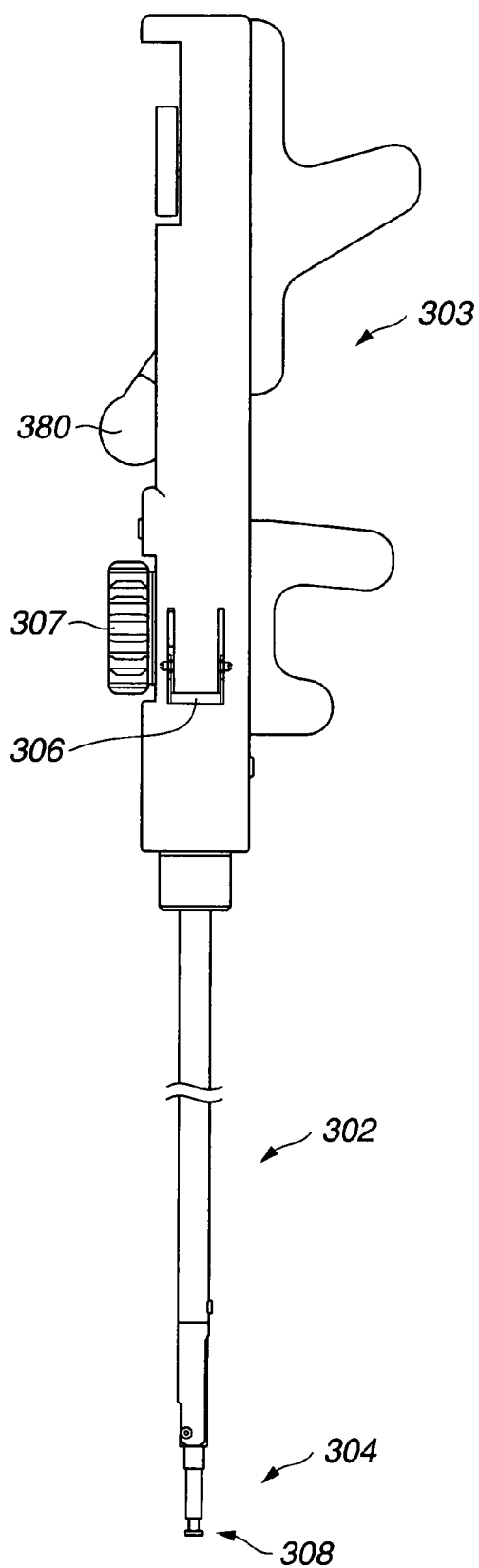
FIG. 36 is a front view of the needle driver relating to a second embodiment of the present invention.
Figure 37:
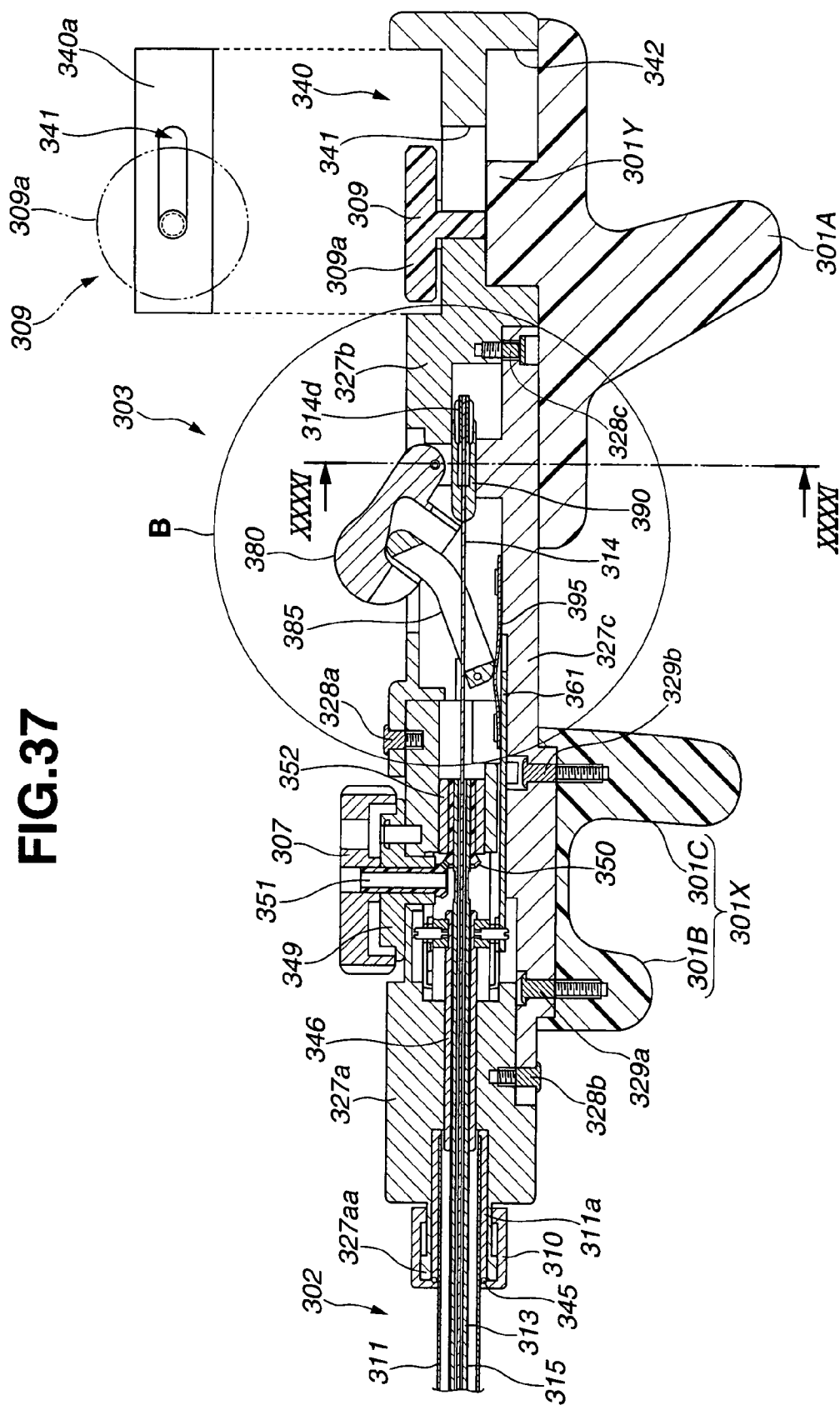
FIG. 37 is a cross-sectional view of the operation portion along the axial direction of the needle driver shown in FIG. 36.
Figure 38:
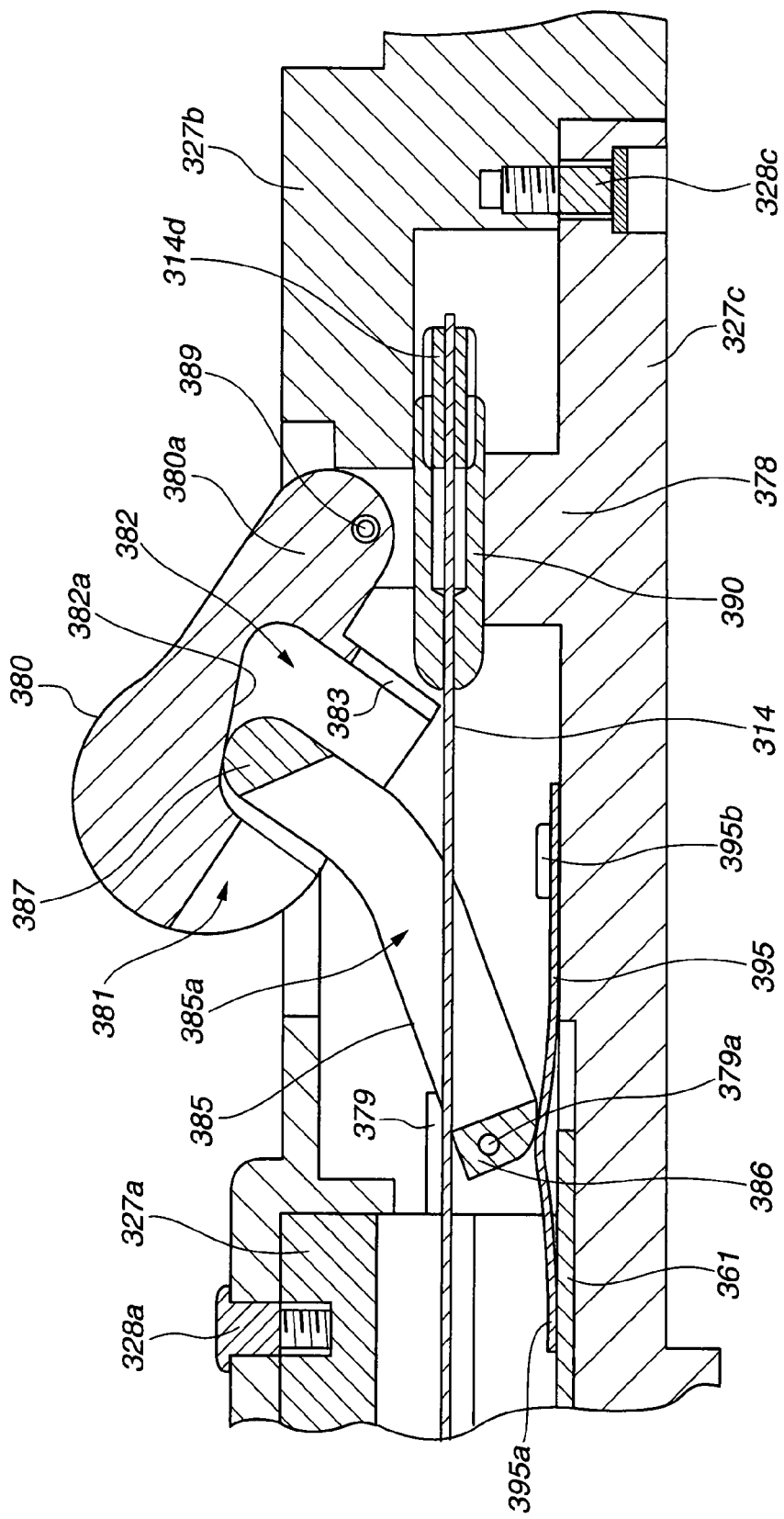
FIG. 38 is a partial cross-sectional view of the operation portion along the axial direction of the needle driver wherein the portion surrounded by a circle B in FIG. 36 is enlarged.
Figure 39:
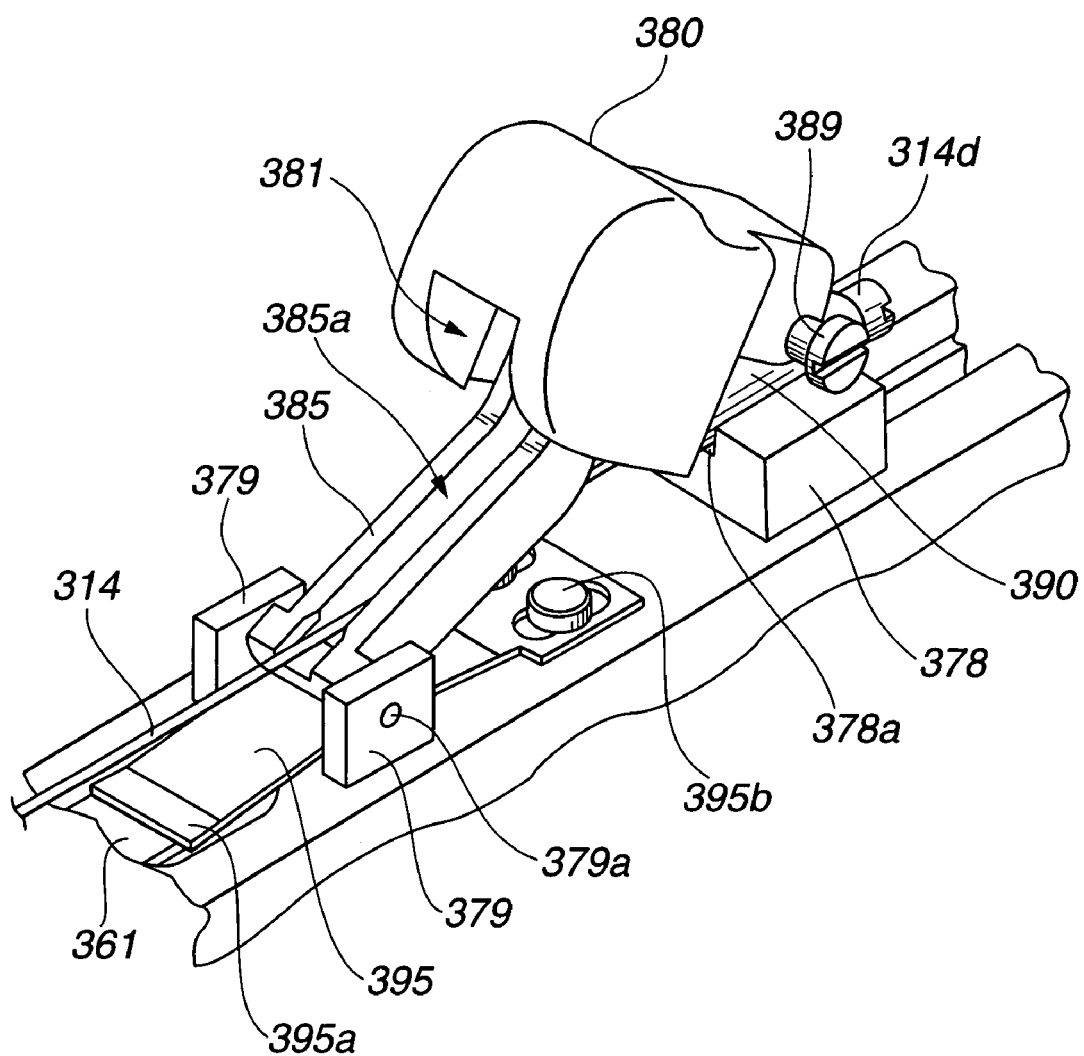
FIG. 39 is a perspective view showing the mechanism within the operation portion of the needle driver shown in FIG. 36.
Figure 40:
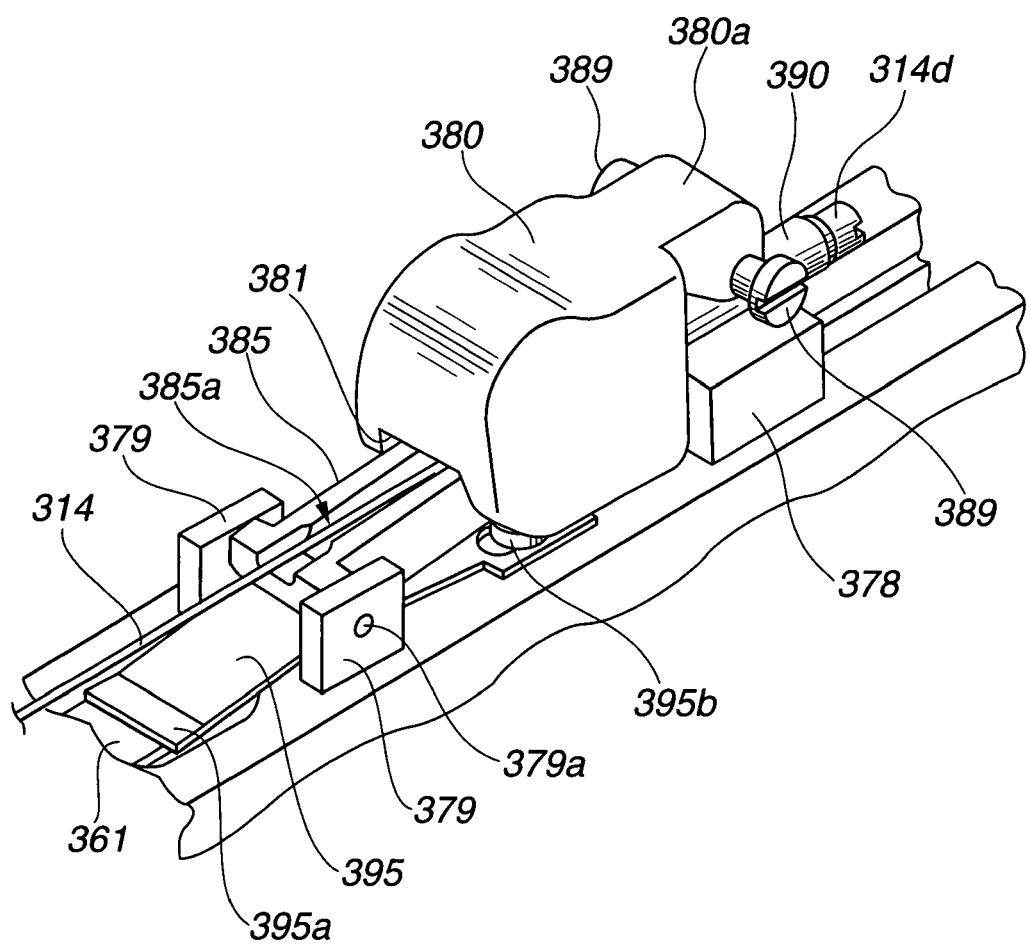
FIG. 40 is a perspective view showing the mechanism within the operation portion of the needle driver shown in FIG. 36, in a state wherein the open/close button is operated.
Figure 41:
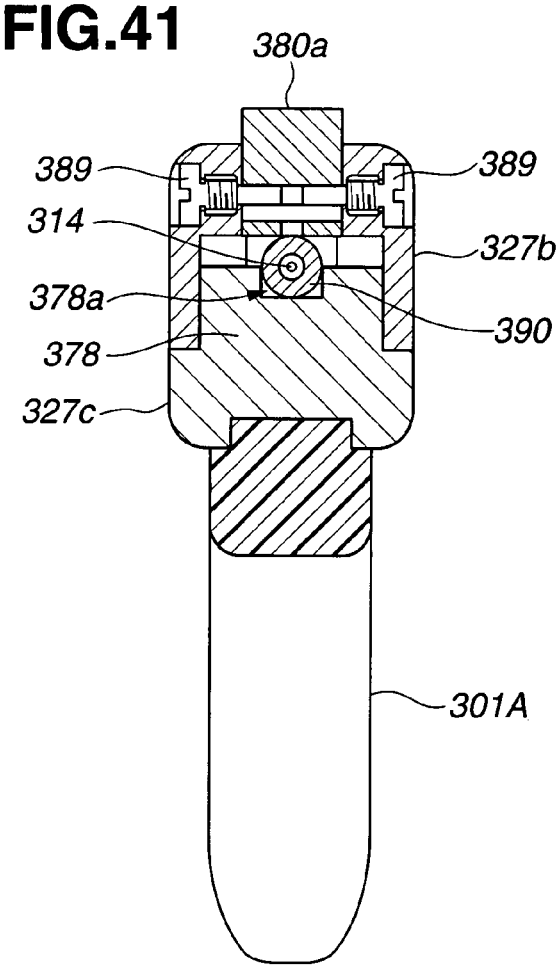
FIG. 41 is a cross-sectional view of a needle driver, taken along the XXXXI-XXXXI line in FIG. 37.

FIG. 36 is a front view of the needle driver relating to the present embodiment, FIG. 37 is a cross-sectional view of the operation portion along the axial direction of the needle driver shown in FIG. 36, FIG. 38 is a partial cross-sectional view of the operation portion along the axial direction of the needle driver wherein the portion surrounded by a circle B in FIG. 36 is enlarged, FIG. 39 is a perspective view showing the mechanism within the operation portion of the needle driver, FIG. 40 is a perspective view showing the mechanism within the operation portion of the needle driver, in a state wherein the open/close button is operated, and FIG. 41 is a cross-sectional view of the needle driver, taken along the XXXXI-XXXXI line in FIG. 37.

As shown in FIG. 36 through FIG. 41, the needle driver 301 according to the present embodiment has, in the same way as with the first embodiment, an aluminum open/close button 380 serving as an open/close operating member for performing opening/closing operations of the treatment portion 304, a stainless steel link member 385 operating in conjunction with operations of the open/close button 380, and a plate spring 395 which is an elastic element formed of high-tensile strength steel such as stainless steel for example, serving as a braking means for braking a brake lever 361 which is a braked member.

The open/close button 380 has a groove portion 381 notched out at the generally middle portion from the distal end to the proximal end, from the back face serving as the inner space side formed in the operation portion 303, a hole portion 382 having a top, which opens at generally the middle of the groove portion 381, a contact portion 383 serving as a proximal end portion, and a turning supporting portion 380a which protrudes from the contact portion 383 toward the proximal end (see FIG. 38).

The groove portion 381 is a groove provided for storing in the state that the later-described open/close button 380 is operated, so as to prevent contact with the link member 385 and traction wire 314 (See FIG. 40). The hole portion 382 has a generally-trapezoid-shaped cross-sectional form such that a top face 382a is inclined toward the distal end side, with one end portion of the link member 385 stored therein. The top face 382a of the hole portion 382 makes up a sliding face with which one end portion of the link member 385 comes into contact with and slides upon.

Pin holes are formed in the turning supporting portion 380a (see FIG. 41). The open/close button 380 is rotatably held as to the main unit exterior member 327b by two screw pins 389 inserted into the pin holes of the turning supporting portion 380a. Accordingly, the movement of the open/close button 380 owing to contact with the opening portion of the cover exterior member 327 is not obstructed, and the operability thereof improves.

The link member 385 has a bent shape when viewed form the side (see FIG. 38), with a slot 385a from at the middle portion from the upper face to the lower face. The link member 385 has a plate spring side contact portion 386 for coming into contact with the plate spring 395 at the other end of the cover exterior member 327c, and an open/close button side contact portion 387 coming into contact with the base face of the hole portion 382 having an inclined face shape, at the one end portion stored in the hole portion 382 of the open/close button 380.

Also, the traction wire 314 is inserted through the slot 385a of the link member 385. As described later, the slot 385a is formed such that, at the time of pressing operation of the open/close button 380, the link member 385 operating in conjunction with this operation does not come into contact with the traction wire 314, and accordingly does not obstruct movement of the traction wire 314 in the axial direction.

The plate spring side contact portion 386 forms a driver (cam) with an outline curve formed on the contact face thereof which comes into contact with the plate spring 395. A pin 379a provided between two turning supporting members 379 having square pillar shapes protruding from the upper face of the cover exterior member 327c, is inserted through the plate spring side contact portion 386. Thus, the plate spring side contact portion 386 can turn on the pin 379a as to the cover exterior member 327c.

Also, the contact face of the open/close button side contact portion 387 which comes into contact with the top face 382a of the hole portion 382 of the open/close button 380 is formed in an arc shape. The open/close button side contact portion 387 is stored in the hole portion 382 of the open/close button 380 in a free state. Accordingly, the contact face of the open/close button side contact portion 387 slides along the top face 382a of the hold portion 382 due to operations of the open/close button 380.

The plate spring 395 is a high-elastic-force spring formed of high-tensile strength steel or the like, regarding which a high elastic coefficient has been set. The plate spring 395 has a pressing portion 395a at the distal end portion thereof, which presses the brake bar 361, with the midway portion bent in a so-called mountain fold such that the midway portion protrudes toward the inner space side of the operation portion 303. Note that the midway portion of the plate spring 395 is not restricted to the mountain form, and may be formed in a curved shape for example, so as to protrude toward the inner space side of the operation portion 303. Also, the plate spring 395 is fixed at the proximal end portion to the cover exterior member 327c by a screw 395b.

The plate spring 395 is a subordinate member which is driven by the plate spring side contact portion 386 formed on the outline curve which is one end portion of the link member 385 moving and the plate spring side contact portion 386 coming into contact. Accordingly, the link member 385 and the plate spring 395 form a so-called cam mechanism. Thus, the surgeon can press the plate spring 395, which is a subordinate member and is a high-tensile-strength spring, with a small stroke, due to movement of the plate spring side contact portion 386, which is a driver, of the link member 385. Accordingly, the amount of protrusion bent in a mountain fold midway on the plate spring 395 can be shortened. This enables saving of space within the inner space formed in the operation portion 303, and also enables the operation portion 303 to be formed with a small size.

Now, as with the first embodiment, even in the event that the surgeon releases the two variable angle levers 306 from the hand, a predetermined amount of friction is generated at the brake bar 361 by the distal end side exterior member 327a and the groove portion 327C of the cover exterior member 327c, and also, pressing force of the pressing portion 395a of the plate spring 395 to the brake bar 361 is applied, thereby stopping movement of the brake bar 361. Accordingly, the treatment portion 304 maintains a state in a sure manner wherein the angle which the surgeon desires as to the axis of the insertion portion 302 is kept, in a sure manner.

Note that when the open/close button 380 is not being operated, i.e., when the flat surface portions of each of the movable gripping piece 326 and the fixed gripping piece 331 are in close contact, the outline curve which is formed on the plate spring side contact portion 386 applies a predetermined pressing force to the plate spring 395. Accordingly, the pressing portion 395a of the plate spring 395 is constantly pressing so as to provide predetermined braking force necessary for braking the brake bar 361.

With the present embodiment, a stainless steel wire stopper member 314d fixed by soldering, and a wire end 390 formed of stainless steel in a generally cylindrical shape, are provided to the proximal end portion of the traction wire 314 for opening/closing the treatment portion 304. The wire stopper member 314d is fastened by screwing to the wire end 390 externally fit to the traction wire 314 beforehand, besides by fixed by adhesion.

More specifically, a screw thread serving as a male screw is formed on the outer perimeter face of the wire stopper member 314d, and a screw thread serving as a female screw is formed on the inner circumference face of the wire end 390. Thus, the wire stopper member 314d and the wire end 390 are fixed by screwing.

Also note that the position of the wire end 390 in the axial direction as to the traction wire 314 can be adjusted by the amount of screwing between the wire stopper member 314d and the wire end 390 being adjusted. Accordingly, the distal end of the wire end 390 comes into contact with the contact portion 383 of the open/close button 380, and the amount of movement of the traction wire 314 moving toward the proximal end portion in accordance with operation of the wire end 390 to be described later can be fine-tuned.

Consequently, adjusting the amount of movement of the traction wire 314 toward the proximal end side enables adjustment of the separation distance between the distal end side face of the flange portion 326c of the movable gripping piece 326 and the proximal end side face of the flange portion 331a of the fixed griping piece 331.

Now, the cover exterior member 327c has a guide protrusion portion 378 protruding from the face at the proximal end portion toward the side forming the internal space of the operation portion 303. A guide groove 378a following the longitudinal axial direction of the cover exterior member 327c is formed on a protruding face of the guide protrusion portion 378.

The guide groove 378a of the guide protrusion portion 378 is a groove for linearly guiding the above-described wire end 390. The guide protrusion portion 378, guide groove 378a, and wire end 390 have their respective dimensions regarding the amount of protrusion, groove depth, and external diameter, adjusted so as to be able to guide such that the traction wire 314 can move in a straight manner on the longitudinal axis.

Also, in the state wherein the main unit exterior member 327b and the cover exterior member 327c are assembled (see FIG. 41), the wire end 390 is fitted in the guide groove 378a, and is slidable in the axial direction between the main unit exterior member 327b and the guide protrusion portion 378.

Now, in a state wherein the open/close button 380 is not operated by the surgeon, the plate spring 395 presses the plate spring side contact portion 386 of the link member 385 in the direction of being pressed up to the inner space side of the operation portion 303. Due to the contact face of the plate spring side contact portion 386 thus pressed being formed as an outline curve, the link member 385 is constantly provided with pressing force in the direction of pressing the open/close button 380 upwards. Accordingly, the open/close button 380 maintains the state of protruding form the operation portion 303 in the state wherein the surgeon is not operating the open/close button 380.

Next, the link member 385 operating in conjunction with depressing operation of the open/close button 380 of the needle driver 301 according to the present embodiment configured as described above, and the braking operation of the brake bar 361 upon which the plate spring 395 acts due to the conjunctive operations of the link member 385, will be described with reference to FIG. 42 through FIG. 47.

Figure 42:
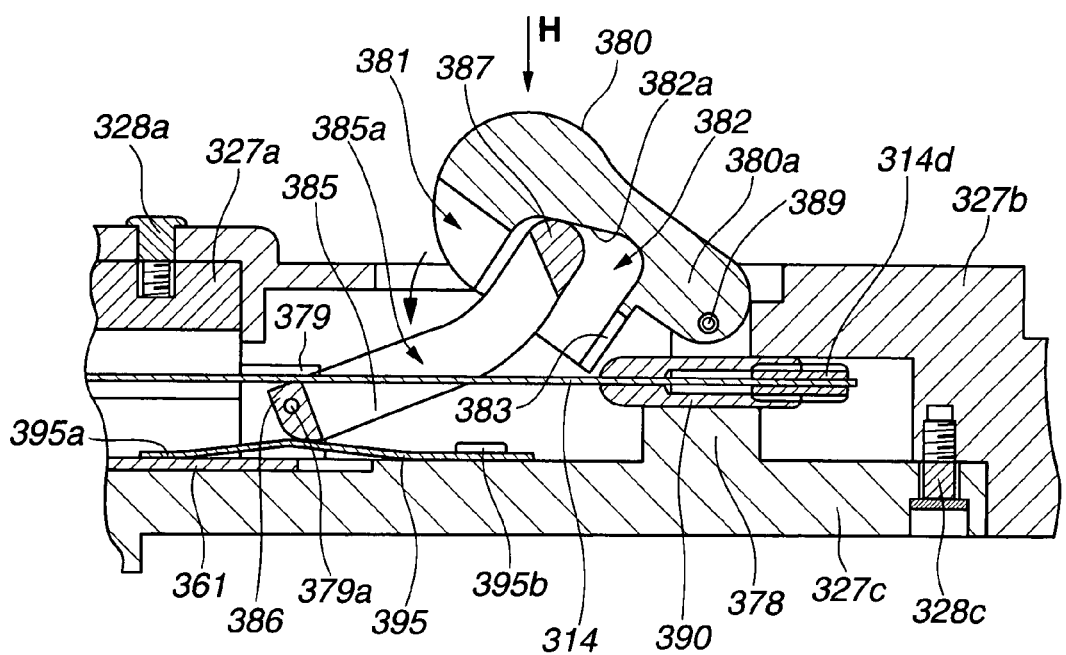
FIG. 42 is a diagram for describing the action of the needle driver shown in FIG. 36 before operation of the open/close button.
Figure 43:
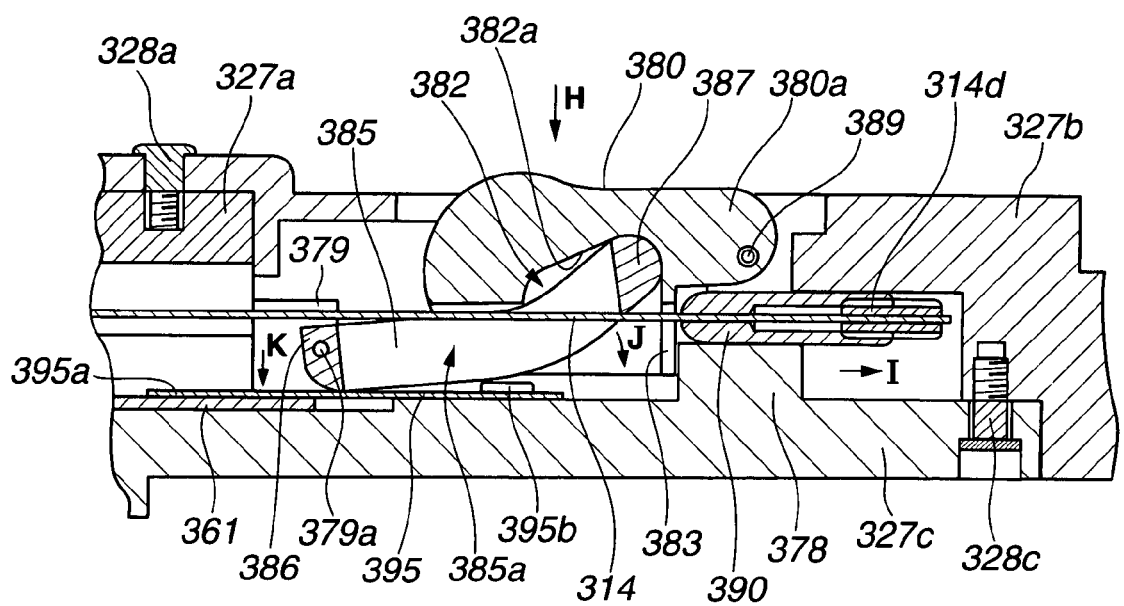
FIG. 43 is a diagram for describing the action of the needle driver shown in FIG. 36 after operation of the open/close button.
Figure 44:
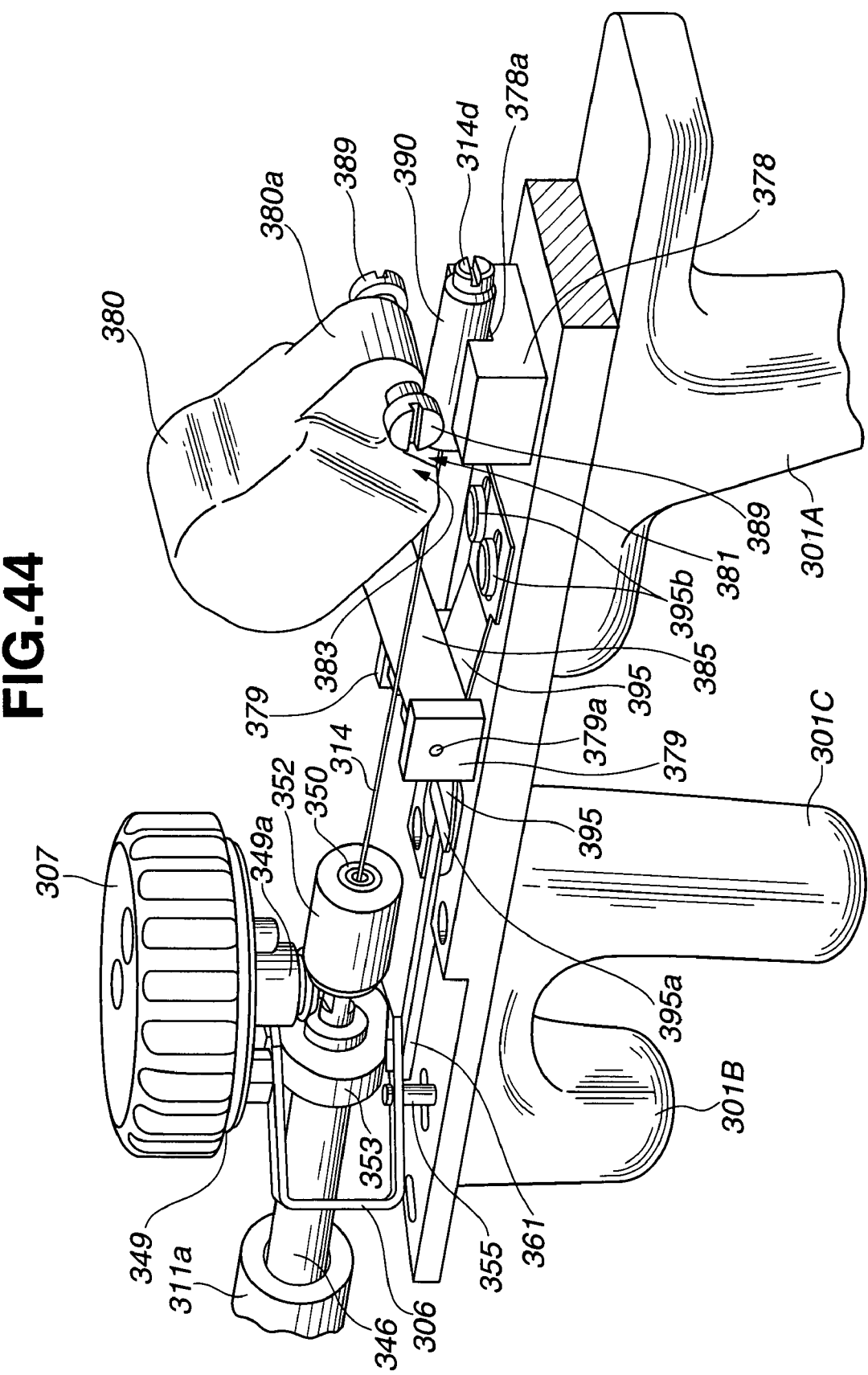
FIG. 44 is a perspective view showing the mechanism within the operation portion of the needle driver before the open/close button of the needle driver shown in FIG. 36 is operated.
Figure 45:
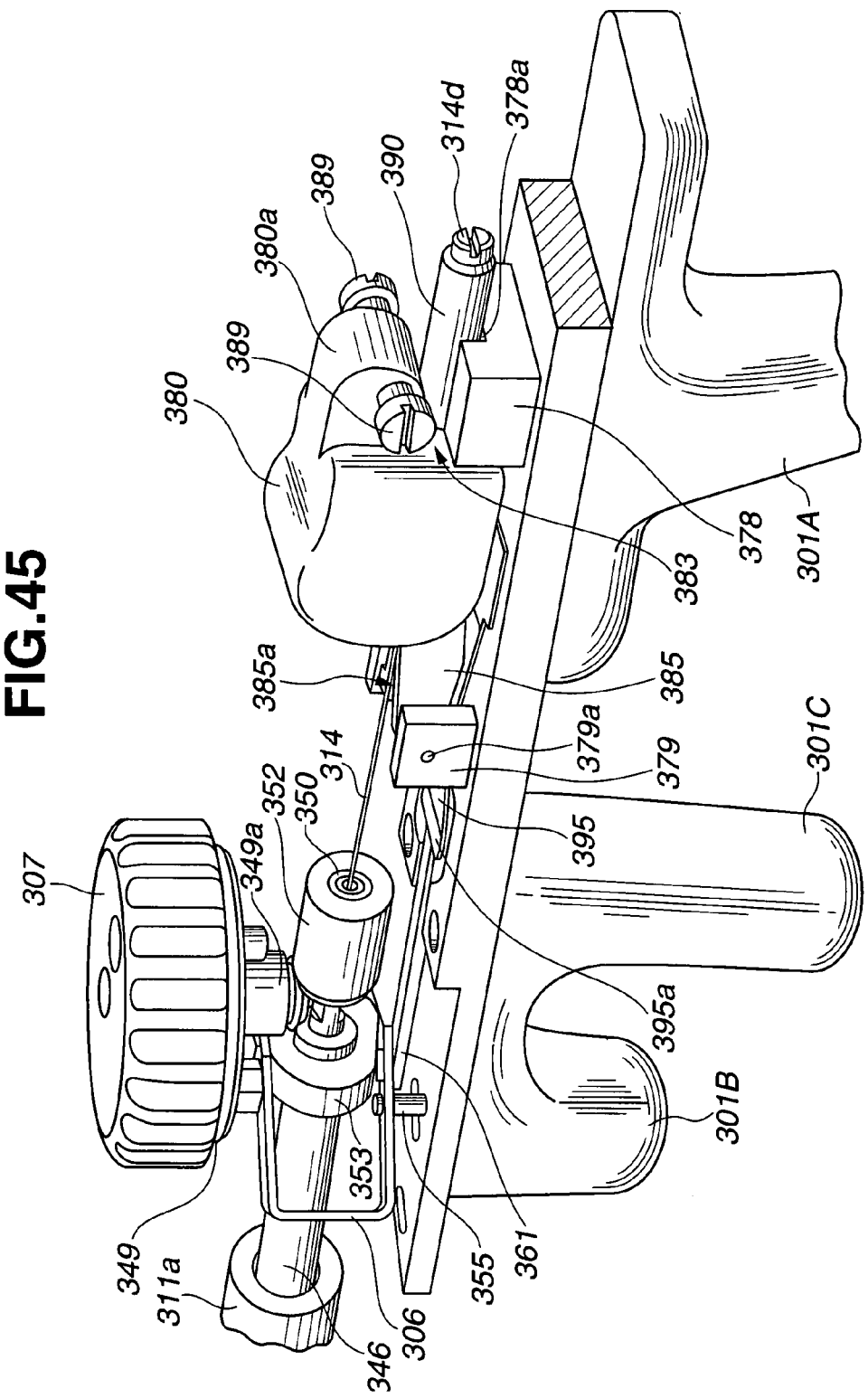
FIG. 45 is a perspective view showing the mechanism within the operation portion of the needle driver in the state of the open/close button of the needle driver shown in FIG. 36 having been operated.
Figure 46:
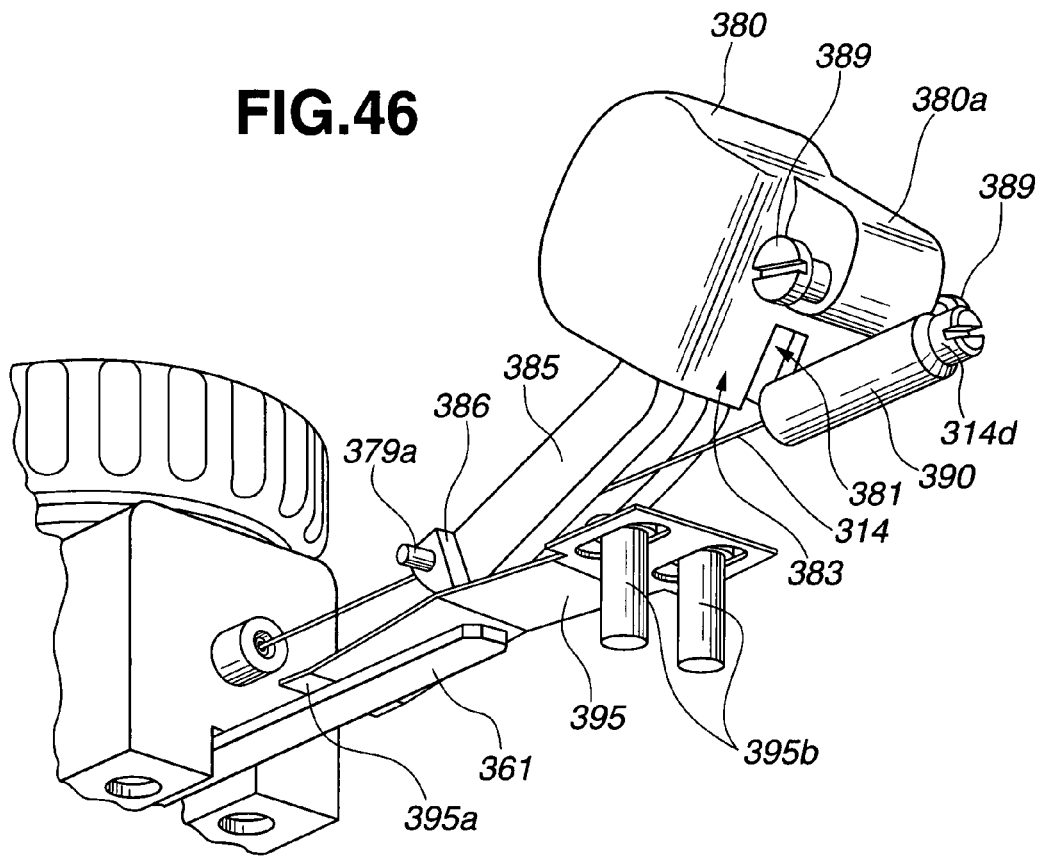
FIG. 46 is a perspective view showing the mechanism within the operation portion of the needle driver before the open/close button of the needle driver shown in FIG. 36 is operated.
Figure 47:
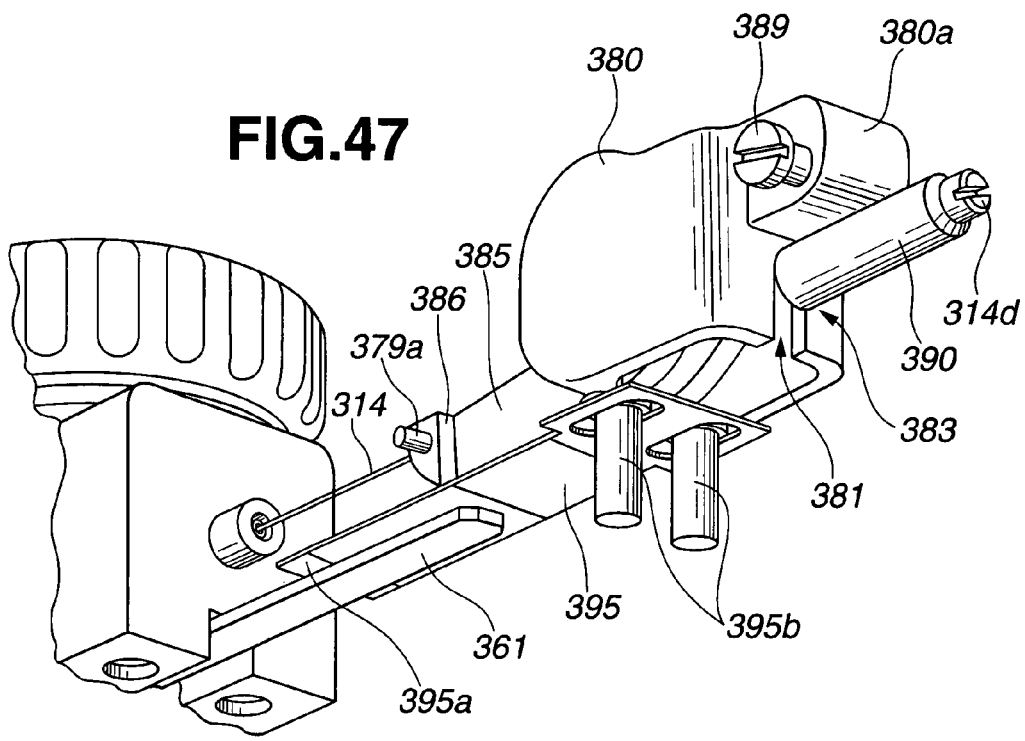
FIG. 47 is a perspective view showing the mechanism within the operation portion of the needle driver in the state of the open/close button of the needle driver shown in FIG. 36 having been operated.
Figure 48:
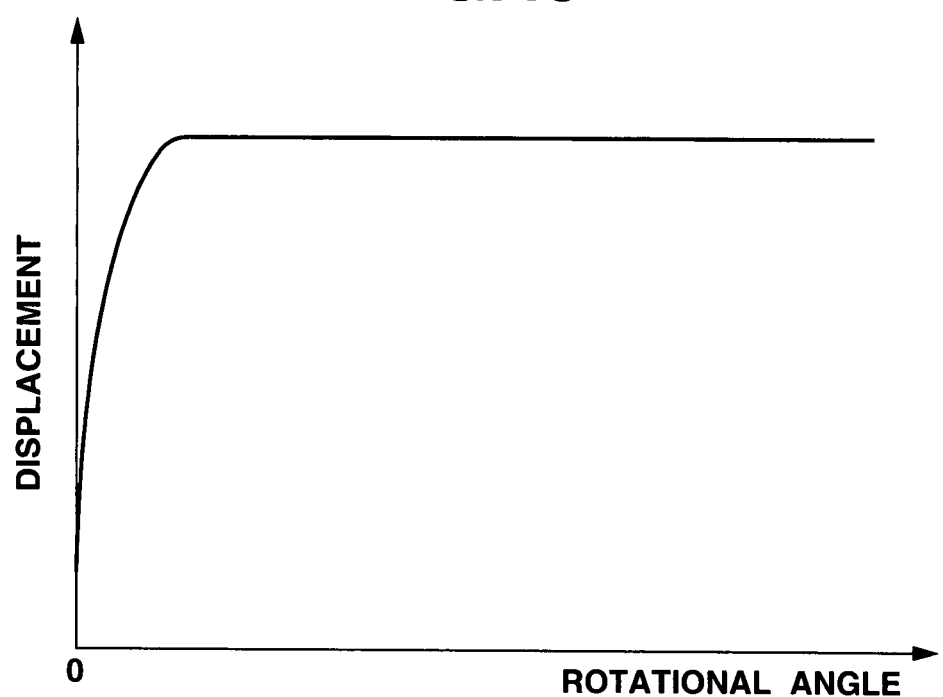
FIG. 48 is a cam line diagram showing the relation between rotational angle of the joint member and the displacement of a plate spring of the needle driver shown in FIG. 36.
Figure 49:
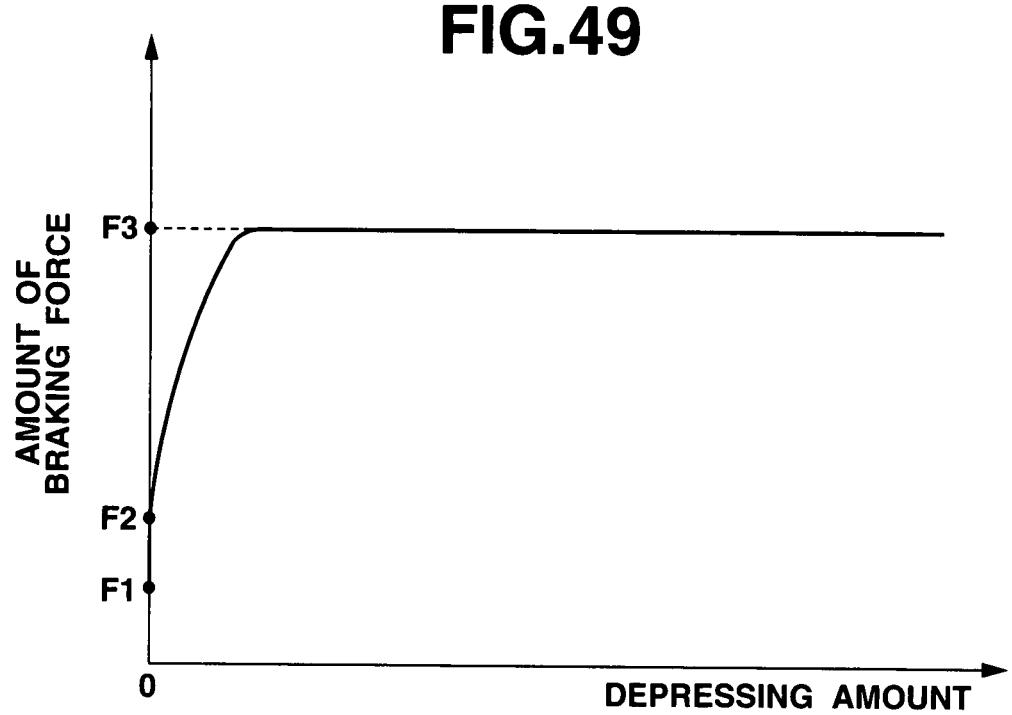
FIG. 49 is a line diagram showing the relation between the depressing amount of the open/close button, and braking force of the plate spring operating a brake bar, of the needle driver shown in FIG. 36.

Note that FIG. 42 is a diagram for describing the action of the needle driver before operation of the open/close button, FIG. 43 is a diagram for describing the action of the needle driver after operation of the open/close button, FIG. 44 is a perspective view showing the mechanism within the operation portion of the needle driver before the open/close button is operated, FIG. 45 is a perspective view showing the mechanism within the operation portion of the needle driver in the state of the open/close button having been operated, FIG. 46 is a perspective view showing the mechanism within the operation portion of the needle driver before the open/close button is operated, FIG. 47 is a perspective view showing the mechanism within the operation portion of the needle driver in the state of the open/close button having been operated, FIG. 48 is a cam line diagram showing the relation between rotational angle of the link member and the displacement of a plate spring, and FIG. 49 is a line diagram showing the relation between the depressing amount of the open/close button, and braking force of the plate spring braking a brake bar.

FIG. 44 and FIG. 46 illustrate the members within the operation portion 303 in the state that there is no depressing operation of the open/close button 380, and FIG. 45 and FIG. 47 illustrate the members within the operation portion 303 in the state that there is depressing operation of the open/close button 380.

As shown in FIG. 42, the open/close button 380 is pressed in the direction of the arrow H by the surgeon. Accordingly, the open/close button 380 turns on the screw pin 389 supporting the turning supporting portion 380a, into the inner space formed in the operation portion 303.

As shown in FIG. 43, the contact portion 383 of the open/close button 380 comes into contact with the distal end of the wire end 390, and moves the traction wire 314 along with the wire end 390 in the direction of the arrow I, which is the proximal end side. Thus, due to movement of the traction wire 314 toward the proximal end side, the distal end side face of the flange portion 326c of the movable gripping piece 326 is distanced from the proximal end side face of the flange portion 331a of the fixed griping piece 331.

At this time, the wire end 390 is linearly guided along the guide groove 378a of the guide protrusion portion 378, and accordingly the traction wire 314 is pulled to the proximal end side on the longitudinal axis. Also, the traction wire 314 is not obstructed regarding movement in the direction of the arrow I, since there is no contact between the open/close button 380 and the link member 385 due to the groove portion 381 of the open/close button 380 and the slot 385a of the link member 385.

Upon depressing operation of the open/close button 380, the open/close button side contact portion 387 of the link member 385 slides over the top face 382a of the hole portion 382 of the open/close button 380 while moving toward the proximal end side, such that the link member 385 turns on the pin 379a turnably supporting the plate spring side contact portion 386 in the direction of the arrow J. The arc-shaped end face of the plate spring side contact portion 386 of the link member 385 strongly presses the plate spring 395 in the direction of the arrow K from the point in time of starting turning.

That is to say, the plate spring side contact portion 386 of the link member 385 has the end face shape thereof formed as an outline curve such that, immediately following action due to the depressing operation of the open/close button 380, the plate spring 395 can rapidly be pressed strongly in the direction of the arrow K. In other words, the plate spring side contact portion 386 of the link member 385 has the end face shape thereof formed as an outline curve such that, as shown in the cam line diagram in FIG. 48, the line indicating the relation between the rotational angle of the plate spring side contact portion 386 of the link member 385 which is a driver acting in conjunction with the depressing operation of the open/close button 380, and the displacement (amount of movement) of the plate spring 395 which is a subordinate member, rapidly rises from zero (0) regarding the displacement of the plate spring 395.

Also, in this action, the link member 385 alleviates the pressing force of the open/close button 380 necessary for strongly pressing the plate spring 395, set to a predetermined high tension, against the brake bar 361 by the principle of leverage using the longitudinal direction length with the pin 379a turnably supporting the plate spring side contact portion 386 as a supporting pint.

The plate spring 395 pressed in the direction of the arrow K further presses the brake bar 361 with the pressing portion 395a thereof from the point in time at which turning of the link member 385 starts, and also brakes the brake bar 361 with the entire area thereof in contact with the brake bar 361.

Now, the amount of depressing the open/close button 380, and the braking force generated by the force of the plate spring 395 pressing against the brake bar 361, described earlier, will be described with reference to the line diagram shown in FIG. 49.

As shown in FIG. 49, as the amount of depressing of the open/close button 380 increases, the pressing force of the plate spring 395 against the brake bar 361 increases, and the braking force on the brake bar 361 increases. As described above, immediately following action due to the depressing operation of the open/close button 380, the pressing force of the plate spring 395 against the brake bar 361 rapidly increases due to the plate spring side contact portion 386 of the link member 385, so that the plate spring 395 generates a predetermined braking force F3 sufficient to brake the brake bar 361.

Subsequently, due to the outline curve shape of the plate spring side contact portion 386, even in the event that the amount of depressing of the open/close button 380 increases, the plate spring 395 maintains the braking force F3 braking the brake bar 361. Thus, the brake bar 361 is pressured such that a part thereof is sandwiched between the plate spring 395 and the groove portion 327C, in the groove portion 327C of the cover exterior member 327c, and accordingly cannot move in the longitudinal axial direction of the operation portion 303 due to the friction thereof.

Note that the braking force F1 shown in FIG. 49 represents the braking force necessary for stopping the brake bar 361 which is provided with a predetermined frictional force by the distal end side exterior member 327a and the groove portion 327C of the cover exterior member 327c, due to the pressing force of the pressing portion 395a of the plate spring 395, even in the event that the surgeon releases the two variable angle levers 306 from the hand.

Also, the braking force F2 represents a braking force including a margin for maintaining a state wherein the brake lever 361 is sufficiently stopped regardless of any angle of the needle driver 301, in a state that the surgeon has released the two variable angle levers 306 from the hand.

That is to say, in a state wherein the surgeon is not operating the open/close button 380, the brake lever 361 is provided with the braking force F2 regardless of any angle of the needle driver 301, and constantly maintains a stopped state. Accordingly, the treatment portion 304 maintains a state in a sure manner wherein the desired angle of the surgeon as to the axis of the insertion portion 302 is kept, in a sure manner.

As a result of the above, the needle driver 301 of the present invention according to the present embodiment is configured such that, as with the first embodiment, even in a casuture herein the open/close button 380 is pressed and force is generated such that the traction wire 314 tries to be straight due to the tension pulling toward the proximal end side, the plate spring 395 presses the brake bar 361 and stops movement of the brake bar 361, whereby a state in which the treatment portion 304 has been changed to a predetermined angle as to the axis of the insertion portion 302 is maintained in a sure manner.

Also, in addition to the advantages of the first embodiment, the needle driver 301 according to the present embodiment can generate a powerful pressing force for the link member 385 to cause the plate spring 395 to instantaneously stop the brake bar 361 in a sure manner, immediately after the depressing operation of the open/close button 380. Accordingly, the surgeon can maintain, in a sure manner, a state in which the treatment portion 304 has been changed to a predetermined angle as to the axis of the insertion portion 302, at the time of starting the pressing operation of the open/close button 380 for an opening/closing operation of the movable gripping piece 326. Note that the braking force acting upon the plate spring 395 can be changed with regard to the timing of generation thereof, change in amount of force, and so forth, by setting the outline curve formed on the plate spring side contact portion 386 of the link member 385 to assume various curves.

Also, the depressing force necessary for the open/close button 380 to be pressed by the surgeon for maintaining the angle of the treatment portion 304 at the time of opening/closing operations of the movable gripping piece 326 is alleviated due to the principle of leverage with the link member 385, so that the brake bar 361 can be braked in a sure manner with a light depressing operating force.

Also, as described above, with the needle driver 301 according to the present embodiment, the wire end 390 comes into direct contact with the contact portion 383 of the open/close button 380 and can move the traction wire 314 to the proximal end side, whereby there is no need to provide a separate link mechanism within the inner space formed in the operation portion 303, so the configuration is such that the number of parts can be reduced.

According to the present embodiment, a surgical treatment instrument with good operability for anastomosis of tissue or the like using an endoscope can be realized. Anastomosis of tissue or the like using an endoscope is facilitated, so the quality of surgery can be improved and surgery time can be reduced, leading to earlier patient discharge and earlier return to normal life.

Also, the present invention is not restricted to the above-described embodiments, and various modifications and alterations may be made within the scope of the present invention.

What is claimed is:
1. A surgical treatment instrument comprising:
an insertion portion;
an operation portion provided on a proximal end of the insertion portion;
a treatment portion provided so as to extend from a distal end of the insertion portion;
two gripping members provided on the treatment portion, each having a gripping face;
a variable angle operating member provided on the operation portion to change the treatment portion to a predetermined angle by being operated to move in a direction along a distal end side and a proximal end side of the operation portion;
a transmitting member to change an angle of the treatment portion by moving forward/backward along a longitudinal axial direction of the insertion portion in conjunction with the operation of the variable angle operating member;
a braked member provided within the operation portion, the braked member being connected to the transmitting member which moves forward/backward by the operation of the variable angle operating member, and moving forward/backward within the operating portion;
a braking member provided within the operation portion to brake the braked member;
an open/close operating member provided at the operation portion and operatively connected with the braking member and at least one of the two gripping members so as to move the at least one of the two gripping members for performing opening/closing; and
a pressing member which has the braking member and presses the open/close operating member in a direction of separating from the braked member,
wherein:
when the open/close operating member is displaced to an operation position by an operation against the pressing force of the pressing member so as to move the at least one of the two gripping members for performing the opening/closing, the opening/closing operation member simultaneously presses the braking member toward the braked member in conjunction with bending of the pressing member so as to increase a friction resistance with respect to the braked member, so that the movement of the braked member is stopped to brake the forward/backward movement of the transmitting member to thereby maintain the predetermined angle of the treatment portion, and
when the operation of the open/close operating member is released such that the open/close operating member is displaced from the operation position to a non-operation position by being pressed by the pressing member, the braking member simultaneously moves in conjunction with restoration of the pressing member, so that the pressing of the braking member toward the braked member is released to lower the friction resistance and the braked member is made movable to allow the forward/backward movement of the transmitting member.

2. A surgical treatment instrument according to claim 1, wherein the braking member is provided between the open/close operating member and the braked member, and includes a cam mechanism operating in conjunction with the operation of the open/close operating member.

3. A surgical treatment instrument according to claim 2, wherein the cam mechanism has a driver having an outline curve so that the braking member applies necessary predetermined braking force to stop the braked member before at least one of the two gripping members is moved by the open/close operating member.

4. A surgical treatment instrument according to claim 2, having an elastic element between the cam mechanism and the braked member.

5. A surgical treatment instrument according to claim 3, having an elastic element between the cam mechanism and the braked member.

6. A surgical treatment instrument according to claim 1, wherein the braked member is provided within the operation portion so that predetermined frictional force is applied.

7. A surgical treatment instrument according to claim 2, wherein the braked member is provided within the operation portion so that predetermined frictional force is applied.

8. A surgical treatment instrument according to claim 3, wherein the braked member is provided within the operation portion so that predetermined frictional force is applied.

9. A surgical treatment instrument according to claim 4, wherein the braked member is provided within the operation portion so that predetermined frictional force is applied.

10. A surgical treatment instrument according to claim 5, wherein the braked member is provided within the operation portion so that predetermined frictional force is applied.

11. A surgical treatment instrument according to claim 1, wherein the braking member continually stops the braked member during the time wherein at least one of the two gripping members is moved by the open/close operating member.

12. A surgical treatment instrument according to claim 2, wherein the braking member continually stops the braked member during the time wherein at least one of the two gripping members is moved by the open/close operating member.

13. A surgical treatment instrument according to claim 3, wherein the braking member continually stops the braked member during the time wherein at least one of the two gripping members is moved by the open/close operating member.

14. A surgical treatment instrument according to claim 4, wherein the braking member continually stops the braked member during the time wherein at least one of the two gripping members is moved by the open/close operating member.

15. A surgical treatment instrument according to claim 5, wherein the braking member continually stops the braked member during the time wherein at least one of the two gripping members is moved by the open/close operating member.

16. A surgical treatment instrument according to claim 6, wherein the braking member continually stops the braked member during the time wherein at least one of the two gripping members is moved by the open/close operating member.

17. A surgical treatment instrument according to claim 7, wherein the braking member continually stops the braked member during the time wherein at least one of the two gripping members is moved by the open/close operating member.

18. A surgical treatment instrument according to claim 8, wherein the braking member continually stops the braked member during the time wherein at least one of the two gripping members is moved by the open/close operating member.

19. A surgical treatment instrument according to claim 9, wherein the braking member continually stops the braked member during the time wherein at least one of the two gripping members is moved by the open/close operating member.

20. A surgical treatment instrument according to claim 10, wherein the braking member continually stops the braked member during the time wherein at least one of the two gripping members is moved by the open/close operating member.

21. A surgical treatment instrument according to claim 1, wherein the braking member includes an elastic member.

* * * * *